(12) United States Patent
Chen

(10) Patent No.: US 7,931,896 B2
(45) Date of Patent: Apr. 26, 2011

(54) COMPOSITIONS AND METHODS FOR TREATING INFLAMMATION AND AUTO-IMMUNE DISEASES

(75) Inventor: Lieping Chen, Sparks Glencoe, MD (US)

(73) Assignee: The Johns Hopkins University, Baltimore, MD (US)

( * ) Notice: Subject to any disclaimer, the term of this patent is extended or adjusted under 35 U.S.C. 154(b) by 243 days.

(21) Appl. No.: 11/965,425

(22) Filed: Dec. 27, 2007

(65) Prior Publication Data

US 2008/0160036 A1    Jul. 3, 2008

Related U.S. Application Data

(60) Provisional application No. 60/877,319, filed on Dec. 27, 2006, provisional application No. 60/949,742, filed on Jul. 13, 2007.

(51) Int. Cl.
*A61K 39/395* (2006.01)
(52) U.S. Cl. .................................................. 424/130.1
(58) Field of Classification Search .................. None
See application file for complete search history.

(56) References Cited

U.S. PATENT DOCUMENTS

| | | | |
|---|---|---|---|
| 3,840,513 A | 10/1974 | Umezawa et al. |
| 4,272,398 A | 6/1981 | Jaffe |
| 4,376,110 A | 3/1983 | David et al. |
| 4,634,664 A | 1/1987 | Oestberg |
| 4,634,666 A | 1/1987 | Engleman et al. |
| 4,650,764 A | 3/1987 | Temin |
| 4,704,692 A | 11/1987 | Ladner et al. |
| 4,769,330 A | 9/1988 | Paoletti et al. |
| 4,853,871 A | 8/1989 | Pantoliano et al. |
| 4,861,627 A | 8/1989 | Mathiowitz et al. |
| 4,861,719 A | 8/1989 | Miller |
| 4,925,673 A | 5/1990 | Steiner et al. |
| 4,946,778 A | 8/1990 | Ladner et al. |
| 4,980,289 A | 12/1990 | Temin et al. |
| 5,013,556 A | 5/1991 | Woodle et al. |
| 5,120,727 A | 6/1992 | Kao et al. |
| 5,124,263 A | 6/1992 | Temin et al. |
| 5,155,020 A | 10/1992 | Paoletti et al. |
| 5,162,333 A | 11/1992 | Failli et al. |
| 5,175,099 A | 12/1992 | Wills |
| 5,202,332 A | 4/1993 | Hughes et al. |
| 5,204,243 A | 4/1993 | Paoletti et al. |
| 5,225,336 A | 7/1993 | Paoletti |
| 5,225,539 A | 7/1993 | Winter |
| 5,240,846 A | 8/1993 | Collins et al. |
| 5,260,203 A | 11/1993 | Ladner et al. |
| 5,278,056 A | 1/1994 | Bank et al. |
| 5,284,656 A | 2/1994 | Platz et al. |
| 5,304,489 A | 4/1994 | Rosen |
| 5,385,908 A | 1/1995 | Nelson et al. |
| 5,451,569 A | 9/1995 | Wong et al. |
| 5,484,790 A | 1/1996 | Failli et al. |
| 5,530,006 A | 6/1996 | Waranis et al. |
| 5,530,101 A | 6/1996 | Queen |
| 5,545,806 A | 8/1996 | Lonberg |
| 5,559,112 A | 9/1996 | Skotnicki et al. |
| 5,565,332 A | 10/1996 | Hoogenboom |
| 5,567,709 A | 10/1996 | Skotnicki et al. |
| 5,569,825 A | 10/1996 | Lonberg |
| 5,585,089 A | 12/1996 | Queen |
| 5,625,126 A | 4/1997 | Lonberg |
| 5,633,425 A | 5/1997 | Lonberg |
| 5,661,016 A | 8/1997 | Lonberg |
| 5,693,761 A | 12/1997 | Queen |
| 5,693,762 A | 12/1997 | Queen |
| 5,733,743 A | 3/1998 | Johnson |
| 5,736,142 A | 4/1998 | Sette |
| 5,741,957 A | 4/1998 | Deboer |
| 5,770,429 A | 6/1998 | Lonberg |
| 5,780,462 A | 7/1998 | Lee et al. |
| 5,789,650 A | 8/1998 | Lonberg |
| 5,814,318 A | 9/1998 | Lonberg |
| 5,837,242 A | 11/1998 | Holliger |
| 5,849,992 A | 12/1998 | Meade |
| 5,858,657 A | 1/1999 | Winter |
| 5,871,907 A | 2/1999 | Winter |
| 5,874,299 A | 2/1999 | Lonberg |
| 5,877,218 A | 3/1999 | Herzig |
| 5,877,397 A | 3/1999 | Lonberg |
| 5,989,591 A | 11/1999 | Nagi et al. |
| 6,015,809 A | 1/2000 | Zhu et al. |
| 6,468,546 B1 | 10/2002 | Mitcham et al. |
| 6,537,968 B1 | 3/2003 | Lezdey et al. |
| 6,891,030 B2 | 5/2005 | Chen |
| 6,962,980 B2 | 11/2005 | Mitcham et al. |
| 7,189,563 B2 | 3/2007 | Eaton et al. |
| 7,202,334 B1 | 4/2007 | Mitcham et al. |
| 7,304,149 B2 * | 12/2007 | Murphy et al. ............ 536/23.5 |
| 2002/0165347 A1 | 11/2002 | Fox et al. |

(Continued)

FOREIGN PATENT DOCUMENTS

WO    WO 90/07861    7/1990

(Continued)

OTHER PUBLICATIONS

Huang Z., Pharmacology and Therapeutics, 2000, 86: 201-215.*

(Continued)

*Primary Examiner* — Ilia Ouspenski
(74) *Attorney, Agent, or Firm* — Pabst Patent Group LLP

(57) ABSTRACT

Compositions containing soluble B7-H4 (sH4) antagonists in an amount effective to reduce, inhibit, or mitigate an inflammatory response in an individual and methods for the treatment or prophylaxis of inflammatory disorders and autoimmune diseases or disorders are provided. Soluble H4 has been discovered to interfere with B7-H4 activity including B7-H4's activity as an inhibitor of T cell immunity. Thus, interference of sH4 biological activity is an effective method to restore B7-H4 activity and thereby provide an effective method for treating inflammatory diseases or disorders including autoimmune diseases or disorders. B7-H4Ig could also work as an agonist to suppress both humoral and cellular autoimmunity.

16 Claims, 21 Drawing Sheets

U.S. PATENT DOCUMENTS

| | | |
|---|---|---|
| 2002/0168762 A1 | 11/2002 | Chen |
| 2004/0152105 A1 | 8/2004 | Vogt et al. |
| 2004/0175380 A1 | 9/2004 | Allison et al. |
| 2004/0229795 A1 | 11/2004 | Roemisch et al. |
| 2005/0163772 A1 | 7/2005 | Dong et al. |
| 2005/0202536 A1 | 9/2005 | Chen et al. |
| 2008/0159998 A1 | 7/2008 | Ichim |
| 2008/0177039 A1 | 7/2008 | Chen |
| 2008/0206235 A1 | 8/2008 | Chen |
| 2009/0011444 A1 | 1/2009 | Chen |
| 2009/0022747 A1 | 1/2009 | Chen |
| 2009/0087416 A1 | 4/2009 | Chen |
| 2009/0124573 A1 | 5/2009 | Mazmanian et al. |
| 2009/0142342 A1 | 6/2009 | Chen |

FOREIGN PATENT DOCUMENTS

| | | |
|---|---|---|
| WO | WO 91/10741 | 7/1991 |
| WO | WO 91/17271 | 11/1991 |
| WO | WO 92/01047 | 1/1992 |
| WO | WO 92/20791 | 11/1992 |
| WO | WO93/01222 | 1/1993 |
| WO | WO 95/04738 | 2/1995 |
| WO | WO 95/07707 | 3/1995 |
| WO | WO 95/16691 | 6/1995 |
| WO | WO 95/22972 | 8/1995 |
| WO | WO 97/17613 | 5/1997 |
| WO | WO 97/17614 | 5/1997 |
| WO | WO 98/23635 | 6/1998 |
| WO | WO 99/63088 | 12/1999 |
| WO | WO 00/01385 | 1/2000 |
| WO | WO 00/12758 | 3/2000 |
| WO | WO 00/36107 | 6/2000 |
| WO | WO 02/02587 | 1/2002 |
| WO | WO 2004/000221 | 12/2003 |
| WO | WO 2004/022594 | 3/2004 |
| WO | WO 2004/113500 | 12/2004 |
| WO | WO 2006/101487 | 9/2006 |
| WO | WO 2006/124667 | 11/2006 |
| WO | WO 2006/133396 | 12/2006 |
| WO | WO 2007/039150 | 4/2007 |
| WO | WO 2007/067681 | 6/2007 |
| WO | WO 2008/083239 | 7/2008 |
| WO | WO 2009/089036 | 7/2009 |

OTHER PUBLICATIONS

Amoura, et al., "Nucleosome-restricted antibodies are detected before anti-dsDNA and/or antihistone antibodies in serum of MRL-Mp 1pr/1pr and +/+ mice, and are present in kidney eluates of lupus mice with proteinuria", *Arthritis Rheum.*, 37(11):1684-8 (1994).

Bonder, et al., "Essential role for neutrophil recruitment to the liver in concanavalin A-induced hepatitis", *J. Immunol.*, 172(1):45-53 (2004).

Brown, et al., "Treatment of mice with the neutrophil-depleting antibody RB6-8C5 results in early development of experimental lyme arthritis via the recruitment of Fr-I- polymorphonuclear leukocyte-like cells", *Infect. Immun.*, 72(9):4956-65 (2004).

Cassatella, "The production of cytokines by polymorphonuclear neutrophils", *Immunol. Today*, 16(1):21-6 (1995).

Chapoval, et al., B7-H3: a costimulatory molecule for T cell activation and IFN-gamma production, *Nat. Immunol.*, 2(3):269-74 (2001).

Chen, "Co-inhibitory molecules of the B7-CD28 family in the control of T-cell Immunity", *Nat. Rev. Immunol.*, 4(5):33647 (2004).

Coyle, et al., "The CD28-related molecule ICOS is required for effective T cell-dependent immune responses", *Immunity*, 13(1):95-105 (2000).

Coyle, et al., "The expanding B7 superfamily: increasing complexity in costimulatory signals regulating T cell function", *Nat. Immunol.*, 2(3):203-9 (2001).

Crystal, "Gene therapy strategies for pulmonary disease", *Am. J. Med.*, 92(6A):44S-52S (1992).

De Oca, et al., "Polymorphonuclear neutrophils are necessary for the recruitment of CD8(+) T cells in the liver in a pregnant mouse model of Chiamydophila abortus (Chlamydia psittaci serotype I) infection", *Infect. Immun.*, 68(3):1746-51 (2000).

Dong, et al., "Costimulating aberrant T cell responses by B7-H1 autoantibodies in rheumatoid arthritis", *J. Clin. Invest.*, 111(3):363-70 (2003).

Eyles, et al., "Granulocyte colony-stimulating factor and neutrophils-forgotten mediators of inflammatory disease", *Nat. Clin. Pract. Rheumatol.*, 2(9):500-1 0 (2006).

Faas, et al., "Primary structure and functional characterization of a soluble, alternatively spliced form of B7-1", *J. Immunol.*, 164(12):6340-8 (2000).

Fava, et al., "Critical role of peripheral blood phagocytes and the involvement of complement in tumour necrosis factor enhancement of passive collagen-arthritis", *Clin. Exp. Immuno.*, 94(2): 261-8 (1993).

GENBANK Accession No. AY280972, (2003).

Halloran, et al., "The role of an epithelial neutrophil-activating peptide-78-like protein in rat adjuvant-induced arthritis", *J. Immunol.*, 162(12):7492-500 (1999).

Hubbard, et al., "Anti-neutrophil-elastase defenses of the lower respiratory tract in alpha 1-antitrypsin deficiency directly augmented with an aerosol of alpha 1-antitrypsin", *Ann. Intern. Med.*, 111(3):206-12 (1989).

Jeannin, et al., "Soluble CD86 is a costimulatory molecule for human T lymphocytes", *Immunity*, 13(3):303-12 (2000).

Kakimoto, et al., "Suppressive effect of a neutrophil elastase inhibitor on the development of collagen-induced arthritis", *Cell Immunol.*, 165(1):26-32 (1995).

Keir and Sharpe, "The B7/CD28 costimulatory family in autoimmunity", *Immunol. Rev.*, 204:128-43 (2005).

Kelley and Roths, "Interaction of mutant lpr gene with background strain influences renal disease", *Clin. Immuno. Immunopathol.*, 37(2):220-9 (1985).

Knapp and Liu, "Hydrodynamic delivery of DNA", *Methods Mol. Bio.*, 245:245-50 (2004).

Kotzin, "Systemic lupus erythematosus", *Cell*, 85(3), 303-6 (1996).

Krambeck, et al., "B7-H4 expression in renal cell carcinoma and tumor vasculature: associations with cancer progression and survival", *Proc. Natl. Acad. Sci. USA*, 103(27):10391-10396 (2006).

Kryczek, et al., "Cutting edge: Induction of B7-H4 on APCs through IL-10: Novel suppressive mode for regulatory T cells", *J. Immunol.*, 177(1):40-44 (2006).

Li, et al., "Biochemical analysis of the regulatory T cell protein lymphocyte activation gene-3 (LAG-3 CD223)", *J. Immunol.*, 173(11):6806-1 2 (2004).

Liang, et al., "Autoantibody responses and pathology regulated by B7-1 and B7-2 costimulation in MRL/1pr lupus", *J. Immunol.*, 165(6):3436-43 (2000).

Lissoni, "Intracavitary administration of interleukin-2 as palliative therapy for neoplastic effusions", *Tumori*, 78(2):118-120 (1992).

McColl, et al., "Treatment with anti-granulocyte antibodies inhibits the effector phase of experimental autoimmune encephalomyelitis", *J. Immunol.*, 161(11), 6421-6 (1998).

Metzler, et al., "Solution structure of human CTLA-4 and delineation of a CD80/CD86 binding site conserved in CD28", *Nat. Struct. Biol.*, 4(7):527-31 (1997).

Michael, et al., "The hematologic aspects of disseminated (systemic) lupus erythematosus", *Blood*, 6(11):1059-72 (1951).

Nandakumar, et al., "Collagen type II-specific monoclonal antibody-induced arthritis in mice: description of the disease and the influence of age, sex, and genes", *Am. J. Pathol.*, 163(5), 1827-37 (2003).

Parra and Bond, "Inverse agonism: from curiosity to accepted dogma, but is it clinically relevant?", *Curr. Opin. Pharmacol.*, 7(2):146-50 (2007).

Pillinger and Abramson, "The neutrophil in rheumatoid arthritis", *Rheum. Dis. Clin. North. Am.*, 21(3):691-714 (1995).

Prasad, et al., "B7S1, a novel B7 family member that negatively regulates T cell activation", *Immunity*, 18(6):863-873 (2003).

Quismorio, "Hemotalogica and lymphoid abnormalities in systemic lupus etythematosus" in Dubio's Lupus Erythematosus, (eds. Wallace and Han), Lippincott & Williams:Phillidephia; PA,pp. 793-819 (2002).

Salceda, et al. "The immunomodulatory protein B7-H4 is overexpressed in breast and ovarian cancers and promotes epithelial cell transformation", *Exp. Cell Res.*, 306(1):128-41 (2005).

Santos, et al., "Anti-neutrophil monoclonal antibody therapy inhibits the development of adjuvant arthritis", *Clin. Exp. Immunol.*, 107(2):24-53 (1997).
Scapini, et al., "The neutrophil as a cellular source of chemokines", *Immunol. Rev.*, 177: 195-203 (2000).
Schimmer, et al., "Streptococcal cell wall-induced arthritis. Requirements for neutrophils, P-selectin, intercellular adhesion molecule-I, and macrophage-inflammatory protein-2", *J. Immunol.*, 159(8):4103-8.
Simon, et al., "B7-H4 is a novel membrane-bound protein and a candidate serum and tissue biomarker for ovarian cancer", *Cancer Res.*, 66(3):1570-1575 (2006).
Skolnick, et al., "From genes to protein structure and function: novel applications of computational approaches in the genomic era", *Trends Biotechnol.*, 18(1):34-9 (2000).
Sun, et al., "B7-H3 and B7-H4 expression in non-small-cell lung cancer", *Lung Cancer*, 53 (2):143-151 (2006).
Sun, et al., "Costimulatory molecule-targeted antibody therapy of a spontaneous autoimmune disease", *Nat. Med.* 8(12):1405-13 (2002).
Tada, et al., "CD28-deficient mice are highly resistant to collagen-induced arthritis", *J. Immunol.*, 162(1):203-8 (1999).
Tringler, et al., "B7-H4 is highly expressed in ductal and lobular breast cancer", *Clin. Cancer Res.*, 11(5):1842-1848 (2005).
Tringler, et al., "B7-H4 overexpression in ovarian tumors", *Gynecol. Oncol.*, 100(1):44-52 (2005).
Wan, et al., "Aberrant regulation of synovial T cell activation by soluble costimulatory molecules in rheumatoid arthritis", *J.Immunol.*, 177(12):8844-50 (2006).
Watanabe, et al., "BTLA is a lymphocyte inhibitory receptor with similarities to CTLA-4 and PD-1", *Nature Immunol.*, 4(7):670-679 (2006).
Wipke and Allen, "Essential role of neutrophils in the initiation and progression of a murine model of rheumatoid arthritis", *J. Immunol.*, 167(3):1601-8 (2001).
Zang, et al., "B7x: A widely expressed 87 family member that inhibits T cell activation", *Proc. Natl. Acad. Sci. USA*, 100(18):10388-10392 (2003).
Adachi, "Tumoricidal effect of human macrophage-colony-stimulating factor against human-ovarian-carcinoma-bearing athymic mice and its therapeutic effect when combined with cisplatin", *Cancer Immunol. Immunother.* 37(1): 1-6, (1993).
Aldovini, "Humoral and cell-mediated immune responses to live recombinant BCG-HIV vaccines", *Nature*, 351:479-482 (1991).
Alexander, "Development of high potency universal DR-restricted helper epitopes by modification of high affinity DR-blocking peptides", Immunity, 1(9):751-761 (1994).
Bird, "Single-chain antigen-binding proteins", *Science*, 242:423-426 (1988).
Bona, C. et al., CRC Crit. Rev. Immunol., pp. 33-81 (1981).
Bordignon, "Gene therapy in peripheral blood lymphocytes and bone marrow for ADA-immunodeficient patients", *Science*, 270:470-475 (1995).
Chapman, "A phase I trial of intraperitoneal recombinant interleukin 2 in patients with ovarian carcinoma", *Investigational New Drugs*, 6(3):179-188. (1988).
Chapoval et al. *Methods Mol. Med.* 45:247-255 (2000).
Chapoval, "Immunoglobulin fusion proteins as a tool for evaluation of T-cell costimulatory molecules", *Mol. Biotechnol.*, 21:259-64 (2002).
Chen, "Impaired glucose homeostasis, neutrophil trafficking and function in mice lacking the glucose-6-phosphate transporter", *Hum. Mol. Genet.*, 12:2547-2558 (2003).
Chen, "Soluble TNF-alpha receptors are constitutively shed and downregulate adhesion molecule expression in malignant gliomas", *J. Neuropathol. Exp. Neurol.*, 56(5), 541-550 (1997).
Chicz, "Specificity and promiscuity among naturally processed peptides bound to HLA-DR alleles", *J. Exp. Med..*, 178(1):27-47 (1993).
Choi, "Genomic organization and expression analysis of B7-H4, an immune inhibitory molecule of the B7 family", *J. Immunol*, 171:4650-4 (2003).
Co, "Chimeric and humanized antibodies with specificity for the CD33 antigen", *J. Immunol.* 148(4):1149-1154 (1992).

Dong, "B7-H1 determines accumulation and deletion of intrahepatic CD8(+) T lymphocytes", *Immunity*, 20:327-336 (2004).
Dong, "Tumor-associated B7-H1 promotes T-cell apoptosis: a potential mechanism of immune evasion", *Nature Med.*, 8:793-800 (2002).
Edwards, "Comparison of toxicity and survival following intraperitoneal recombinant interleukin-2 for persistent ovarian cancer after platinum: twenty-four-hour versus 7-day infusion", *J. Clin. Oncol.*, 15(11):3399-3407 (1997).
Edwards, "The formation of a structure with the features of synovial lining by subcutaneous injection of air: an in vivo tissue culture system", *J. Pathol.*, 134:147-156 (1981).
Falk, "Pool sequencing of natural HLA-DR, DQ, and DP ligands reveals detailed peptide motifs, constraints of processing, and general rules", *Immunogenetics*, 39(4):230-242 (1994).
Feldmann, "Rheumatoid arthritis", *Cell*, 85(3):307-10 (1996).
Fink, "Monoclonal antibodies as diagnostic reagents for the identification and characterization of human tumor antigens", *Prog. Clin. Pathol.*, 9:121-133 (1984).
Freedman, "Intraperitoneal adoptive immunotherapy of ovarian carcinoma with tumor-infiltrating lymphocytes and low-dose recombinant interleukin-2: a pilot trial", *J. of Immunotherapy Emphasis Tumor Immunol.*, 16(3):198-210 (1994).
Guatelli, "Isothermal, in vitro amplification of nucleic acids by a multienzyme reaction modeled after retroviral replication", *Proc. Natl. Acad. Sci. USA*, 87(5):1874-1878 (1990).
Hammer, "Promiscuous and allele-specific anchors in HLA-DR-binding peptides", *Cell*, 74(1):197-203 (1993).
Henikoff, "Amino acid substitution matrices from protein blocks", *Proc. Natl. Acad. Sci. U.S.A.*, 89:10915-10919 (1992).
Hickman, "Gene expression following direct injection of DNA into liver", *Hum. Gene Ther.*, 5:1477-1483 (1994).
Hill, et al., "A field guide to foldamers", *Chem Rev.*, 101(12):3893-4012 (2001).
Hochman, "An active antibody fragment (Fv) composed of the variable portions of heavy and light chains", *Biochemistry*, 12:1130-1135 (1973).
Hoiseth and Stocker, "Aromatic-dependent Salmonella typhimurium are non-virulent and effective as live vaccines", *Nature*, 291, 238-239 (1981).
Huse, "Generation of a large combinatorial library of the immunoglobulin repertoire in phage lambda", *Science*, 246(4935):1275-1281 (1989).
Huston, "Protein engineering of antibody binding sites: recovery of specific activity in an anti-digoxin single-chain Fv analogue produced in *Escherichia coli*", *Proc. Natl. Acad. Sci. USA*, 85:5879-5883 (1988).
Ikonomidis, "Delivery of a viral antigen to the class I processing and presentation pathway by Listeria monocytogenes", *J. Exp. Med.*, 180:2209-2218 (1994).
Jablonska and Peitruska, "Release of soluble tumor necrosis factor receptors from polymorphonuclear cells of breast cancer patients", *Arch. Immunol. Ther. Exp.* (Warsz), 45(5-6), 449-453 (1997).
Jerne, "Towards a network theory of the immune system" *Ann. Immunol.*, 125C:373-389 (1974).
Jost, "Mammalian expression and secretion of functional single-chain Fv molecules", *J Biol Chem.*, 269:26267-26273 (1994).
Kamata, "src homology 2 domain-containing tyrosine phosphatase SHP-1 controls the development of allergic airway inflammation", *J. Clin. Invest.*, 111:109-119 (2003).
Kikuchi, "Effects of granulocyte-colony-stimulating factor and interleukin-2 on ascites formation and the survival time of nude mice bearing human ovarian cancer cells", *Cancer Immunol. Immunother.*, 43(5): 257-261 (1996).
Kohler and Milstein, "Continuous cultures of fused cells secreting antibody of predefined specificity", *Nature*, 256:495-497 (1975).
Kryczek, "B7-H4 expression identifies a novel suppressive macrophage population in human ovarian carcinoma", *J Exp. Med.*, 203:871-881 (2006).
Lewis, "PCRs Competitors Are Alive and Well and Moving Rapidly Towards Commercialization", *Genetic Engineering News* 12:1-3 (1992).
Lissoni, "Intracavitary administration of interleukin-2 as palliative therapy for neoplastic effusions", *Tumori*, 78(2):118-120 (1992).

Liu, "Cationic transfection lipids", *Curr. Med. Chem.*, 10:1307-1315 (2003).

Lowenstein, "Simultaneous detection of amplicon and HSV-1 helper encoded proteins reveals that neurons and astrocytoma cells do express amplicon-borne transgenes in the absence of synthesis of virus immediate early proteins", *Brain Res. Molec. Brain Res*, 30:169-175 (1995).

Mathiowitz and Langer, "Polyanhydride microspheres as drug carriers. I. Hot-melt microencapsulation", *J. Controlled Release*, 5:13-22 (1987).

Mathiowitz, "Novel microcapsules for delivery systems", *Reactive Polymers*, 6:275-283 (1987).

Mathiowitz, "Polyanhydride microspheres as drug carriers. II. microencapsulation by solvent removal", *J. Appl. Polymer Sci.*, 35:755-774 (1988).

Moreland, "Treatment of rheumatoid arthritis with a recombinant human tumor necrosis factor receptor (p75)-Fc fusion protein", *N. Engl. J. Med.*, 337:141-7 (1997).

Moss, "Poxvirus expression vectors", *Cuff. Top. Microbiol. Immunol.*, 158:25-38 (1992).

Moss, "Poxvirus vectors: cytoplasmic expression of transferred genes", *Curr. Opin. Genet. Dev.*, 3:86-90 (1993).

Moss, "Use of vaccinia virus as an infectious molecular cloning and expression vector", *Gene Amplif Anal* 3:201-213 (1983).

Moss, "Vaccinia virus vectors", *Biotechnology*, 20: 345-362 (1992).

Moss, "Vaccinia virus: a tool for research and vaccine development", *Science* 252:1662-1667 (1991).

Murphy, "Long-term correction of obesity and diabetes in genetically obese mice by a single intramuscular injection of recombinant adeno-associated virus encoding mouse leptin", *Proc Natl Acad Sci.*, 94:13921-13926 (1997).

Nathan, "Neutrophils and immunity: challenges and opportunities", *Nature Rev. Immunol.*, 6:173-182 (2006).

Needleman and Wunsch, "A general method applicable to the search for similarities in the amino acid sequence of two proteins", *J. Mol. Biol.*, 48:443-453 (1970).

Newmark, et al. (1982) J. Appl. Biochem. 4:185-189.

O'Brien, "An improved method of preparing microcarriers for biolistic transfection", *Brain Res. Brain Res. Protco.*, 10:12-15 (2002).

Oestberg et al., Hybridoma 2:361-367 (1983).

Ottow, et al., *Cellular Immunology*, 104: 366-376 (1987).

Peplinski, "Vaccinia virus for human gene therapy", *Surgical Oncology Clinics of North America*, 7: 575-588 (1998).

Piccini, "Vaccinia: virus, vector, vaccine", *Adv. Virus Res.*, 34:43-64 (1988).

Pluckthun, "Expression of functional antibody Fv and Fab fragments in *Escherichia coli*", *Methods Enzymol.*, 178: 497-515 (1989).

Poirier, "Protective immunity evoked by oral administration of attenuated aroA Salmonella typhimurium expressing cloned streptococcal M protein", *J. Exp. Med.*, 168:25-32 (1988).

Queen, "A humanized antibody that binds to the interleukin 2 receptor", *Proc. Natl. Acad. Sci. USA*, 86(24):10029-10033 (1989).

Queen, "Cell-type specific regulation of a kappa immunoglobulin gene by promoter and enhancer elements", *Immunol. Rev.*, 89:49 (1986).

Radsak, "The heat shock protein Gp96 binds to human neutrophils and monocytes and stimulates effector functions", *Blood*, 101:2810-2815 (2003).

Radsak, "Triggering receptor expressed on myeloid cells-1 in neutrophil inflammatory responses: differential regulation of activation and survival", *J. Immunol.*, 172:4956-4963 (2004).

Rajewsky, "Genetics, expression, and function of idiotypes", *Ann. Rev. Immunol.*, 1:569-607 (1983).

Reynolds, "Chimeric viral vectors—the best of both worlds", *Molecular Medicine Today*, 5:25-31 (1999).

Rousseaux, "Optimal conditions for the preparation of proteolytic fragments from monoclonal IgG of different rat IgG subclasses", *Meth. Enzymol.*, 121:663-69 (1986).

Sadoff, "Oral Salmonella typhimurium vaccine expressing circumsporozoite protein protects against malaria", *Science*, 240:336-338 (1988).

Samulski, "Targeted integration of adeno-associated virus (AAV) into human chromosome 19", *EMBO J.*, 10:3941-3950 (1991).

Schafer, "Induction of a cellular immune response to a foreign antigen by a recombinant Listeria monocytogenes vaccine", *J. Immunol.*, 149:53-59 (1992).

Sharon, "Preparation of Fv fragment from the mouse myeloma XRPC-25 immunoglobulin possessing anti-dinitrophenyl activity", *Biochemistry*, 15:1591-1594 (1976).

Sica, "B7-H4, a molecule of the B7 family, negatively regulates T cell immunity", *Immunity*, 18:849-861 (2003).

Sinigaglia, "A malaria T-cell epitope recognized in association with most mouse and human MHC class II molecules", *Nature*, 336(6201):778-780 (1988).

Son, "Cisplatin-based interferon gamma gene therapy of murine ovarian carcinoma", *Cancer Gene Therapy*, 4(6):391-396 (1997).

Soriano, "Targeted and nontargeted liposomes for in vivo transfer to rat liver cells of a plasmid containing the preproinsulin I gene", *Proc. Natl. Acad. Sci. USA*, 80:7128-7131 (1983).

Southwood, "Several common HLA-DR types share largely overlapping peptide binding repertoires", J. Immunology, 160(7):3363-3373 (1998).

Sparano, "Phase II trials of high-dose interleukin-2 and lymphokine-activated killer cells in advanced breast carcinoma and carcinoma of the lung, ovary, and pancreas and other tumors", *J. of Immunotherapy Emphasis Tumor Immunol.*, (1994).

Stone, "Viral vectors for gene delivery and gene therapy within the endocrine system", *J. Endocrinology*, 164:103-118 (2000).

Stover, "New use of BCG for recombinant vaccines", Nature, 351:456-460 (1991).

Sugaya, "Inhibition of tumor growth by direct intratumoral gene transfer of herpes simplex virus thymidine kinase gene with DNA-liposome complexes", *Hum. Gene Ther.*, 7(2):223-230 (1996).

Suh, "Generation and characterization of B7-H4/B7S1/B7x-deficient mice", *Mol. Cell. Biol.*, 26:6403-6411 (2006).

Szala, "The use of cationic liposomes DC-CHOL/DOPE and DDAB/DOPE for direct transfer of *Escherichia coli* cytosine deaminase gene into growing melanoma tumors", *Gene Therapy*, 3(11): 1026-1031 (1996).

Tamada, "Cutting edge: selective impairment of CD8+ T cell function in mice lacking the TNF superfamily member LIGHT", *J Immunol.*, 168:4832-4835 (2002).

Tamada, "Modulation of T-cell-mediated immunity in tumor and graft-versus-host disease models through the LIGHT co-stimulatory pathway", *Nature Med.*, 6:283-289 (2000).

Tamura, "B7-H1 costimulation preferentially enhances CD28-independent T-helper cell function", *Blood*, 97:1809-1816 (2001).

Titomirov, "In vivo electroporation and stable transformation of skin cells of newborn mice by plasmid DNA", *Biochim. Biophys. Acta.*, 1088:131-134 (1991).

Tsushima, "Preferential contribution of B7-H1 to programmed death-1-mediated regulation of hapten-specific allergic inflammatory responses", *Eur. J. Immunol.*, 33:2773-2782 (2003).

Urbain, "Idiotypes, recurrent idiotypes and internal images", *Ann. Immunol.* 133D(2):179-189 (1982).

Wahl, "Improved radioimaging and tumor localization with monoclonal F(ab')2", *J. Nuc. Med.* 24:316-325 (1983).

Wang, "pH-sensitive immunoliposomes mediate target-cell-specific delivery and controlled expression of a foreign gene in mouse", *Proc. Natl. Acad. Sci. USA*, 84:7851 (1987).

Weiss (1991) *Science* 254:1292-1293.

Weiss and Taylor, "Retrovirus receptors", *Cell*, 82:531-533 (1995).

Wilcox, "Ligation of CD137 receptor prevents and reverses established anergy of CD8+ cytolytic T lymphocytes in vivo", *Blood*, 103:177-184 (2004).

Williams, "Synergy between anti-CD4 and anti-tumor necrosis factor in the amelioration of established collagen-induced arthritis", *Proc. Natl. Acad. Sci. U. S. A.*, 91:2762-6 (1994).

Wilson, "Hepatocyte-directed gene transfer in vivo leads to transient improvement of hypercholesterolemia in low density lipoprotein receptor-deficient rabbits", *J. Biol. Chem.*, 267:963-967 (1992).

Winter, "Man-made antibodies", *Nature*, 349: 293-299 (1991).

Wolff, "Direct gene transfer into mouse muscle in vivo", *Science*, 247:1465-1468 (1990).

Wong, "Human GM-CSF: molecular cloning of the complementary DNA and purification of the natural and recombinant proteins", *Science*, 228(4701):810-815 (1985).

Wu, "Receptor-mediated gene delivery and expression in vivo", *J. Biol. Chem.*, 263:14621-14624 (1988).

Wu, "Targeting genes: delivery and persistent expression of a foreign gene driven by mammalian regulatory elements in vivo", *J. Biol. Chem.*, 264:16985-16987 (1989).

Yu, "Liposome-mediated in vivo E1A gene transfer suppressed dissemination of ovarian cancer cells that overexpress HER-2/neu", *Oncogene*, 11(7):1383-1388 (1995).

Zakaria, et al., "Plasmapheresis in severe autoimmune hepatitis", *Hepatology*, 34(4):A529 (2001).

Blazar, et al., Infusion of anti B7.1 (CD80) and anti-B7.2 (CD86) monocolonal antibodies inhibits murine graft-versus-host disease lethality in part via direct effects on CD4+ and CD8+ T cells, *J. Immunology*, 157: 3250-3259 (1996).

Dau, et al., The fundamental basis for therapeutic plasmapheresis in autoimmune diseases, *Transfusion Sci.*, 17(2):235-44 (1996).

Malchesky, et al., "Are selective macromolecule removal plasmapheresis systems useful for autoimmune diseases or hyperlipidemia?", *ASAIO J.*, 39(4):868-72 (1993).

Medina, et al. "Therapeutic effect of phenantroline in two rat models of inflammatory bowel disease", *Scand J Gastroenterol.*, 36(12):1314-9 (2001).

Ou, et al., B7-H4 Ig Inhibits human beta vell destruction mediated by beta cell-specific sytotoxic T cells derived from patients with type 1 diabetes, *Diabetes*, 54(Suppl.1):A311 (2005).

Skerra, "Assembly of a functional immunoglobulin Fv fragment in *Escherichia coli*", *Science*, 240: 1038-1041 (1988).

Afzali, et al., "The role of T helper 17 (Th17) and regulatory T cells (Treg) in human organ transplantation and autoimmune disease", *Clin Exp Immunol*, 148(1):32-46 (2007).

* cited by examiner

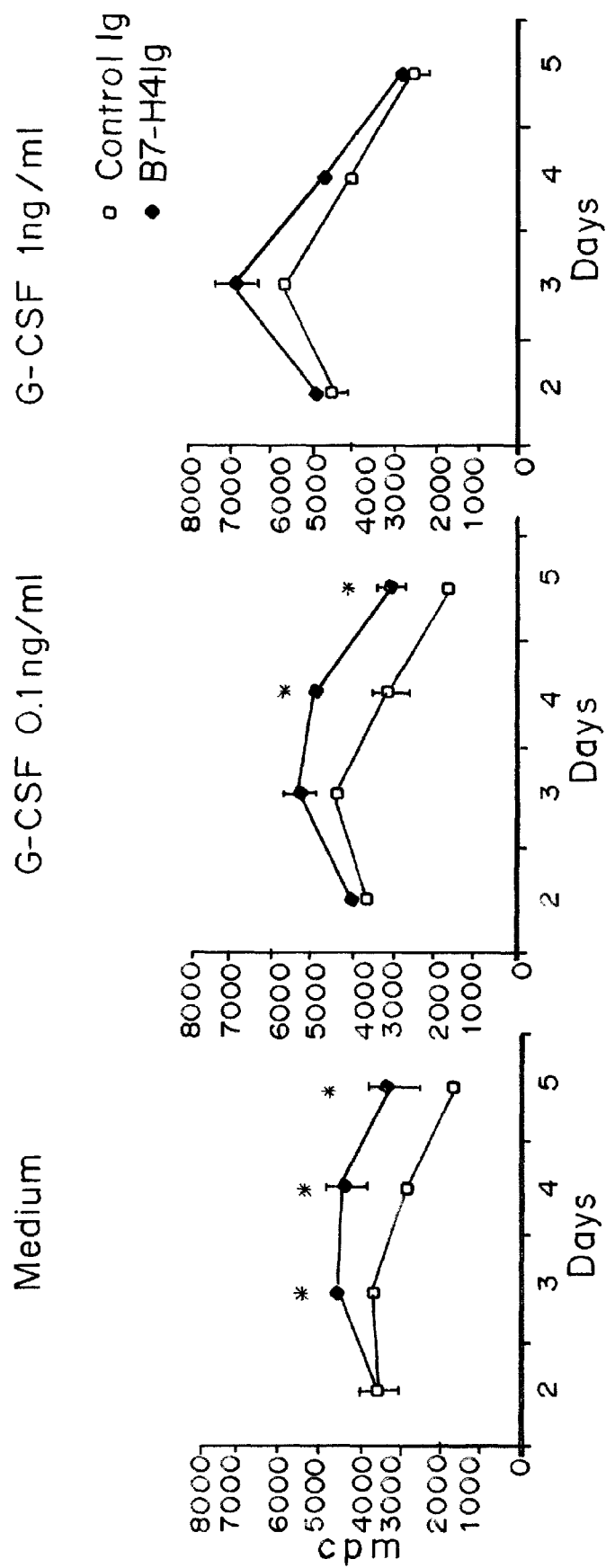

COMPOSITIONS AND METHODS FOR TREATING INFLAMMATION AND AUTO-IMMUNE DISEASES

CROSS-REFERENCE TO RELATED APPLICATIONS

This application claims benefit of and priority to U.S. Ser. No. 60/877,319 filed on Dec. 27, 2006 and U.S. Ser. No. 60/949,742 filed on Jul. 13, 2007, both of which are incorporated by reference in their entirety.

GOVERNMENT SUPPORT

This invention was made with Government support under Grant No. R01 CA98731, awarded by the National Institutes of Health. The Government has certain rights in this invention.

TECHNICAL FIELD

In general, this invention relates to compositions and methods for modulating inflammatory responses, in particular to compositions and methods for treating or inhibiting inflammatory responses related to autoimmune disorders.

BACKGROUND OF THE INVENTION

Modulating immune responses is important in the treatment of many diseases and disorders. For example, it would be advantageous to enhance an immune response in patients suffering from cancer or infection. Alternatively, it would be beneficial to inhibit or reduce an immune response in patients suffering from inflammatory conditions.

Chronic and persistent inflammation is a major cause for the pathogenesis and progression of systemic autoimmune diseases such as rheumatoid arthritis (RA) and systemic lupus erythematosus (SLE). RA is a highly inflammatory polyarthritis often leading to joint destruction, deformity and loss of function. Additive, symmetric swelling of peripheral joints is the hallmark of the disease. Extra-articular features and systemic symptoms can commonly occur and may antedate the onset of joint symptoms. Chronic pain, disability and excess mortality are unfortunate sequelae. During progression of RA, the synovial lining layer of the inflamed joints increases its thickness as a result of synovial hyperplasia and infiltration into synovial stroma by CD4+ T cells, B cells, CD8+ T cells, macrophages, dendritic cells and neutrophils (Feldmann, M. et al., *Cell*, 85:307-10 (1996); Moreland, L. W. et al., *N Engl J Med*, 337:141-7 (1997)). In SLE, the production of autoantibodies results in the deposition of immune complex in many tissues and organs including glomeruli, skin, lungs and synovium, thereby generating rheumatic lesions with characteristic chronic inflammation and tissue damage.

In several arthritis models, depletion of neutrophils resulted in a decrease of arthritis severity. The most common animal model for RA is collagen-induced arthritis (CIA) in which challenge with type II chicken collagen (CII) induces persistent chronic inflammation in all major joints of DBA/1j mice (Williams, R. O., et al., *Proc Natl Acad Sci USA*, 91:2762-6 (1994)). While CD4+ T cells have long been considered to play a central role in the pathogenesis of RA, there is renewed interest in addressing the pivotal role of neutrophils in initiation, progression and maintenance of RA. Massive infiltration of neutrophils in the lesions releases the proinflammatory cytokines including TNF-α, IL-1 and IL-6, which can affect the functions of neutrophils and other inflammatory cells.

An extensively studied murine model for SLE is the lpr strain, in which mutation of Fas apoptotic gene leads to spontaneous autoimmune disorders similar to human SLE. Studies in this strain recapitulate many aspects of human SLE symptoms. For example, lpr mice develop anti-chromatin, anti-DNA, and anti-IgG serum autoantibodies as well as a polyclonal increase of total immunoglobulin. Disease severity is highly dependent on genetic background. For example, MRL-lpr/lpr mice produce high levels of IgG autoantibodies to DNA and develop a severe glomerulonephritis due to deposition of immune complexes, while C57BL/6(B6)-lpr/lpr mice produce low level autoantibodies with much mild immunopathology.

Co-signal molecules, including those with costimulatory and coinhibitory functions, are important for the induction of effective immune response and for the prevention of unwanted autoimmunity. It has been shown that signals through the B7-CD28 family are major regulators of this balance and play a pivotal role in the regulation of autoimmunity. Persistence of inflammatory responses in systemic autoimmune diseases implies either an impaired coinhibitory or enhanced costimulatory functions, leading to the loss of the balance. In this regard, it is particularly interesting that autoantibodies against B7-H1, a primary coinhibitory molecule after binding to its receptor PD-1, is found in a significant proportion of RA patients and the presence of the autoantibodies is implicated in the progression of RA symptoms.

Soluble forms of B7-CD28 family molecules are also implicated in the progression of rheumatoid diseases. A recent study shows that soluble PD-1 could be detected in RA patients and the levels of soluble PD-1 are correlated with TNF-alpha concentration in synovial fluid. B7-H4 is a more recent addition to the B7 family member. B7-H4 has potent inhibitory effects on T cells through binding to a putative receptor. Cell surface B7-H4 is normally not detectable in normal tissues, although its surface expression could be upregulated on macrophages and tumor cells by inflammatory cytokines, including IL-10 and IL-6. It has been reported that B7-H4 could suppress T cell response in the presence of antigen stimulation. Soluble B7-H4 (sH4) has also been detected in ovarian cancer patients as a potential biomarker, but the mechanism of production and the function of sH4 is unknown. B7-H4 deficient mice were found to mount slightly enhanced T helper 1 type T cell responses against *Leishmania major* infection. Using independently generated B7-H4 knockout mice, it was demonstrated that the lack of B7-H4 led to resistance to *Listeria monocytogenes* infection occurs by direct regulation of growth of neutrophil progenitors. In summary, although B7-H4 clearly plays a role in immunity, especially autoimmunity and resistance to infection, the mechanism is not clear.

Therefore, it is object of the invention to provide compositions and methods for the treatment of autoimmune disorders.

It is another object to the invention to provide compositions and methods for the treatment of inflammatory responses.

It is still another object to provide methods and compositions for inhibiting, reducing, or blocking the biological activity of soluble B7-H4.

SUMMARY OF THE INVENTION

Compositions containing soluble B7-H4 (sH4) antagonists in an amount effective to reduce, inhibit, or mitigate an inflammatory response in an individual and methods for the treatment or prophylaxis of inflammatory disorders and autoimmune diseases or disorders have been developed. It has been discovered that soluble H4 ("sH4") interferes with B7-H4 activity, including B7-H4 inhibition of T cell immunity. Thus, interference of sH4 biological activity is believed to be an effective method to restore B7-H4 activity and thereby provide an effective method for treating inflammatory diseases or disorders, including autoimmune diseases or disorders.

Suitable sH4 antagonists include, but are not limited to, sH4 binding agents such as antibodies and natural ligands of sH4, nucleic acids encoding sH4 antagonists, protease inhibitors, B7-H4 polypeptides, B7-H4 fusion proteins, and inhibitory nucleic acids specific for sH4 encoding nucleic acids. As the results in Example 9 demonstrate, B7-H4Ig could also work as an agonist to suppress both humoral and cellular autoimmunity. Another method of treating inflammatory responses or autoimmune diseases or disorders is by administering to an individual in need thereof an agent that downregulates or inhibits expression of sH4, an agent that inactivates sH4 in vivo, an agent that competes for sH4's natural ligand in vivo, or a combination thereof.

In certain embodiments, neutrophil-mediated inflammation is reduced or inhibited. Representative inflammatory diseases or disorders that can be treated with one or more of the sH4 antagonists to reduce, inhibit or mitigate one or more symptoms include, but are not limited to, autoimmune diseases or disorders including rheumatoid arthritis, systemic lupus erythematosus, alopecia greata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia-fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

Still another method of treating a inflammatory response or autoimmune disease or disorder is by selectively removing sH4 from the blood or plasma of an individual. The blood or plasma can be treated ex vivo with a binding agent specific for sH4 to selectively remove sH4 from the blood or plasma. The treated blood or plasma can then be returned to the individual.

The severity of an inflammatory response or autoimmune disease or disorder can be assessed by determining the level of sH4 in a biological sample of an individual and correlating the level of sH4 in the sample with predetermined amounts of sH4 obtained from individual's at different time points in the progression of the disease or disorder.

BRIEF DESCRIPTION OF THE DRAWINGS

FIG. 6 is a line graph of CPM versus days. Two×10$^6$ of bone marrow cells from normal B6 mice were plated in the 96-well plates coated with 20 μg/ml of recombinant murine B7-H4Ig (□) or murine Ig control protein (▲) in the absence (A) or presence of 0.1 ng/ml (B) or 1 ng/ml (C) of recombinant murine G-CSF. Cells were harvested on day 2-5 days as indicated. The cultures were pulsed with $^3$HTdR for 18 hrs before the end of culture, harvested and counted by a scintillation counter. *P<0.05.

DETAILED DESCRIPTION OF THE INVENTION

I. Definitions

Figure 1:
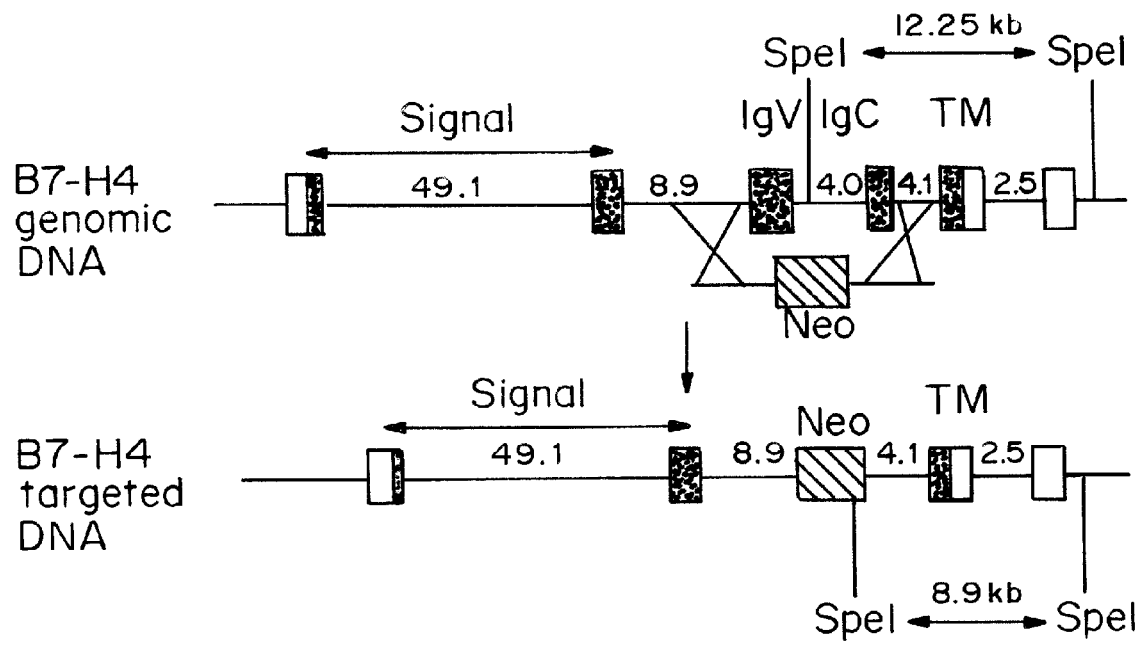
FIG. 1 is a schematic diagram showing the disruption of the B7-H4 gene. A 4.7 kb DNA fragment containing exons encoding the IgV and IgC domains of murine B7-H4 gene is substituted by a 1.7 kb fragment encoding the neomycin resistant (Neo) gene. Closed boxes represent B7-H4 coding exons. Lines between exons represent intron sequences. Open boxes represent untranslated exons. The Neo is represented by a shaded box.

Unless otherwise defined, all technical and scientific terms used herein have the same meaning as commonly understood by one of ordinary skill in the art to which this invention pertains. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "effective amount" or "therapeutically effective amount" means a dosage sufficient to provide treatment of the inflammatory response or autoimmune disease state being treated or to otherwise provide a desired pharmacologic and/or physiologic effect. The precise dosage will vary according to a variety of factors such as subject-dependent variables (e.g., age, immune system health, etc.), the disease, and the treatment being effected.

A "fragment" of a B7-H4 polypeptide is a fragment of the polypeptide that is shorter than the full-length polypeptide. Generally, fragments will be five or more amino acids in length. An antigenic fragment has the ability to be recognized and bound by an antibody.

The terms "individual," "individual," "subject," and "patient" are used interchangeably herein, and refer to a mammal, including, but not limited to, rodents, simians, humans, mammalian farm animals, mammalian sport animals, and mammalian pets.

As used herein, "operably linked" with regard to nucleic acids means incorporated into a genetic construct so that expression control sequences effectively control expression of a coding sequence of interest.

The terms "polypeptide" and "protein" are used interchangeably and mean any peptide-linked chain of amino acids, regardless of length or post-translational modification. Embodiments include B7-H4 polypeptides with conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The term "sH4" refers to soluble B7-H4 including biologically active fragments of the extracellular domain of B7-H4.

The term "soluble B7-H4 antagonist" or "sH4 antagonist" refers to compounds that inhibit, reduce, or block the biological activity or expression of soluble B7-H4. Suitable soluble B7-H4 antagonists include, but are not limited to antibodies and antibody fragments that bind soluble B7-H4, B7-H4 or fragments thereof capable of antagonizing soluble B7-H4, B7-H4 fusion proteins, protease inhibitors, small organic compounds, antisense DNA, siRNA, and microRNA specific for nucleic acids encoding sH4. As the results in Example 9 demonstrate, B7-H4Ig could work as an agonist to suppress both Example 9 demonstrate, B7-H4Ig could work as an agonist to suppress both humoral and cellular autoimmunity. In one embodiment, the soluble B7-H4 antagonist reduces or inhibits neutrophil-mediated inflammation.

As used herein, the term "treating" includes alleviating, preventing and/or eliminating one or more symptoms associated with inflammatory responses or an autoimmune disease.

II. Anti-Inflammatory Compositions

Compositions for inhibiting, reducing, or blocking the biological activity or expression of soluble B7-H4 (also referred to as "sH4") are provided. In certain embodiments, the compositions include as an active agent a sH4 antagonist in an amount effective to inhibit, reduce, or decrease an inflammatory response. An exemplary inflammatory response includes, but is not limited to, neutrophil-mediated inflammatory responses.

A. sH4 Antagonists

Soluble B7-H4 antagonists include compounds that inhibit the expression or biological activity of sH4. Soluble B7-H4 is approximately 50-kDa by Western blot analysis, a size equal to entire extracellular domain of monomeric B7-H4 molecule in denatured condition (FIG. 1b).

1. Protease Inhibitors

It is believed that sH4 is generated by enzymatic cleavage of the entire extracellular portion of B7-H4. 293T cells transfected with full length B7-H4 cDNA release sH4 into culture supernatant, and this secretion can be inhibited by incubation with various proteases inhibitors. Thus, in certain embodiments, sH4 antagonists include protease inhibitors. Exemplary protease inhibitors include, but are not limited to, serine protease inhibitors, cysteine protease inhibitors, aspartic protease inhibitors, and metalloprotease inhibitors. Specific protease inhibitors include leupeptin, PMSF, AEBSF, aprotinin, chymostatin, antithrombin III, 3,4-dichloroisocoumarin, TLCK, TPCK, DIFP, antipain, α2-macroglobulin, N-ethylmaleimide, E-64, chymostatin, pepstatin A, 1,10-phenanthroline, phosphoramidon, and bestatin.

2. Inhibitory Nucleic Acids sH4 containing only the IgV (FIG. 2a) portion of the extracellular domain is sufficient to exacerbate autoimmune diseases. In fact, B7-H4V and B7-H4VC (FIG. 2a) have similar effects in animal models, suggesting that the binding site for its putative receptor is located in the IgV domain, a result supported by a previous study using the B7-H4 IgV structure based on a computer-generated model. A previous report suggests that B7-H4 is a GPI-anchoring protein which could become the soluble form by detaching from an anchoring moiety. However, a recent study indicates that B7-H4 is a transmembrane protein. Several molecules in the immunoglobulin superfamily have been shown to display soluble forms. These soluble molecules including CD80, CD86 and PD-1 are made by splicing variants. Therefore, sH4 could be generated via alternative splicing of B7-H4.

An inhibitory nucleic acid can specifically inhibit RNA splicing that produces a transcript encoding sH4 or specifically inhibit or reduce the expression of RNA encoding sH4. Inhibitory nucleic acids include, but are not limited to, antisense DNA, triplex-forming oligonucleotides, external guide sequences, siRNA, and microRNA. Useful inhibitory nucleic acids include those that reduce the expression of RNA encoding sH4 by at least 20, 30, 40, 50, 60, 70, 80, 90 or 95 percent compared to controls. Inhibitory nucleic acids and methods of producing them are well known in the art. siRNA design software is available for example at http://i.cs.hku.hk/~sirna/software/sirna.php. Synthesis of nucleic acids is well known see for example Molecular Cloning: A Laboratory Manual (Sambrook and Russel eds. 3$^{rd}$ ed.) Cold Spring Harbor, N.Y. (2001).

3. Anti-sH4 Antibodies

Antibodies or antibody fragments that specifically bind to sH4 can be used to antagonize the biological activity of sH4. An exemplary antibody is mAb hH4.3 (Choi, I. H. et al., *J Immunol,* 171:4650-4 (2003)). Methods of producing antibodies are well known and within the ability of one of ordinary skill in the art.

For example, monoclonal antibodies (mAbs) and methods for their production and use are described in Kohler and Milstein, Nature 256:495-497 (1975); U.S. Pat. No. 4,376, 110; Hartlow, E. et al., Antibodies: A Laboratory Manual, Cold Spring Harbor Laboratory Press, Cold Spring Harbor, N.Y., 1988); Monoclonal Antibodies and Hybridomas: A New Dimension in Biological Analyses, Plenum Press, New York, N.Y. (1980); H. Zola et al., in Monoclonal Hybridoma Antibodies: Techniques and Applications, CRC Press, 1982)).

Anti-idiotypic antibodies are described, for example, in Idiotypy in Biology and Medicine, Academic Press, New York, 1984; Immunological Reviews Volume 79, 1984; Immunological Reviews Volume 90, 1986; Curr. Top. Microbiol., Immunol. Volume 119, 1985; Bona, C. et al., CRC Crit. Rev. Immunol., pp. 33-81 (1981); Jerme, N K, Ann. Immunol. 125C:373-389 (1974); Jerne, N K, In: Idiotypes—Antigens on the Inside, Westen-Schnurr, I., ed., Editiones Roche, Basel, 1982; Urbain, J. et al., Ann. Immunol. 133D:179-(1982); Rajewsky, K. et al., Ann. Rev. Immunol. 1:569-607 (1983).

Certain embodiments provide antibodies, both polyclonal and monoclonal, reactive with novel epitopes of sH4 that are absent or masked in B7-H4. The antibodies may be xenogeneic, allogeneic, syngeneic, or modified forms thereof, such as humanized, single chain or chimeric antibodies. Antibodies may also be anti-idiotypic antibodies specific for the idiotype of an anti-sH4 antibody. The term "antibody" is also meant to include both intact molecules as well as fragments thereof that include the antigen-binding site and are capable of binding to a sH4 epitope. These include Fab and F(ab')$_2$ fragments which lack the Fc fragment of an intact antibody, and therefore clear more rapidly from the circulation, and may have less non-specific tissue binding than an intact antibody (Wahl et al., *J. Nuc. Med.* 24:316-325 (1983)). Also included are Fv fragments (Hochman, J. et al., *Biochemistry,* 12:1130-1135 (1973); Sharon, J. et al., *Biochemistry,* 15:1591-1594 (1976)). These various fragments can be produced using conventional techniques such as protease cleavage or chemical cleavage (see, e.g., Rousseaux et al., *Meth. Enzymol.,* 121:663-69 (1986)).

Polyclonal antibodies are obtained as sera from immunized animals such as rabbits, goats, rodents, etc. and may be used directly without further treatment or may be subjected to conventional enrichment or purification methods such as ammonium sulfate precipitation, ion exchange chromatography, and affinity chromatography.

The immunogen may be any immunogenic portion of sH4. Preferred immunogens include all or a part of the extracellular domain of human B7-H4, where these residues contain the post-translation modifications, such as glycosylation, found on the native B7-H4. Immunogens including the extracellular domain are produced in a variety of ways known in the art, e.g., expression of cloned genes using conventional recombinant methods, isolation from cells of origin, cell populations expressing high levels of B7-H4.

The mabs may be produced using conventional hybridoma technology, such as the procedures introduced by Kohler and Milstein, *Nature,* 256:495-97 (1975), and modifications thereof (see above references). An animal, preferably a mouse is primed by immunization with an immunogen as above to elicit the desired antibody response in the primed animal.

B lymphocytes from the lymph nodes, spleens or peripheral blood of a primed, animal are fused with myeloma cells, generally in the presence of a fusion promoting agent such as polyethylene glycol (PEG). Any of a number of murine myeloma cell lines are available for such use: the P3-NS1/1-Ag4-1, P3-x63-k0Ag8.653, Sp2/0-Ag14, or HL1-653 myeloma lines (available from the ATCC, Rockville, Md.). Subsequent steps include growth in selective medium so that unfused parental myeloma cells and donor lymphocyte cells eventually die while only the hybridoma cells survive. These are cloned and grown and their supernatants screened for the presence of antibody of the desired specificity, e.g. by immunoassay techniques using the B7-H4-Ig fusion protein. Positive clones are subcloned, e.g., by limiting dilution, and the mAbs are isolated.

Hybridomas produced according to these methods can be propagated in vitro or in vivo (in ascites fluid) using techniques known in the art (see generally Fink et al., *Prog. Clin. Pathol.,* 9:121-33 (1984)). Generally, the individual cell line is propagated in culture and the culture medium containing high concentrations of a single mAb can be harvested by decantation, filtration, or centrifugation.

The antibody may be produced as a single chain antibody or scfv instead of the normal multimeric structure. Single chain antibodies include the hypervariable regions from an Ig of interest and recreate the antigen binding site of the native Ig while being a fraction of the size of the intact Ig (Skerra, A. et al., *Science,* 240: 1038-1041 (1988); Pluckthun, A. et al., *Methods Enzymol.,* 178: 497-515 (1989); Winter, G. et al. *Nature,* 349; 293-299 (1991); Bird et al., *Science* 242:423 (1988); Huston et al. *Proc. Natl. Acad Sci. USA* 85:5879 (1988); Jost C R et al. *J Biol Chem* 269:26267-26273 (1994); U.S. Pat. Nos. 4,704,692, 4,853,871, 4,94,6778, 5,260,203. In a preferred embodiment, the antibody is produced using conventional molecular biology techniques.

Methods of using the antibodies to detect the presence of the epitope are described in Coligan, J. E. et al., eds., Current Protocols in Immunology, Wiley-Interscience, New York 1991 (or current edition); Butt, W. R. (ed.) Practical Immunoassay The State of the Art, Dekker, N.Y., 1984; Bizollon, Ch. A., ed., Monoclonal Antibodies and New Trends in Immunoassays, Elsevier, N.Y., 1984; Butler, J. E., ELISA (Chapter 29), In: van Oss, C. J. et al., (eds), IMMUNOCHEMISTRY, Marcel Dekker, Inc., New York, 1994, pp. 759-803; Butler, J. E. (ed.), Immunochemistry of Solid-Phase Immunoassay, CRC Press, Boca Raton, 1991; Weintraub, B., Principles of Radioimmunoassays, Seventh Training Course on Radioligand Assay Techniques, The Endocrine Society, March, 1986; Work, T. S. et al., Laboratory Techniques and Biochemistry in Molecular Biology, North Holland Publishing Company, NY, (1978) (Chapter by Chard, T., "An Introduction to Radioimmune Assay and Related Techniques").

B. B7-H4 Fusion Proteins

B7-H4 fusion polypeptides have a first fusion partner including all or a part of a B7-H4 protein fused (i) directly to a second polypeptide or, (ii) optionally, fused to a linker peptide sequence that is fused to the second polypeptide. An exemplary fusion protein is described in Sica, G. L. et al. B7-H4, a molecule of the B7 family, negatively regulates T cell immunity. *Immunity* 18, 849-61 (2003).

The B7-H4 fusion protein may be fused to a second polypeptide, preferably one or more domains of an Ig heavy chain constant region, preferably having an amino acid sequence corresponding to the hinge, $C_{H2}$ and $C_{H3}$ regions of a human immunoglobulin Cγ1 chain.

The B7-H4 fusion proteins can include full-length B7-H4 polypeptides, or can contain a fragment of a full length B7-H4 polypeptide. In one embodiment, the fusion protein contains a fragment of B7-H4. As used herein, a fragment of B7-H4 refers to any subset of the polypeptide that is a shorter polypeptide of the full length protein. Useful fragments are those that retain the ability to bind to their natural ligands. A B7-H4 polypeptide that is a fragment of full-length B7-H4 typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural ligand(s) as compared to full-length B7-H4.

One embodiment provides a fusion protein in which the first fusion partner is the extracellular domain of a B7-H4 protein. B7-H4 nucleotide and protein sequence are found in GENBANK under accession number AY280972. Additionally, B7-H4 is described in U.S. Pat. No. 6,891,030 and where permissible, is incorporated by reference in its entirety. The fusion protein can contain the entire extracellular domain of B7-H4 or a fragment thereof that retains biological activity of B7-H4.

The first fusion partner of the fusion protein includes the membrane distal IgV domain and the membrane proximal IgC domain of B7-H4. The construct can have at least 80%, 85%, 90%, 95%, or 99% sequence identity to: maslgqiifw siiniiiila gaiaiiigfg isgkhfitvt tftsagnige dgtlsctfep diklngiviq wikegikglv hefkegkddl sqqhemfrgr tavfadqvvv gnaslrlknv qltdagtytc yirtskgkgn anleyktgaf smpeinvdyn asseslrcea prwfpqptva wasqvdqgan fsevsntsfe lnsenvtmkv vsvlynvtin ntyscmiend iakatgdikv tdsevkrrsq lqllns (SEQ ID NO:1) also referred to as B7-H4VC.

In another embodiment, the first fusion partner of the fusion protein includes the IgV domain of B7-H4. The construct can have at least 80%, 85%, 90%, 95%, or 99% sequence identity to:
maslgqiifw siiniiiila gaialiigfg isgkhfitvt tftsagnige dgtlsctfep diklngiviq wlkegikglv hefkegkddl sqqhemfrgr tavfadqvvv gnaslrlknv qltdagtytc yirtskgkgn anleyktgaf smpein (SEQ ID NO:2) also referred to as B7-H4V.

In a preferred embodiment, the fusion protein includes the extracellular domain of B7-H4 or fragment thereof fused to an Ig Fc constant region. Recombinant B7-H4Ig fusion protein can be prepared by fusing the coding region of the extracellular domain of B7-H4 to the Fc constant region of mouse IgG2a as described previously (Chapoval et al. *Methods Mol. Med.* 45:247-255 (2000)).

The disclosed fusion proteins can be isolated using standard molecular biology techniques. For example, an expression vector containing a DNA sequence encoding B7-H4Ig is transfected into 293 cells by calcium phosphate precipitation and cultured in serum-free DMEM. The supernatant is collected at 72 h and the fusion protein is purified by Protein G SEPHAROSE® columns (Pharmacia, Uppsala, Sweden).

Variants of B7-H4 can also be used to produce a fusion protein that reduces, inhibits or blocks the biological function of sH4. As used herein, a "variant" B7-H4 polypeptide contains at least one amino acid sequence alteration as compared to the amino acid sequence of the corresponding wild-type B7-H4 polypeptide (e.g., a polypeptide having the amino acid sequence set forth in Accession No. AY280972). An amino acid sequence alteration can be, for example, a substitution, a deletion, or an insertion of one or more amino acids.

Variants of B7-H4 can have the same activity, substantially the same activity, or different activity than wildtype B7-H4. Substantially the same activity means that the variant is able to suppress T cell activation.

It will be appreciated that variants of the extracellular domain of B7-H4 can have at least 80% sequence identity with the extracellular domain of wild-type B7-H4 (i.e., Accession No. AY280972), typically at least 85%, more typically, at least 90%, even more typically, at least 95% sequence identity to the extracellular domain of B7-H4. In one embodiment, the fusion protein includes the extracellular domain of B7-H4 that is identical to the extracellular domain of B7-H4 in Accession No. AY280972.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch *J. Mol. Biol.*, 48:443-453 (1970); 2) BLOSSUM62 comparison matrix from Hentikoff and Hentikoff *Proc. Natl. Acad. Sci. USA.*, 89:10915-10919 (1992); 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps).

Alternatively, polypeptide sequence identity can be calculated using the following equation: % identity=(the number of identical residues)/(alignment length in amino acid residues)*100. For this calculation, alignment length includes internal gaps but does not include terminal gaps.

Amino acid substitutions can be made using any amino acid or amino acid analog. For example, substitutions can be made with any of the naturally-occurring amino acids (e.g., alanine, aspartic acid, asparagine, arginine, cysteine, glycine, glutamic acid, glutamine, histidine, leucine, valine, isoleucine, lysine, methionine, proline, threonine, serine, phenylalanine, tryptophan, or tyrosine).

Amino acid substitutions in B7-H4 fusion proteins polypeptides may be conservative substitutions. As used herein, "conservative" amino acid substitutions are substitutions wherein the substituted amino acid has similar structural or chemical properties. "Non-conservative" amino acid substitutions are those in which the charge, hydrophobicity, or bulk of the substituted amino acid is significantly altered. Non-conservative substitutions will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The disclosed fusion proteins and variants thereof preferably compete with sH4 to inhibit the biological activity of sH4, for example by binding to a common receptor. The receptor is typically a receptor on an immune cell that binds both sH4 and B7-H4. The variants of the extracellular domain of B7-H4 include conservative variants and non-conservative variants that increase the ability to of the fusion protein to compete with sH4 and thereby reduce the biological activity of sH4.

Also provided is a dimeric or trimeric fusion protein which is a dimer or trimer of the above fusion proteins. Preferably, the chains are tandemly linked via disulfide bonds or other interchain covalent bonds.

In a preferred dimeric fusion protein, the dimer results from the covalent bonding of Cys residue in the CH regions of two of the Ig heavy chains that are the same Cys residues that are disulfide linked in dimerized normal Ig H chains.

Suitable fusion proteins may include a multimer of two or more repeats of the first fusion partner linked end to end, directly or with a linker sequence between one or more monomers.

C. Pharmaceutical Compositions

Pharmaceutical compositions including sH4 antagonists, and vectors containing the same are provided. The pharmaceutical compositions may be for administration by oral, parenteral (intramuscular, intraperitoneal, intravenous (IV) or subcutaneous injection), transdermal (either passively or using iontophoresis or electroporation), transmucosal (nasal, vaginal, rectal, or sublingual) routes of administration or using bioerodible inserts and can be formulated in dosage forms appropriate for each route of administration.

1. Formulations for Parenteral Administration

In a preferred embodiment, the peptides are administered in an aqueous solution, by parenteral injection. The formulation may also be in the form of a suspension or emulsion. In general, pharmaceutical compositions are provided including effective amounts of a sH4 antagonist, or derivative products, and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN 20, TWEEN 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Enteral Administration sH4 antagonists can be formulated for oral delivery. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The polypeptide antagonists may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) J. Appl. Biochem. 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The sH4 antagonists can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e. the drug is enclosed in a semipermeable membrane which allows water to enter and push drug out through a single small opening due to osmotic effects. For oral formulations, the location of release may be the stomach, the small intestine (the duodenum, the jejunem, or the ileum), or the large intestine. Preferably, the release will avoid the deleterious effects of the stomach environment, either by protection of the peptide (or derivative) or by release of the peptide (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

3. Topical Delivery Formulations

Compositions can be applied topically. This does not work well for most peptide formulations, although it can be effective especially if applied to the lungs, nasal, oral (sublingual buccal), vaginal, or rectal mucosa. The sH4 antagonists can be delivered to the lungs while inhaling and traverses across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, sprays, or patches, all of which can be prepared using standard technology. Transdermal formulations will require the inclusion of penetration enhancers.

4. Controlled Delivery Polymeric Matrices

Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of sH4 antagonists, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release 5, 13-22 (1987); Mathiowitz, et al., Reactive Polymers 6, 275-283 (1987); and Mathiowitz, et al., J. Appl. Polymer Sci. 35, 755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods of Manufacture

As discussed above and in the examples, polypeptide sH4 antagonists, nucleic acid constructs encoding sH4 antagonists, B7-H4 or variants thereof can be produced using standard molecular biology protocols known in the art. See for example, Molecular Cloning: A Laboratory Manual (Sambrook and Russel eds. $3^{rd}$ ed.) Cold Spring Harbor, N.Y. (2001). Alternatively, B7-H4, sH4, antagonists or agonists thereof, or variants there of can be isolated and purified from an individual expressing them using conventional biochemical techniques.

IV. Inflammatory Response Treatment and Detection

A. Diagnostics

Soluble B7-H4 is found in sera of approximately two-thirds of the RA and one-third of the SLE patients sampled and the concentration of sH4 correlates closely with the severity of RA. In an experimental model of RA and SLE, the effect of sH4 was recapitulated, and it was demonstrated that sH4 acts as a decoy to block suppressive functions of endogenous B7-H4, leading to exacerbation of systemic autoimmune diseases (see Examples). The results demonstrate a role of sH4 in the pathogenesis of systemic autoimmune diseases.

An inflammatory response in an individual can be detected by quantifying the amount of sH4 in a biological sample of the individual, wherein an elevated amount of sH4 in the individual's biological sample compared to a control (single or more preferably pooled or averaged values of normal individuals in same assay) is indicative of an inflammatory response. A biological sample includes tissue or biological fluid such as a fluid from the individual, for example, blood, plasma, saliva, lymph, cerebrospinal fluid, or sputum. A control refers to a biological sample from an individual not experiencing an inflammatory response such as an autoimmune disease.

The amount of sH4 in a sample can be determined using conventional techniques such as enzyme-linked immunosorbent assays, mass spectrometry, spectrophotometry, or a combination thereof.

The severity of an inflammatory response or an autoimmune disease can be detected or assessed by quantifying the level of sH4 in an individual's biological sample and correlating the amount of sH4 in the individual's biological sample with amount(s) of sH4 indicative of different stages of an inflammatory response or autoimmune disease. The amounts of sH4 with different stages of inflammatory disease or different levels of severity can be predetermined by quantifying sH4 in patients at different stages of inflammatory disease, or with different severity of disease. For example, with RA the following classification for severity is typically employed: Class I: No restriction of ability to perform normal activities; Class II: Moderate restriction, but with an ability to perform most activities of daily living; Class III: Marked restriction, with an inability to perform most activities of daily living and occupation; and Class IV: Incapacitation with confinement to bed or wheelchair. Levels of sH4 can be determined in patients from each classification to produce a reference level of sH4 that can be correlated with the specific severity level.

Alternatively, the amount of sH4 can be correlated to levels of neutrophils. In individuals with inflammatory responses or autoimmune disease, sH4 is elevated as are levels of neutrophils. Thus, sH4 levels in an individual can be predictive of neutrophil levels.

Representative inflammatory responses or autoimmune diseases that can be detected or assessed for severity include, but are not limited to, rheumatoid arthritis, systemic lupus erythematosus, alopecia greata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

B. Methods of Treating Inflammatory Responses

Chronic and persistent inflammation is a major cause of the pathogenesis and progression of systemic autoimmune diseases such as rheumatoid arthritis (RA) and systemic lupus erythematosus (SLE). sH4 acts as a decoy molecule to block endogenous B7-H4. B7-H4 inhibits cell cycle progression of T cells in the presence of antigen stimulation. B7-H4 can inhibit innate immunity by suppressing proliferation of neutrophil progenitors. It is believed that elevated levels of sH4 block the inhibitory effect of endogenous B7-H4.

Therefore, an inflammatory response can be treated by interfering with the biological activity of sH4 in vivo, for example, by administering to an individual in need thereof an effective amount of a sH4 antagonist to inhibit or decrease one or more symptoms of the disease, which may be indicated by a decrease in neutrophil levels. Interference of sH4 biological activity can be accomplished by down regulating expression of sH4, removing sH4, conjugating sH4 with a binding agent in vivo, for example an antibody, increasing the endogenous levels of B7-H4, administering B7-H4 fusion proteins, or a combination thereof.

1. Down-Regulation of sH4 Expression

One method for treating a inflammatory response or autoimmune disease is by administering to an individual in need thereof an mount of inhibitory nucleic acid specific for a nucleic acid encoding sH4 effective to reduce or inhibit the inflammatory response. The inhibitory nucleic acid can be antisense DNA, siRNA, microRNA, or a combination thereof. Alternatively, the inhibitory nucleic acid can be specific for a protease that cleaves B7-H4 to produce sH4. In a preferred embodiment, the inhibitory nucleic acid downregulates sH4 expression without having a statistically significant effect on B7-H4 expression. In certain aspects, the downregulation of sH4 causes a decrease in the neutrophil population.

2. Removal of sH4

Another method for treating an inflammatory response or autoimmune disorder in an individual is by removing sH4 from an individual's blood or plasma. Soluble B7-H4 can be removed using well known techniques such as ultrapheresis, apheresis, or dialysis. In one embodiment, blood or plasma is removed from an individual. Soluble B7-H4 is selectively removed from the blood or plasma ex vivo. Selective removal of sH4 can be achieved using filters having specific molecular weight cutoffs that allow sH4 to pass while other components are retained.

Alternatively, the blood or plasma can be contacted with binding agents specific for sH4. The binding agents can be immobilized on a substrate. Suitable binding agents include, but are not limited to antibodies or antigen-binding antibody fragments specific for sH4 or natural ligands of sH4. The binding agents specifically bind sH4 and capture the sH4, thereby removing it from the blood or plasma. The treated blood or plasma is then returned to the individual.

3. Inactivation of sH4

Another method for treating an inflammatory response or autoimmune disease is by administering to an individual in need thereof, a sH4 binding agent in an amount effective to reduce or inhibit the inflammatory response. A representative binding agent includes, but is not limited to an antibody or antigen-binding fragment thereof that inhibits or reduces a biological activity of sH4. A representative antibody is mAb hH4.3. It will be appreciated that small molecules can be used to bind and inactive sH4 in vivo.

4. Over-Expression of B7-H4

Over-expression of B7-H4 can be used to compete with endogenous sH4 and can therefore be an effective means for treating inflammatory responses and autoimmune diseases or disorders. Overexpression of B7-H4 can be accomplished by stimulating endogenous B7-H4 to increase expression. Alternatively, B7-H4 can be administered as a bolus to an individual in need thereof to temporarily increase serum levels of B7-H4.

Another method for treating an inflammatory response or autoimmune disease is by administering to an individual in need thereof a nucleic acid construct encoding B7-H4, or a functional fragment thereof. Functional fragment means a B7-H4 fragment that interferes with, inhibits or reduces sH4 biological activity.

In another embodiment, B7-H4 fusion protein can be administered to an individual in need thereof in an amount effective to reduce or inhibit sH4-mediated inflammation or a symptom thereof. The B7-H4 fusion proteins are discussed above. Alternatively, a nucleic acid construct encoding the B7-H4 fusion can be administered to an individual in need thereof wherein the nucleic acid construct is expressed in the individual and produces B7-H4 fusion protein in amounts effective to reduce or inhibit sH4 biological function.

5. Gene Delivery

Nucleic acids encoding sH4 antagonists can be administered to an individual in need thereof in an amount effective to treat an inflammatory response or autoimmune disease. DNA delivery involves introduction of a "foreign" DNA into a cell and ultimately, into a live animal. Gene delivery can be achieved using viral vectors or non-viral vectors. One approach includes nucleic acid transfer into primary cells in culture followed by autologous transplantation of the ex vivo transformed cells into the individual, either systemically or into a particular organ or tissue.

Nucleic acid therapy can be accomplished by direct transfer of a functionally active DNA into mammalian somatic tissue or organ in vivo. DNA transfer can be achieved using a number of approaches described below. These systems can be tested for successful expression in vitro by use of a selectable marker (e.g., G418 resistance) to select transfected clones expressing the DNA, followed by detection of the presence of the B7-H4 expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

Retroviral-mediated human therapy utilizes amphotrophic, replication-deficient retrovirus systems (Weiss and Taylor, *Cell*, 82:531-533 (1995)). Such vectors have been used to introduce functional DNA into human cells or tissues, for example, the adenosine deaminase gene into lymphocytes, the NPT-II gene and the gene for tumor necrosis factor into tumor infiltrating lymphocytes. Retrovirus-mediated gene delivery generally requires target cell proliferation for gene transfer (Bordignon et al. *Science* 270:470-475 (1995)). This condition is met by certain of the preferred target cells into which the present DNA molecules are to be introduced, i.e., actively growing tumor cells. Gene therapy of cystic fibrosis using transfection by plasmids using any of a number of methods and by retroviral vectors has been described by Collins et al., U.S. Pat. No. 5,240,846.

The DNA molecules encoding the B7-H4 polypeptides or fusion proteins may be packaged into retrovirus vectors using packaging cell lines that produce replication-defective retroviruses, as is well-known in the art (see, for example Stone, D. et al. *J. Endocrinology*, 164:103-118 (2000)). Additional viruses for gene delivery are described in Reynolds et al. Molecular Medicine Today, 5:25-31 (1999)).

Other virus vectors may also be used, including recombinant adenoviruses (Murphy et al. *Proc Natl Acad Scii* 94:13921-13926 (1997)), herpes simplex virus (HSV) for neuron-specific delivery and persistence (Lowenstein et al. Brain Res. Molec. Brain Res, 30:169-175 (1995)). Advantages of adenovirus vectors for human gene therapy include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human therapy (Samulski, R. J. et al., EMBO J. 10:3941 (1991).

Another vector which can express the disclosed DNA molecule and is useful in the present therapeutic setting, particularly in humans, is vaccinia virus, which can be rendered non-replicating (Peplinkski, G. R. et al. Surgical Oncology Clinics of North America, 7575-588 1998)). Descriptions of recombinant vaccinia viruses and other viruses containing heterologous DNA and their uses in immunization and DNA therapy are reviewed in: Moss, B., Curr. Opin. Genet. Dev. 3:86-90 (1993); Moss, B. Biotechnology 20: 345-362 (1992); Moss, B., Curr Top Microbiol Immunol 158:25-38 (1992); Moss, B., Science 252:1662-1667 (1991); Piccini, A et al., Adv. Virus Res. 34:43-64 (1988); Moss, B. et al., Gene Amplif Anal 3:201-213 (1983).

In addition to naked DNA or RNA, or viral vectors, engineered bacteria may be used as vectors. A number of bacterial strains including Salmonella, BCG and Listeria monocytogenes (LM) (Hoiseth & Stocker, Nature 291, 238-239 (1981); Poirier, T P et al. J. Exp. Med. 168, 25-32 (1988); (Sadoff, J. C., et al., Science 240, 336-338 (1988); Stover, C. K., et al., Nature 351, 456-460 (1991); Aldovini, A. et al., Nature 351, 479-482 (1991); Schafer, R., et al., J. Immunol. 149, 53-59 (1992); Ikonomidis, G. et al., J. Exp. Med. 180, 2209-2218 (1994)). These organisms display two promising characteristics for use as vaccine vectors: (1) enteric routes of infection, providing the possibility of oral vaccine delivery; and (2) infection of monocytes/macrophages thereby targeting antigens to professional APCs.

In addition to virus-mediated gene transfer in vivo, physical means well-known in the art can be used for direct transfer of DNA, including administration of plasmid DNA (Wolff et al., Science, 247:1465-1468 (1990); Hickman, M. A, et al. Hum. Gene Ther., 5:1477-1483 (1994)) and particle-bombardment mediated gene transfer (O'Brien, J. et al. Brain Res Brain Res Protco, 10:12-15 (2002)). Furthermore, electroporation, a well-known means to transfer genes into cell in vitro, can be used to transfer DNA molecules to tissues in vivo (Titomirov, A. V. et al., Biochim. Biophys. Acta 1088:131 ((1991)).

"Carrier mediated gene transfer" has also been described (Wu, C. H. et al., J. Biol. Chem. 264:16985 (1989); Wu, G. Y. et al., J. Biol. Chem. 263:14621 (1988); Soriano, P. et al., Proc. Natl. Acad. Sci. USA 80:7128 (1983); Wang, C-Y. et al., Proc. Natl. Acad. Sci. USA 84:7851 (1982); Wilson, J. M. et al., J. Biol. Chem. 267:963 (1992)). Preferred carriers are targeted liposomes (Liu et al. Curr Med Chem, 10: 13077-1315 (2003)) such as immunoliposomes, which can incorporate acylated mAbs into the lipid bilayer. Polycations such as asialoglycoprotein/polylysine (Wu et al., 1989, supra) may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA for transfer.

Plasmid DNA used for transfection or microinjection may be prepared using methods well-known in the art, for example using the Quiagen procedure (Quiagen), followed by DNA purification using known methods, such as the methods exemplified herein.

6. Combination Therapy

The disclosed compositions can be administered to a subject in need thereof alone or in combination with one or more additional therapeutic agents including, but not limited to immunosuppressive agents, e.g., antibodies against other lymphocyte surface markers (e.g., CD40) or against cytokines, other fusion proteins, e.g., CTLA41g, or other immunosuppressive drugs (e.g., cyclosporin A, FK506-like compounds, rapamycin compounds, or steroids), anti-proliferatives, cytotoxic agents, or other compounds that may assist in immunosuppression.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art (See, e.g. WO 95122972, WO 95116691, WO 95104738, U.S. Pat. Nos. 6,015,809; 5,989,591; U.S. Pat. Nos. 5,567,709; 5,559,112; 5,530,006; 5,484,790; 5,385,908; 5,202,332; 5,162,333; 5,780,462; 5,120,727).

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506-like compounds include, for example, those described in WO 00101385. Preferably, the language "rapamycin compound" as used herein does not include FK506-like compounds.

Other suitable therapeutics include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (flupred-nylidene) acetate, flurandrenolone, halcinonide, hydrocortisone acetate, hydrocortisone butyrate, methylprednisolone, triamcinolone acetonide, cortisone, cortodoxone, flucetonide, fludrocorisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluorometholone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

V. Transgenic Animals

Transgenic non-human animals that do not express B7-H4 or have reduced expression are useful in screening and testing. The endogenous B7-H4 gene and alleles can be disrupted by inserting a genetic element into the gene to prevent expression. Preferably, the endogenous B7-H4 gene is deleted using homologous recombination. Representative non-human transgenic animals include mice or other rodents, sheep, goats, cows, pigs, and non-human primates.

The transgenic animals can be used to as research tools to study how B7-H4 modulates the immune system, in particular how B7-H4 suppresses immune responses. For example, the transgenic animals can be used to screen for compounds that mimic endogenous B7-H4 biological activity or for compounds that interact with soluble B7-H4.

The present invention will be further understood by reference to the following non-limiting examples.

EXAMPLES

Example 1

Generation of B7-H4KO Mice

Mice 6-8-week-old C57BL16 (B6) mice were obtained from the Jackson Laboratory. RAG-1 KO mice were purchased from Taconic Farms. Both female and male mice were used for the experiments. All mice were housed under specific pathogen-free conditions in the Johns Hopkins Animal Facility with all protocols approved by the Institutional Animal Care and Use Committee. The general strategy to generate gene KO mice by homologous recombination was described by Dong, H. et al., *Immunity* 20:327-336 (2004); Tamada, K. et al., *J Immunol.*, 168, 4832-4835 (2002). To generate B7-H4 KO mice, a 5.09 kb DNA fragment upstream of the IgV domain (exon 3) of the murine B7-H4 genomic DNA was PCR amplified from a 129SvJ bacterial artificial chromosome (BAC) library (Invitrogen, Carlsbad, Calif.) and was cloned into the 5'-arm position of the pKOscrambler vector NTKV-1907 (Stratagene, La Jolla, Calif.). A 5.57 kb DNA fragment downstream of the IgC domain (exon 4) of B7-H4 genomic DNA was PCR amplified from the same library and was cloned into the 3'-arm position of the same vector to generate a targeting plasmid, resulting in removing IgV and IgC domains from the B7-H4 gene (FIG. 1A). The targeting fragment containing the 5'-arm and the 3'-arm sequences of the B7-H4 gene, a positive selection marker NEO, and a negative selection marker TK was transfected into 129SvIE embryonic stem (ES) cells. ES cell transfectants underwent neomycin drug selection. The targeted clones were identified by Southern blot analysis using a 3' external probe. Chimeric mice were produced by injection of targeted ES cells into blastocysts of B6 individuals. Heterozygous B7-H4 (+I−) mice were obtained from breeding chimeric mice with B6 mice. PCR analysis was employed to distinguish the wildtype and deficient B7-H4 allele. The sequences of the three PCR primers are: (1) 5'-GTTAGATAGGGTCTCACTGGGTAGC (SEQ ID NO:3), (2) 5'-CCTACAGCCTTCAGTATGCCAGAGA (SEQ ID NO:4), (3) 5'-AGACTAGTGAGACGTGCTACTTCCA (SEQ ID NO:5). Homozygous mice were produced by backcrossing to B6 for more than ten generations before use for further analysis. B7-H4 KO/RAG-1 KO mice were obtained by backcrossing B7-H4 KO and RG-1 KO mice.

B7-H4KO mice were generated by homologous recombination in 129 ES cells by deleting the entire Ig V and Ig C regions of the B7-H4 gene to completely eliminate their interaction with its potential receptor. Exons encoding both the Ig V and Ig C domains of B7-H4 gene were replaced with a Neo gene cassette (FIG. 1). Targeted recombination of ES cells was confirmed by Southern blot analysis and the data from 4 independent ES clones is shown. B7-H4+ allele is predicted to have a 12.25 kb Spe1 fragment and B7-H4-allele has an 8.9 kb Spe1 fragment. The clones (2 and 3) with both fragments indicate a recombination. Chimeric male mice were derived from these ES clones by standard procedures. They were backcrossed to C57BL16 (B6) females and heterozygous mutant mice were established from two independently targeted ES clones. Heterozygous or homozygous B7-H4 mutant mice were then identified by PCR analysis of genomic DNA isolated from tail biopsies. Southern blot analysis confirmed the replacement of genomic DNA. RT-PCR analysis demonstrated B7-H4 mRNA was not expressed in livers of B7-H4-deficient mice. B7-H4KO mice develop normally and give normal litter numbers. These mice were backcrossed to the B6 background for 10 generations before they were used in studies described below.

Example 2

B7-H4KO Mice have Enhanced Granulocyte-Mediated Resistance to *Listeria* Infection Antibodies, Recombinant Protein and Flow Cytometry Analysis Primary and secondary antibodies against murine Gr-1 and CD11b, which are directly conjugated with FITC, PE, or APC, were purchased from BD Pharmingen (San Diego, Calif.) or eBiosciences (San Diego, Calif.). Non-conjugated primary antibodies were purified from hybridoma culture supernatant. B7-H4Ig fusion protein was prepared as described by Sica, G. L. et al., *Immunity*, 18:849-861 (2003). All cells were stained using standard protocols as previously described and were analyzed on a FACSCalibur flow cytometry (id). The data was analyzed with Software CellQuest (BD) or FlowJo (Tree Star, Inc., Ashland, Oreg.). For in vivo studies, mAbs were prepared and purified as previously described (id). Anti-NK1.1 hybridoma (PK136) and anti-IFN-γ hybridoma (R4-6A2) were purchased from ATCC. Anti-Gr-1 hybridoma (RB6-8C5) was a generous gift from Dr. Hans Schreiber in University of Chicago. Control mouse IgG, rat IgG, and hamster IgG were purchased from Sigma (St. Louis, Mo.) and further purified as previously described (id). Carrageenan was purchased from Sigma. All cell culture media and antibiotics were purchased from Cellgro (Herndon, Va.). Fetal bovine serum (FBS) was from Hyclone (Logan, Utah).

*Listeria* Infection and Colony Counting

*Listeria monocytogenes* strain DP-L4056 was kindly provided by Dr. Thomas W. Dubensky Jr. from Cerus Corp. To prepare *Listeria* stock, *Listeria* cells were grown in DIFCO *Listeria* Enrichment Broth (Becton Dickinson Co., Sparks, Md.) to 0.8-1 at OD600 nm. Culture was harvested by centrifugation and was washed twice with PBS. Pellets were then re-suspended in stock solution (PBS with 15-20% glycerol) and aliquoted to 200 μl per microtube for storage at −80° C. The colony-forming units (CFU) of *Listeria* stock were determined by counting colonies of series dilutions of the aliquots growing on BBL CHROMagar *Listeria* plates (Becton Dickinson Co., Sparks, Md.). Prior to infection, *Listeria* stock was thawed and diluted in PBS to appropriate concentration of CFU/ml and applied to mice or cells as indicated. Mice 6-8 weeks old were infected by intraperitoneal (i.p.) or intravenous (i.v.) injection of indicated CFU of *Listeria*. At indicated time points post-infection, a piece of mouse liver or spleen was cut, weighed, and ground in PBS. The liver suspension was plated on BBL CHROMagar *Listeria* plates or on agar plates of *Listeria* Enrichment Broth. Colonies were counted 2 days post plating, and adjusted to CFU/g of liver or spleen.

*Listeria* Infection of Granulocytes In Vitro.

Granulocytes were isolated similar to the methods described by Chen, L. Y. et al., *Hum. Mol Genet.*, 12.2547-2558 (2003). Briefly, mice were injected i.p. with 3% thioglycollate broth. Four to five hours post injection, peritoneal cavities of each mouse were washed with 5 ml PBS and cells were harvested by centrifugation. By this method, more than 90% harvested cells are Gr-$1^+$CD11b+ granulocyte. $1 \times 10^6$ granulocytes were incubated with $1 \times 10^8$ CFU of LM for 10 min at 37° C. The cultures were terminated by adding Penicillin-Streptomycin (Cellgro). Subsequently, cells were harvested by centrifugation, plated in 96-well plates. The plates were incubated at 37° C. and harvested at indicated time points. Cells were lysed immediately by resuspending in 1 ml of sterile water. Cell lysates or diluted cell lysates were plated on agar plates of *Listeria* Enrichment Broth for colony counting.

Respiratory Burst and Phagocytosis of Granulocytes.

Granulocyte phagocytic activity and oxidative burst activity were measured as described by Radsak, M. P., et al., *J. Immunol.*, 172:4956-4963 (2004); Radsak, M. P. et al, *Blood*, 101:2810-281 5 (2003). Briefly, $1 \times 10^6$ granulocytes were incubated with $5 \times 10^7$ of red-fluorescent micro-beads (FLUORESBRITE® Polychromatic Red 1.0 Micron Microspheres, Polysciences, Inc. Warrington, Pa.) and 25 µM of DCFH-DA (2',7'-dihydrochlorofluoresein diacetate, Sigma-Aldrich) for 30-60 min at 37° C. Cells were washed twice with FACS buffer (1% FBS in PBS) and fixed in 1% paraformaldehyde in PBS. Analysis was performed by flow cytometry.

Pathology

The method for tissue processing and staining was described by Dong, H. et al, *Nature Med.* 8:793-800 (2002). Briefly, spleen specimens of 6-8 week old mice were embedded in OCT compound (Sakura Finetek USA, Torrance, Calif.) and frozen at −80° C. Frozen tissues were sliced, mounted and stained with 5 µg/ml Gr-1-biotin antibody. ABC peroxidase (Vector laboratories, Inc., Burlingame, Calif.) and DAB peroxidase substrate (Sigma-Aldrich, St. Louis, Mo.) were then applied to slides according to the company protocols. Finally, hematoxylin solution was used to stain Gr-1 negative cells.

Results

B7-H4KO mice display normal numbers and ratios of T, B, NK, NKT cells, and macrophages. There are no obvious alterations in T cell responses, judged by in vitro proliferation of purified T cells by CD3 cross-linking, allogeneic antigen stimulation, or cytolytic T cell response to alloantigens. These results indicate that polyclonal T cell responses to antigens are not impaired in B7-H4KO mice. Consistent with these in vitro findings, it was also found that B7-H4KO mice have normal responses to Con-A induced hepatitis (Dong, H. et al., *Immunity*, 20327-336 (2004)), hapten-induced hypersensitivity (Tsushima, F. et al. *Eur. J. Immunol.*, 33:2773-2782 (2003)), and OVA-induced airway inflammation (Kamata, T. et al, *J. Clin. Invest.*, 111:109-119 (2003)). B7-H4-deficient mice were also found to be comparable to wild-type mice in OT-I and OT-II cell expansion to OVA proteins (Sica, G. L. et al., *Immunity*, 18849-861 (2003)), CD4-Vβ8.118.2 T cell expansion to superantigens (Tamada, K. et al., *J Immunol.*, 168:4832-4835 (2002)), and CTL activities to allogeneic antigens in vivo (Tamada, K. et al, *Nature Med.*, 6:283-289 (2000)). Normal B cell responses were also observed after immunization by TNP-KLH (Tamura, H. et al., *Blood* 97:1809-1 816 (2001)). B7-H4KO mice do not develop spontaneous autoimmune diseases up to 1.5 years in SPF condition.

Figure 2A:
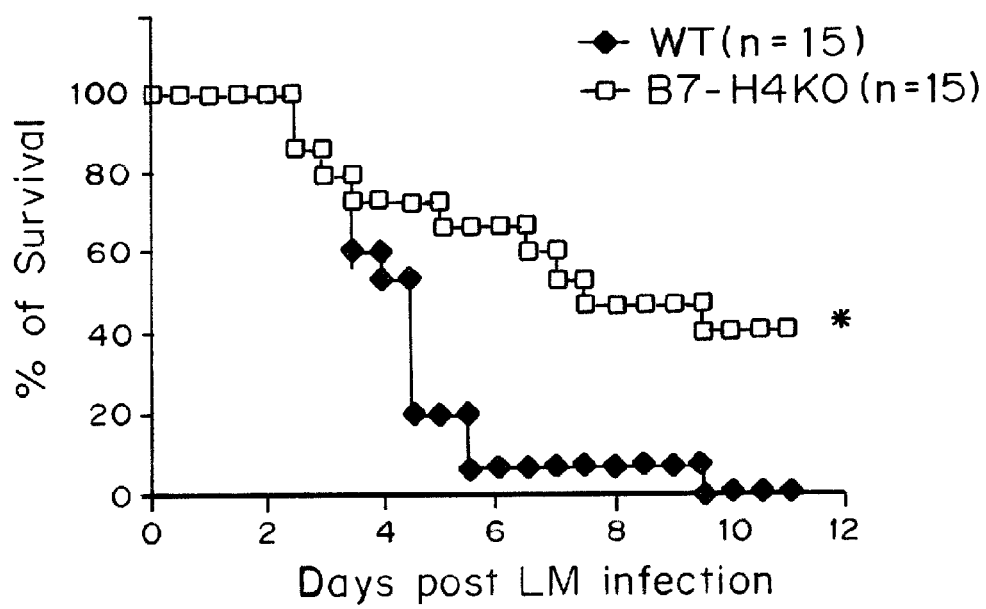
FIG. 2a is a line graph of percent survival versus days post Listeria monocytogenes (LM) infection in wildtype mice (♦) or B7-H4KO mice (□).
Figure 2B:
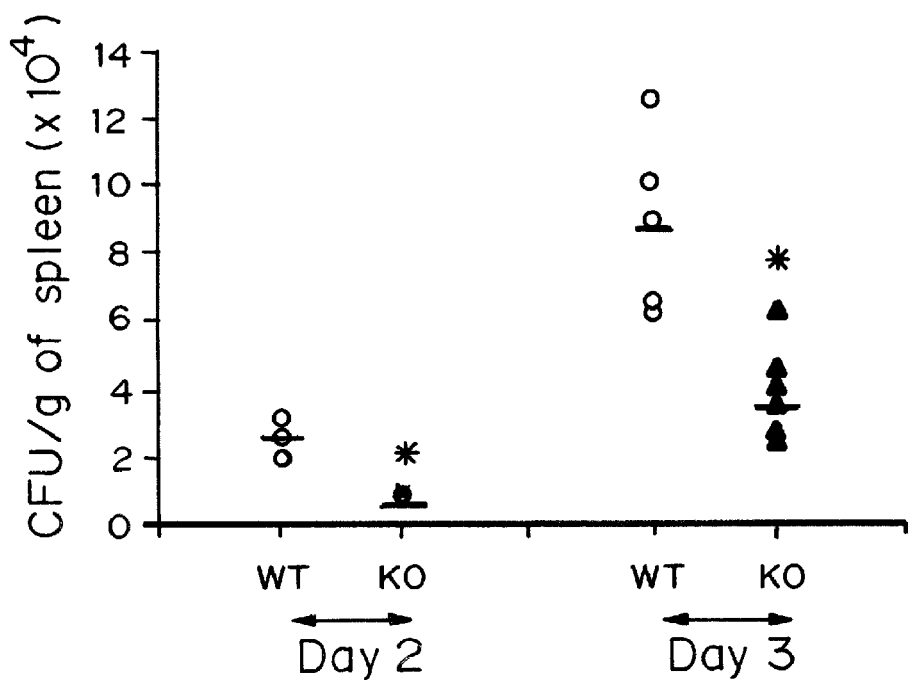
FIG. 2b is a graph of CFU/g of spleen (×10$^8$) on day 2 or day 3 for wildtype mice (○) or B7-H4KO mice (▲) infected with LM.

While the data indicates that B7-H4 plays a minimal role in antigen-driven T and B cell responses in assays, these responses were conducted in the absence of active infection, which usually requires a much more sophisticated coordination between innate and adaptive immunity. To test this possibility, the effect of B7-H4 ablation was evaluated in mice infected with *Listeria monocytogenes* (LM) to examine whether B7-H4 contributes to immunity against infection. Mice were challenged with an intra-peritoneal dose (i.p.) ($2 \times 10^6$ CFU) of LM sufficient to induce lethality. The survival of these mice was then subsequently evaluated. B7-H4KO mice were significantly more resistant to LM infection: B7-H4KO mice survived much longer than their wild-type (WT) littermates and up to 40% of mice cleared bacteria and lived indefinitely, while all littermates died around day 9 (FIG. 2a). This effect is correlated with decreased *Listeria* numbers in the spleens (FIG. 2b) and liver in B7-H4KO mice. Interestingly, the majority of mice were dead within 3-4 days, time points at which adaptive immunity is usually not yet developed. The results thus suggest a role of B7-H4 in altering the context of the innate immune response.

Figure 2C:
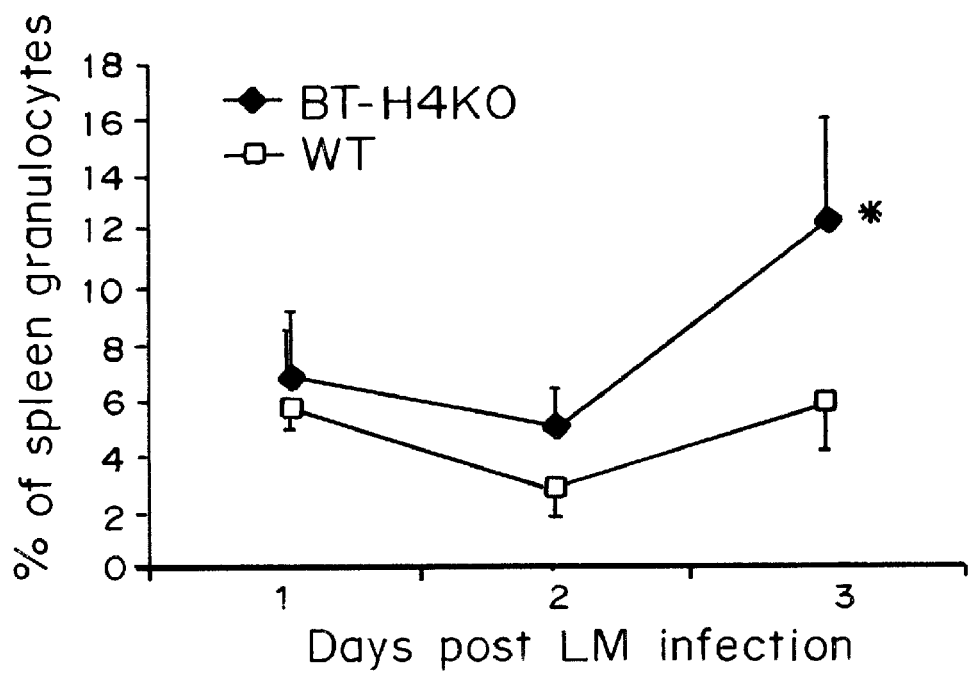
FIG. 2c is a line graph of percent spleen granulocytes versus days post LM infection in wildtype mice (♦) or B7-H4KO mice (□) infected with LM.

To address mechanisms of this resistance, the cell compositions of both innate and adaptive immunity were examined. The mice were infected with *Listeria* and T, B, NK, macrophages and granulocytes in peripheral blood and in lymphoid organs were examined by specific mAb. Although there were no significant differences in NK, macrophages, T cells, and B cells within the first 3 days after LM infection, significantly more granulocytes in spleens were found from LM-infected B7-H4KO mice than identically infected WT littermates at day 3 upon infection (FIG. 2c). Similar results were also obtained in granulocytes isolated from livers and in peripheral blood after infection. In uninfected B7-H4KO mice, however, granulocyte numbers were within normal range of WT controls. The results indicate that the role of B7-H4 is to inhibit granulocyte responses during LM infection.

Figure 2D:
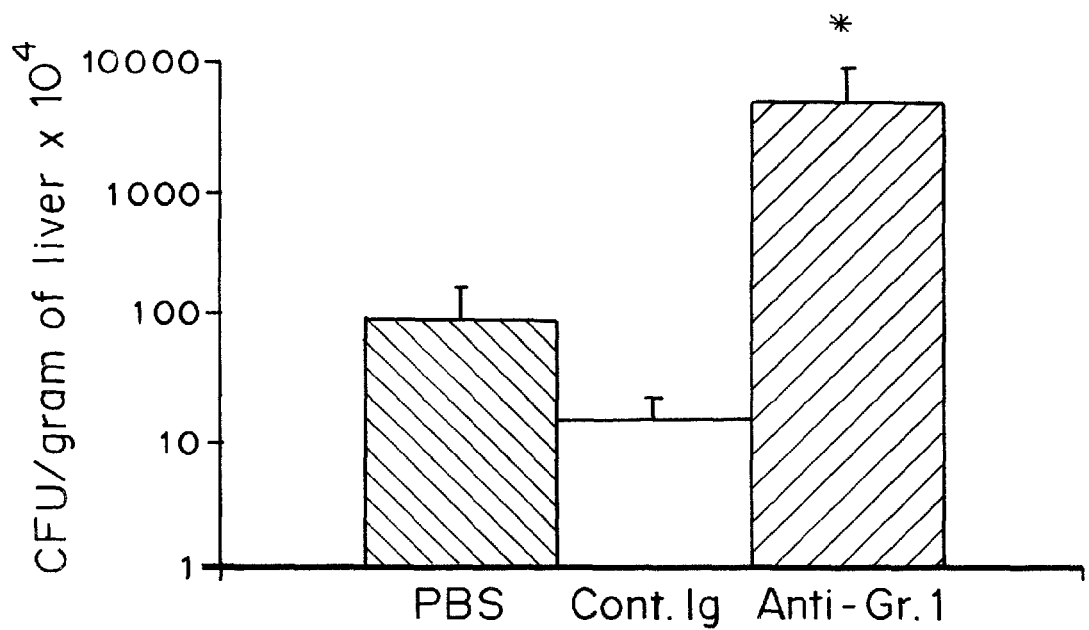
FIG. 2d is a bar graph of CFU/g of liver×10$^4$ in three B7-H4 KO mice or littermate control i.p. injected with 150 pg Gr-1 mAb or control Rat IgG (LPS-free) 24 hours prior to Listeria infection. Mice were then i.p. injected with 3×10$^6$ CFU of Listeria. Twenty-four hours post infection, mice were terminated and Listeria in liver was counted.

To determine if granulocytes are required for the resistance of LM infection in B7-H4KO mice, granulocytes were depleted by inoculation of Gr-1 mAb. Injection of Gr-I mAb led to rapid decline of granulocytes to undetectable levels at day 2 in spleens. Depletion of Gr-I and granulocytes led to a significant increase of LM load in livers from B7-KO mice, in comparison with those treated with either PBS or isotype-matched control mAb (FIG. 2d). Depletion of NK cells by NKI.I mAb did not affect colony formation of LM in liver, while depletion of macrophages by carrageenan increased LM colonies to a moderate but less significant level as compared to Gr-I cell depletion. The results thus show that Gr-I and granulocytes play a critical role in the resistance to LM infection in the absence of B7-H4.

Figure 3:
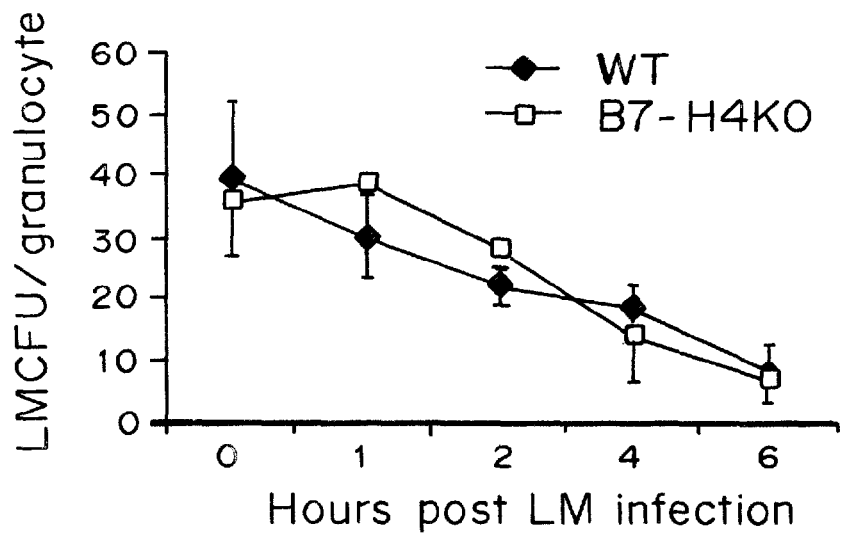
FIG. 3 is a bar graph of LM CFU/granulocyte versus hours post LM infection in wildtype mice (♦) or B7-H4KO mice (□).

Whether B7-H4-deficient granulocytes have modified functionalities were determined by co-culture of purified granulocytes and LM. B7-H4-deficient granulocytes display normal uptake and growth inhibition of LM in culture system (FIG. 3). In addition, respiratory burst and phagocytosis by B7-H4KO granulocytes are also normal, indicating B7-H4KO granulocytes are functionally indifferent from WT granulocytes. Therefore, increased resistance to LM infection in B7-H4KO mice is likely caused by an increased number, not increased functional capacity of granulocytes.

Example 3

Granulocyte-Mediated Innate Resistance in B7-H4KO Mice is Independent of Adaptive Immunity Activated and memory T cells are important components in the immunity against LM (Nathan, C. *Nature Rev. Immunol.*, 6:173-182 (2006)). While the data supports that resistance of B7-H4KO mice to LM infection requires granulocytes, it is unknown whether adaptive immunity also contributes to this resistance. Because increased granulocyte numbers post-LM infection was a major phenotype found in B7-H4KO mice, the responses of B7-H4KO mice to LM infection were explored in the absence of adaptive immunity. B7-H4KO mice were backcrossed to the RAG-1 KO background to eliminate T and B cells.

Results

Unlike RAG-1 KO (RKO) mice, which possess small spleens, B7-H4/RAG-1 double KO (DKO) mice display enlarged spleens. The spleen sizes of DKO mice are similar to those of WT and B7-H4KO mice in B6 background. Further analysis of cell components in spleen, peripheral blood, liver, and bone marrow revealed that Gr1+ CD11b+ granulocytes increased dramatically.

Figure 4:
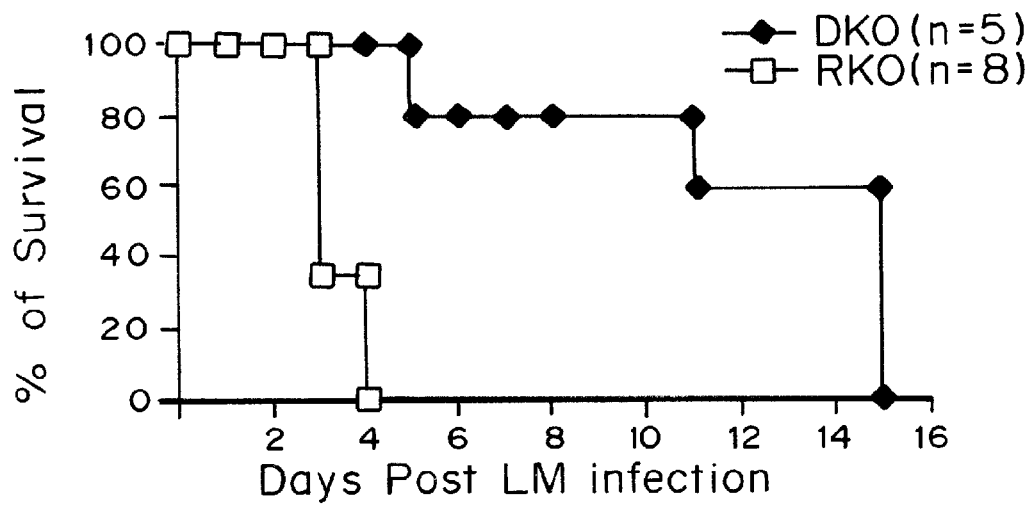
FIG. 4 is a line graph of percent survival versus days post LM infection in RKO mice (♦) or B7-H4KO mice (□).

RKO and DKO mice were then challenged by administration of a lethal dose of LM to examine their innate resistance. Infection of RKO mice by LM led to exponential growth of LM in liver and 100% mortality by day 4 (FIG. 4). In sharp contrast, DKO mice have significantly less bacterial load in the liver at day 2 and the majority of the mice were able to survive more than 10 days LM challenge (FIG. 4). Similar exponential growth of LM in other organs including spleens were observed, indicating a dissemination of LM infection. In contrast to long-term survival of a significant fraction of infected B6 background B7-H4KO mice (FIG. 2a), all DKO mice eventually died of infection at day 15, supporting an important role of adaptive immunity (FIG. 4). Combined with rapid clearance of LM from liver and other organs in DKO mice as early as day 2, the results indicate that lack of B7-H4 confers enhanced innate immunity against LM infection, which is largely mediated through increased granulocytes.

Example 4

B7-H4 Directly Inhibits Proliferation of Granulocytes

Bone Marrow Cell Culture and Granulocyte Growth and Inhibition Assay

Bone marrow cells were aspirated and prepared as described by Wilcox, R. A. et al., *Blood*, 103:177-184 (2004). For B7-H4-mediated growth inhibition, B7-H4Ig or control murine Ig were coated in 96-well plates overnight. After extensive washing, BM cells were plated $2\times10^6$/well in 24-well plates with or without recombinant murine G-CSF (Pepro Tech Inc., Rocky Hill, N.J.) at indicated concentrations. Cells were harvested at indicated time points and cell numbers were counted with Beckman Coulter Counter (Beckman, Fullerton, Calif.). To examine cell growth, $2\times10^5$/well of BM cells were plated in 96-well plates with G-CSF. After being pulsed with $^3$HTdR, cells were harvested with FilterMate® cell harvester (Perkin Elmer, Shelton, Conn.) 16 hours post $^3$HTdR pulse. The incorporated $^3$HTdR was detected by Trilux® Liquid Scintillation and Luminescence Counter (Wallac, Turku, Finland). For cell division assay, BM cells were first labeled with 2 µM of carboxyfluorescein diacetate succinimidyl ester (CFSE, Invitrogen, Carlsbad, Calif.) and then were added to the cultured in 96- or 24-well plates. Cells were harvested at indicated time points, stained with mAb Gr-1 and CD11b and subjected to flow cytometry analysis for CFSE content (2) at different time points.

Results

Figure 5A:
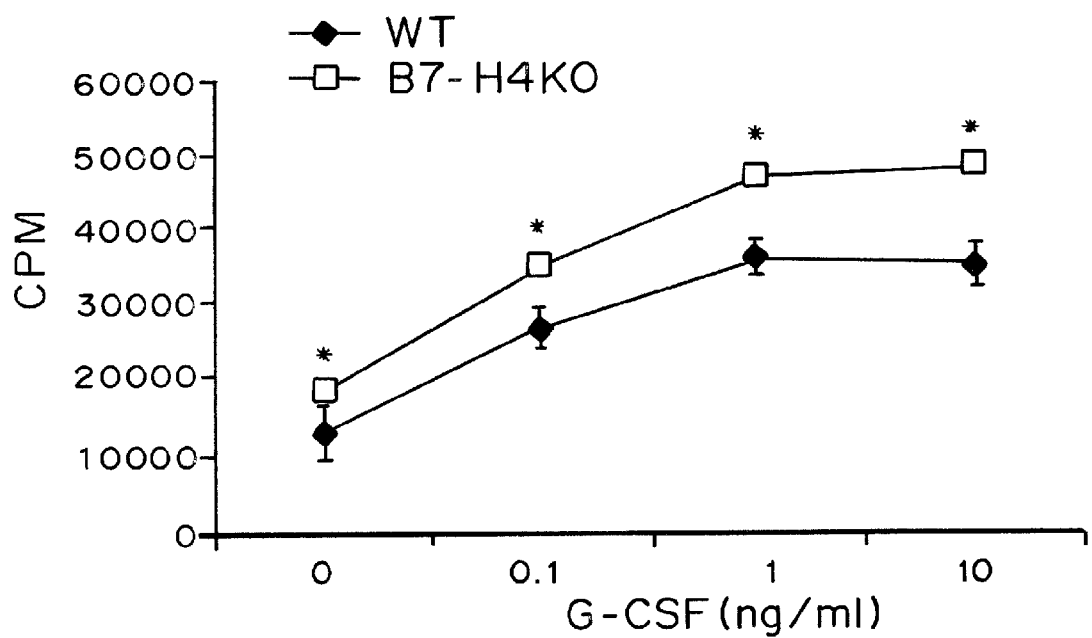
FIG. 5a is a line graph of CPM versus G-CSF (ng/ml) in two×10$^6$ bone marrow cells of wildtype mice (♦) or B7-H4KO mice (□) plated with the indicated concentration of recombinant G-CSF for 3 days. The cultures were pulsed with $^3$HTdR fort 8 hrs before the end of culture, harvested and counted by a scintillation counter.
Figure 5B:
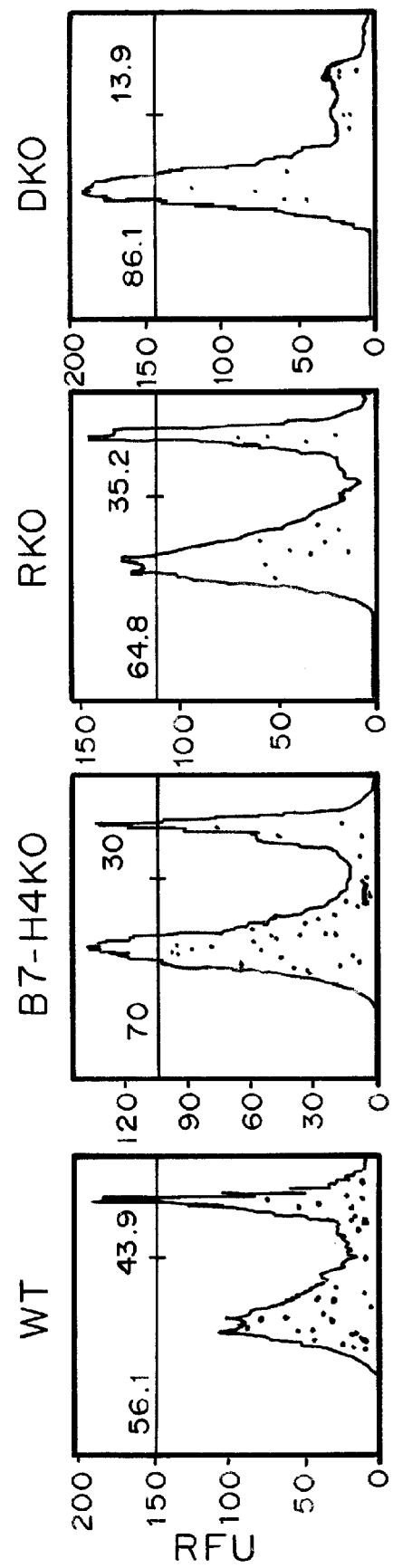
FIG. 5b is a panel of line graphs of the dilution of CFSE in gated Gr-1+CD11b+ granulocytes analyzed by flow cytometry. Two×10$^6$ of bone marrow cell from the indicated mice were labeled with CFSE and cultured for 5 days. Cells were harvested and doubly stained with Gr-1/CD11b mAb.

Increased granulocytes in B7-H4KO mice suggest that B7-H4 play a role in delivering an inhibitory growth signal to granulocytes. Granulocytes from B7-H4 KO mice were examined to determine whether they have better growth potential than WT granulocytes. To do so, bone marrow (BM) cells, which contain large numbers of granulocyte precursors, were prepared and cultured from WT or B7-H4 KO mice in the presence or absence of G-CSF for 3 days to facilitate differentiation of granulocyte/neutrophil. The proliferation of BM cells was subsequently determined by $^3$HTdR incorporation. FIG. 5A shows that while BM cells respond to G-CSF by proliferating in a dose-dependent fashion, proliferation of BM cells from B7-H4KO mice was significantly higher than those from WT mice. Flow cytometry analysis of BM cells which respond to G-CSF in the end of culture, shows that more than 95% of survived cells are CD11b+Gr-1+ granulocytes. While this data is consistent with an inhibitory effect of B7-H4 in granulocytes, other cellular components in BM cells may also contribute to proliferation. To precisely exclude this possibility, BM cells were labeled with CFSE and after stimulation with G-CSF for 3 days, the cells were stained with anti-Gr-1+/CD11b+ mAbs to monitor granulocytes for cell division. FIG. 5b shows that 70% Gr-1+CD11b+ granulocytes from B7-H4KO mice (B6) divide at least once whereas only 56% granulocytes from WT B6 mice had diluted CSFE. Similar, but more significant differences were found in mice with the RAG-1 KO background: 86% granulocytes from DKO mice entered division whereas only 64.8% granulocytes from RKCO mice had diluted CSFE. The results thus indicate that lack of B7-H4 on BM cells increase proliferation of BM-derived granulocytes.

Considering that the lack of B7-H4 could result in increased proliferation of BM-derived granulocytes, whether B7-H4 could directly inhibit their proliferation was determined. To test this, WT BM-derived granulocytes were cultured in the presence of recombinant B7-H4Ig fusion protein and examined proliferation of granulocytes. Proliferation of WT BM cells was significantly inhibited by B7-H4Ig, a fusion protein of B7-H4 extracellular portion and immunoglobulin Fc. The inhibition was evident at day 3 of the culture and became more significant at day 4 and 5 (FIG. 6a). Addition of 0.1 ng/ml of G-CSF in the culture, albeit moderately increasing proliferation of BM cells, did not significantly overcome B7-H4Ig mediated suppression (FIG. 6b). Increasing G-CSF to 1 ng/ml in the culture, however, could recover B7-H4Ig-mediated growth inhibition of BM cells in large degree (FIG. 6c). Similar inhibition was also observed in B7-H4 deficient granulocytes. Combined together, the results provide further evidence that B7-H4 is inhibitory for the proliferation of granulocytes, which could be reversed by G-CSF.

It has been discovered that B7-H4 can negatively regulate innate immunity against *Listeria* infection. It is believed that the effect of B7-H4 is mediated through growth suppression of granulocytes. In the context of broad expression pattern of B7-H4 in peripheral tissue, the data supports B7-H4 as an important regulatory molecule in the control of innate immunity in peripheral tissues, in addition to the previously described role of B7-H4 in the inhibition of T cell responses.

In B7-H4KO mice, the majority of the extracellular portion of B7-H4 protein is deleted to assure complete elimination of interaction between endogenous B7-H4 and its putative receptor. Ablation of this gene, however, does not have a profound effect on T cell responses to polyclonal and allogeneic antigen stimulation in vitro. Similar observations have been made in a recent study reported by Suh, W. K. et al. *Mol. Cell. Biol.,* 26:6403-641 1 (2006). While these findings indicate that B7-H4 does not substantially influence the inhibition of strong polyclonal T cell responses to CD3 cross-linking or allogeneic antigens, it is possible that B7-H4 affects more selective steps during cascade of T cell responses. For example, a recent study shows that although B7-H4KO mice responded normally to several types of airway inflammatory responses as well as LCMV and influenza infection, the mice have slightly enhanced T-cell immune responses to *Leishmania major* infection. Responses of granulocytes in this knockout system, however, were not examined. The experiments indicate that a dominant role of B7-H4 in *Listeria* infection is to suppress granulocyte-mediated innate immunity and this effect could also be observed in RAG-1 KO mice in the absence of adaptive immune system. Therefore, in addition to inhibition of T cell immunity as reported previously, B7-H4 may play a critical role in negative regulation of innate immunity against bacterial infection.

Although there is slightly increased granulocytes in the spleens of B61B7-H4KO mice, dramatic increase of granulocytes occur upon LM infection (FIG. 2). This increase, however, is not simply due to increased recruitment by LM-induced inflammation. B7-H4 KO mice in B6 background have a small increase of granulocytes in blood, bone marrow and spleen without infection. A more dramatic elevation of granulocytes is observed in RAG-1 KO background. In addition, bone marrow cells from B7-H4KO mice produce more granulocytes in the presence of G-CSF stimulation. Finally, inclusion of B7-H4 protein in culture significantly inhibits growth of bone marrow-derived granulocytes. The role of B7-H4 in the inhibition of granulocytes could be reversed, at least partially, by addition of higher concentrations of G-CSF in culture. G-CSF is a critical factor for growth and homeostasis of granulocyte in vivo. The result suggests that B7-H4 may serve as a negative regulator to antagonize the role of G-CSF in vivo. Combined together, the results support that B7-H4 provides an inhibitory signal for responsiveness of granulocytes to G-CSF, a foremost growth factor for granulocytes, and thus may regulate homeostasis of granulocytes.

It has been shown that B7-H4, upon binding to its putative receptor, inhibits cell cycle progression on T cells (Sica, G. L. et al., *Immunity* 18:849-861 (2003); Kryczek, I. et al. *J Eicp Med,* 203:871-881 (2006)). In the cell culture system, dilution of CFSE and incorporation of $^3$HTdR are clearly inhibited (FIG. 6a). Bone marrow cells were observed to undergo proliferation (FIG. 6a) and cell division (FIG. 5g) in the absence of exogenously supplied G-CSF, a key growth factor for granulocytes. It is possible that endogenous G-CSF is produced by bone marrow cells and maintains basal level of proliferation in vitro. This suppression could be largely reversed by adding G-CSF (FIG. 6c). During the culture, significant increases of cell apoptosis was not observed for up to 5 days. Therefore, growth inhibition may be a dominant mechanism in granulocytes by B7-H4 ligation. B7-H4 mRNA is widely expressed by various cells while its cell surface expression could be largely contained in cytoplasm as observed in ovarian cancer and infiltrating macrophages (Kryczek, I. et al., *J Eicp Med,* 203:871-881 (2006)). Surface expression of B7-H4 could be regulated by cytokines within the bone marrow microenvironment to inhibit granulocyte growth.

Granulocytes, including neutrophils, are one of the earliest cells to arrive at the site of an infection and are the first line of individual defense against infection through their capacity to phagocytose (Nathan, C. *Nature Rev. Immunol,* 6:173-1 82 (2006)). The findings showing an increased resistance to *Listeria* infection in B7-H4KO mice implicates a new approach to enhance innate immunity against infection by *Listeria* and possibly other pathogens. It is also interesting that B7-H4 KO mice in the RAG-1 background have a more profound increase in the number of granulocytes and are more resistant to early phase LM infection in comparison with B7-H4 KO mice in B6 background. These data implicate a possible suppressive role of adaptive immunity components including T and B cells in granulocyte homeostasis and response to *Listeria* infection. Therefore, the method to selective blockade of B7-H4 expression such as neutralizing mAb or appropriately engineered B7-H4 protein with antagonistic activity represents a new approach to increase granulocytes and enhanced innate immunity against pathogen infection.

Example 5

Soluble B7-H4 in the Sera of Rheumatoid Arthritis Patients Correlates with Disease Severity Patients and Healthy Donors:

Sera samples were obtained from 68 patients with diagnosed RA, 35 patients with diagnosed SLE and 24 normal healthy donors under approval of the Internal Review Board of Mayo Clinic. RA patients were classified to 4 groups as follows. 0: no active disease, 1: 1-4 active joints, 2: 5-9 active joints, 3: more than 10 active joints with or without extraarticular disease.

Detection of Soluble B7-H4, Collagen-Specific Autoantibodies and Anti-dsDNA Autoantibody For detection of human sH4, specific mAb hH4.3 (2 μg/ml) and hH4.1 (2 μg/ml) against human B7-H4 was used as capture and detection, respectively, in ELISA. To remove Rheumatoid Factor, the sera were treated with human IgG agarose (Sigma-Aldrich, St. Louis, Mo.) before detection in ELISA. For measurement of collagen-specific autoantibodies, chicken collagen (1 μg/ml) was coated on the plate overnight at 4° C., and biotin conjugated anti-mouse IgG, IgG1, IgG2a and IgG2b Ab (BD, San Jose, Calif.) as detection antibodies. To measure anti-dsDNA autoantibody levels, dsDNA from salmon testes at 10 μg/ml in PBS was coated on the plate overnight at 4° C., and HRP conjugated anti-mouse IgG, (BD, San Jose, Calif.).

Western Blot:

The sera was mixed with 2× sample buffer (4% SDS, 0.2% bromophenol blue, 20% glycerol in 100 mM Tris buffered saline) and boiled for 5 min. The samples were electrophoresed under reducing conditions on a 10% Ready gel (Bio-Rad, Richmond, Calif.) and the proteins electroblotted onto Protran BA85 (Whatman, Florham Park, N.J.). The Immobilon-P sheet was blocked in 5% nonfat dry milk in PBS for 1 h and incubated with the antibody at 4° C. overnight. After repeated washing (five times 5 min), bound antibody was detected with horseradish peroxidase (HRP)-labeled.

Results

To detect sH4, sera from individual patients with diagnosis of rheumatoid arthritis based on American Rheumatism Association criteria were analyzed by enzyme-linked immunosorbent assays (ELISA) using two specific monoclonal antibodies (mAb) binding to different epitopes on human B7-H4. In this assay, 65% (44 out of 68) samples from patients with RA and 43% (15/35) from patients with SLE were above background and therefore positive. Evaluation of sH4 in healthy donors (HD) showed only 13% (3/24) were positive (FIG. 7a). sH4 is significantly higher in RA and SLE patients than healthy donors (P<0.05). In addition, the mean concentration of sH4 in RA (96.1 ng/ml) and SLE (36.9 ng/ml) was significantly higher than those of the healthy donors (3.8 ng/ml). The results indicate that sH4 is elevated in a significant portion of RA and SLE patients.

Western blot analysis was used to validate the presence of sH4 in sera from 3 patients with rheumatoid arthritis. Using specific mAb against B7-H4, the sera from 3 RA patients, who have detectable sH4 in ELISA, showed a single 50-kDa band. This matched the size of predicted extracellular domain of human B7-H4. In contrast, no band was observed in sera from three healthy donors (FIG. 7b). The data support the presence of sH4 in the sera of RA patients.

The association of elevated concentration of sH4 with the severity of RA was investigated. Based on severity of diseases, 68 RA patients were classified into 4 groups (0-3) with most severe diseases in group 3 as described in Methods. The mean concentration of sH4 in group 3 (260.7 ng/ml) was significantly higher than those of group 0 (22.0 ng/ml) or Group 1 (18.8 ng/ml). However, there was no significant difference among group 0-2 by Scheffe test (FIG. 7c). The data thus indicate that RA patients in group 3 have highest level sH4 and suggest that sH4 might play a role in the progression of severe RA.

Example 6

Soluble B7-H4 Exacerbates Collagen-Induced Arthritis in a Mouse Model

Mice

Male DBA/1j mice, MRL-lpr/lpr mice and C57BL/6-lpr/lpr (B6-lpr/lpr) were obtained from the Jackson Laboratory (Bar Harbor, Me.). Age-matched mice, 4-10 weeks old, were used for all experiments. B7-H4KO mice were generated in this laboratory as described above and have been backcrossed to B6 background for 10 generation. DBA/1j×B7-H4KO mice were generated by backcrossed B7-H4KO mice into DBA/1j backgrounds for 5 generations. B6-lpr/lpr×B7-H4KO mice were obtained by backcrossing between B6-lpr/lpr and B7-H4KO mice. All mice were maintained in the Animal Facility at Johns Hopkins Hospital under approval protocol by the Institutional Animal Care and Use Committee.

Induction of Collage-Induced Arthritis:

CIA was induced in 8-10 weeks old male DBA/1j mice by intradermal tail base injection of 0.2 mg chicken collagen (Sigma-Aldrich, St. Louis, Mo.) in 0.05 M acetate acid, supplemented with 4.0 mg/ml mycobacterium tuberculosis (DIFCO, Detroit, Mich.) emulsified in complete Freund adjuvant. Fourteen days after first primary immunization, the mice were identically boosted once. Severity of disease was evaluated by visual inspection of the paws. Each paw was scored for the degree of inflammation on a scale from 0 to 4:0, no evidence of erythema and swelling; 1, erythema and mild swelling confined to the midfoot (tarsals) or ankle joint; 2, erythema and mild swelling extending from ankle to the midfoot; 3, erythema and mild swelling extending from ankle to metatarsal joints; 4, erythema and severe swelling encompassing the ankle, foot, and digits. Scores from all four paws were added to give the total for each animal.

Murine B7-H4 Constructs

B7-H4Ig construct was prepared as described by Sica, G. L. et al. B7-H4, a molecule of the B7 family, negatively regulates T cell immunity. Immunity 18, 849-61 (2003)). To generate B7-H4V and B7-H4VC plasmids, 2 flanking 5' and 3' primers were designed with XhoI and EcoRI restriction sites, respectively (5'primer; 5'-ccgctcgagccaccatggcttcct-tgggggcag-3' (SEQ ID NO:6), 3'primer for B7-H4V; 5'-cggaat-tccgctaatttatctctggcatact-3' (SEQ ID NO:7), 3'primer for B7-H4VC; 5'-cggaattccgctaagagttcagcaactgcag-3' (SEQ ID NO:8)). Appropriate regions of cDNA were amplified using primers. PCR product was digested with XhoI and EcroRI and ligated into XhoI/EcroRI-digested pcDNA3.1 vectors (Invitrogen, Carlsbad, Calif.).

Collagen-Specific T Cell Proliferation and Cytokine Production.

The spleen was removed on day 14 after the last immunization. CD4+ T cells were purified by using magnetic beads (Miltenyi Biotec, Auburn, Calif.). Whole splenocytes or purified CD4+ T cells were stimulated with denatured (60° C., 30 min) chicken type II collagen (CII) in 96 well flat bottom microtiter plates for 72 hr, and pulsed with [$^3$H] thymidine (1 μCi/well) (Amersham Pharmacia Biotech, Piscataway, N.J.) for the last 12 hr. In the culture of purified CD4+ T cells, irradiated (50Gy) splenocytes from the syngeneic mice were added as antigen-presenting cells. Supernatants from the cultures were collected after 48 hr and assayed for mouse IFN-γ (BD, San Jose, Calif.) and IL-17A (eBioscience) using ELISA kit according to the protocols recommended by manufacturer.

Results

Figure 8A:
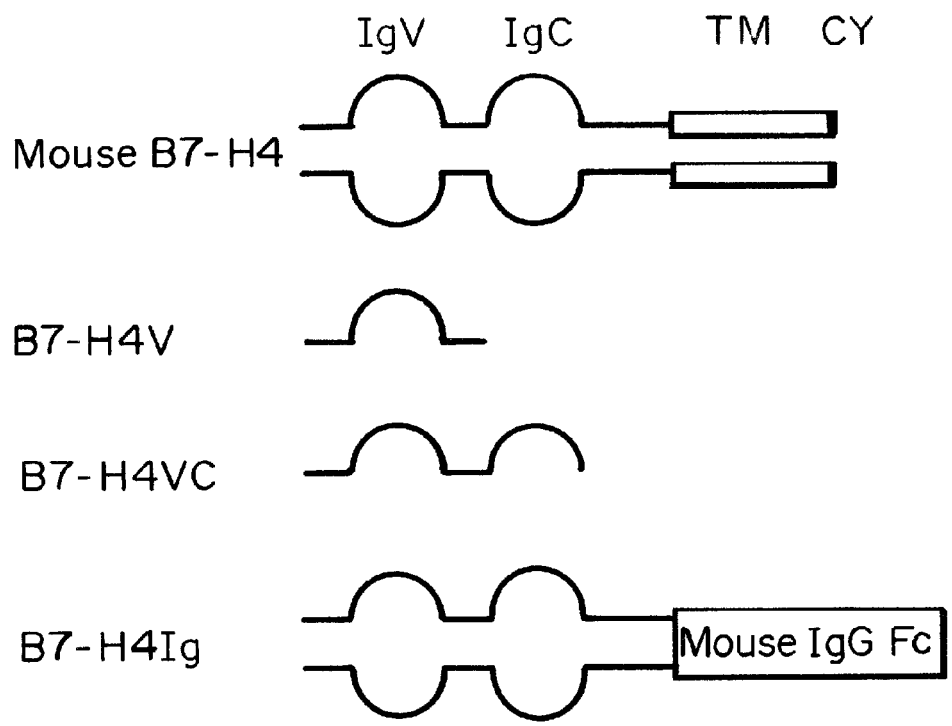
FIG. 8a is a schematic of the B7-H4V, B7-H4VC and B7-H4Ig. IgV domain; IgV, IgC domain; IgC. TM; transmembrane domain, CY; cytoplasmic domain.

To recapitulate and explore possible role of sH4 in the pathogenesis of RA, a mouse model of collagen-induced arthritis (CIA) was used. CIA is a well-characterized mouse model for human arthritis, in which injection of collagen into DBA/1j mice induces swelling and progressive inflammation in large joints and lead to arthritis. To express sH4 in vivo, an expression vector, B7-H4VC, was constructed in which the transmembrane and intracellular domains of mouse B7-H4 cDNA were deleted, and the truncated gene encoding both IgV and IgC domains were placed under the control of CMV immediate early promoter. Another vector, B7-H4V, containing only IgV domain of B7-H4 was also produced (FIG. 8a). Upon expression, these truncated proteins/polypeptides are expected to compete with endogenous B7-H4 on the cell surface to bind its putative receptor. Parental vector is included as the control. By a hydrodynamic expression procedure known in the art, injection of these plasmids led to expression of sH4 up to 2 μg/ml in the sera, based on specific capture sandwich ELISA using two anti-murine B7-H4 mAb.

Figure 8B:
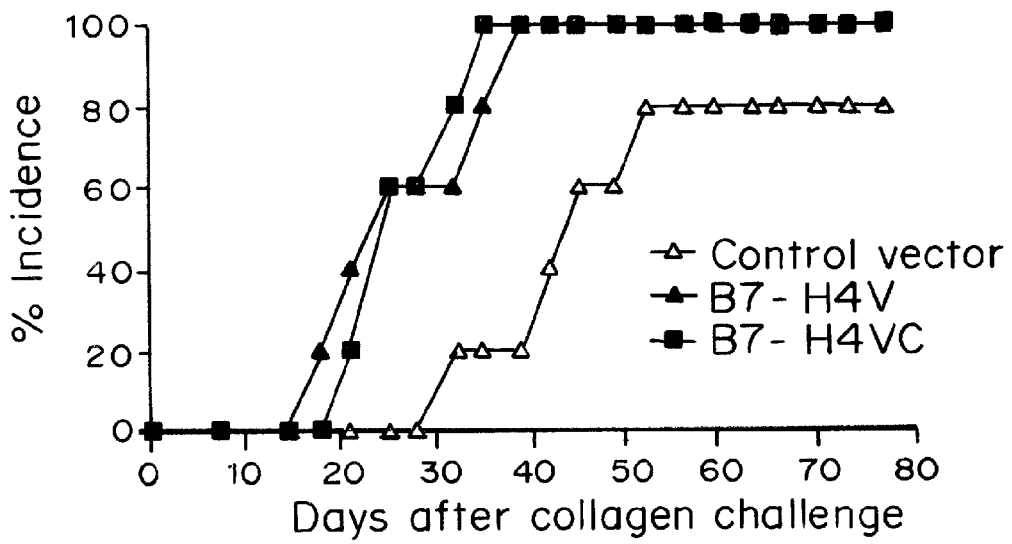
FIG. 8b shows a graph of percent incidence versus days after collagen injection of mice immunized with chicken type II collagen in CFA on day 0 and day 21. Three groups of mice were hydrodynamic injection with control vector (□), B7-H4V (▲) or B7-H4VC (■) on day −1 and day 20; means±s.e.m. (n=5).
Figure 8C:
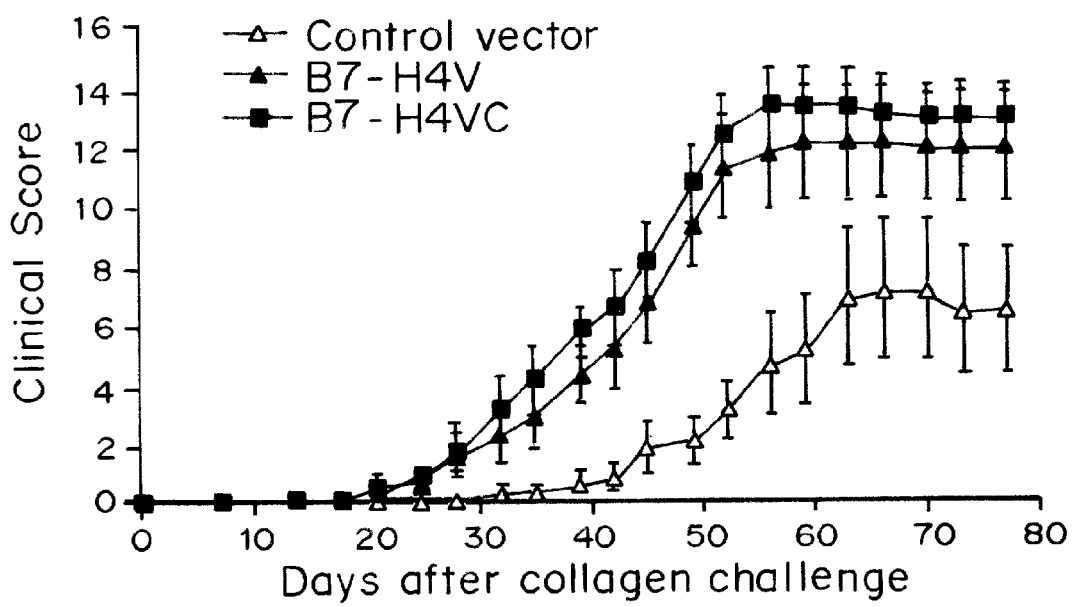
FIG. 8c shows a graph of clinical score versus days after collagen injection of mice immunized with chicken type II collagen in CFA on day 0 and day 21. Three groups of mice were hydrodynamically injected with control (□), B7-H4V (▲) or B7-H4VC (■) vector on day −1 and day 20; means±s.e.m. (n=5).

In the CIA model, immunization of DBA/1j mice with collagen led to appearance of arthritic symptom starting around 28 days. Control vector-treated mice developed arthritis beginning at day 32 and 80% of mice developed disease on day 60 after first immunization. Injection of B7-H4VC led to earlier development of disease (17 days) and 100% mice developed arthritis around 30 days. Similar results were also seen in the mice injected with B7-H4V (FIG. 8b). Furthermore, treatment by either B7-H4V or B7-H4VC significantly increase severity of arthritis as indicated by increased clinical score (FIG. 8c), increased swelling of footpad and increased infiltration of inflammatory cells in joints as shown in histopathology analysis.

Figure 8D:
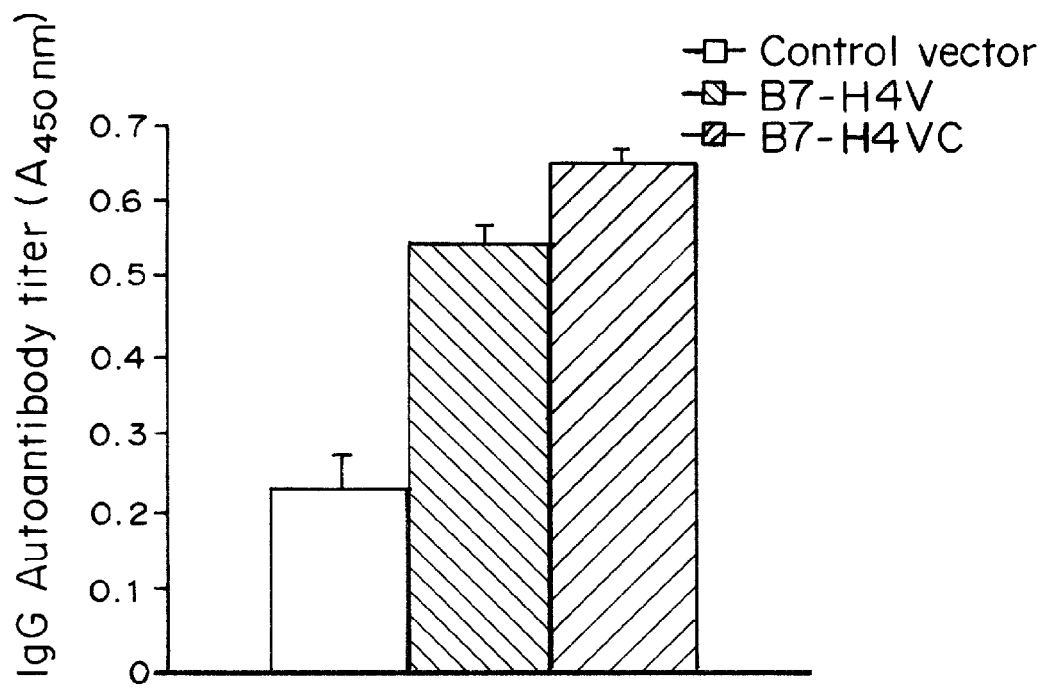
FIG. 8d is a bar graph showing serum levels of anti-CII total IgG. white; control vector, gray; B7-H4V, black; B7-H4VC; means±s.d.
Figure 8E:
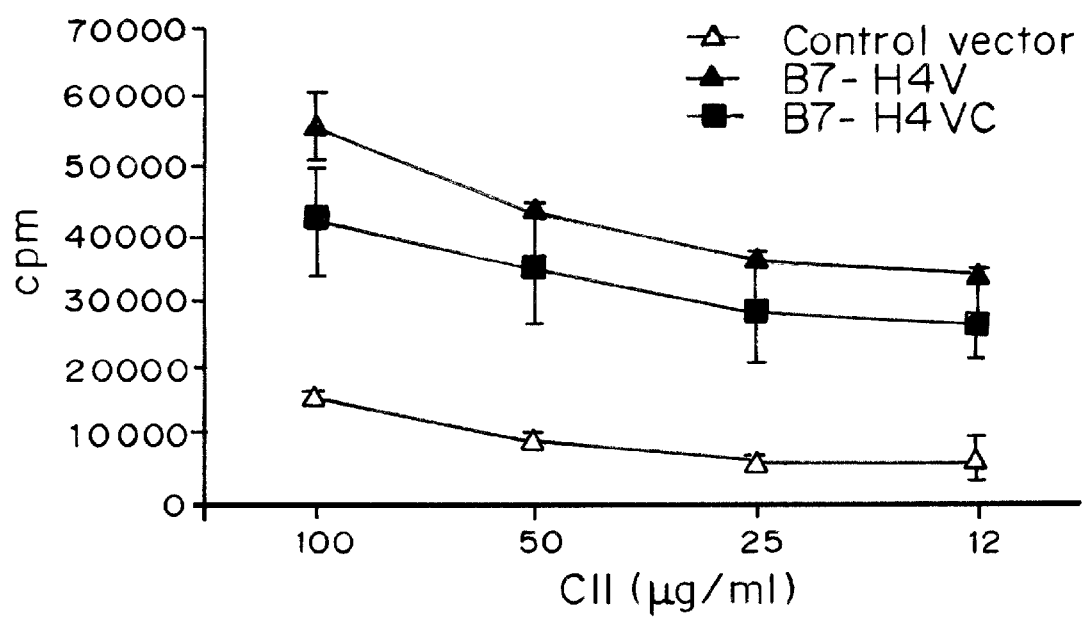
FIG. 8e shows a line graph of counts per minute versus CII µg/ml. Whole splenocytes from CIA mice injected with control vector (□), B7-H4V (▲) or B7-H4VC (■) on day 30 were cultured in the presence of the indicated amounts of CII for 72 hr; means±s.d.
Figure 8F:
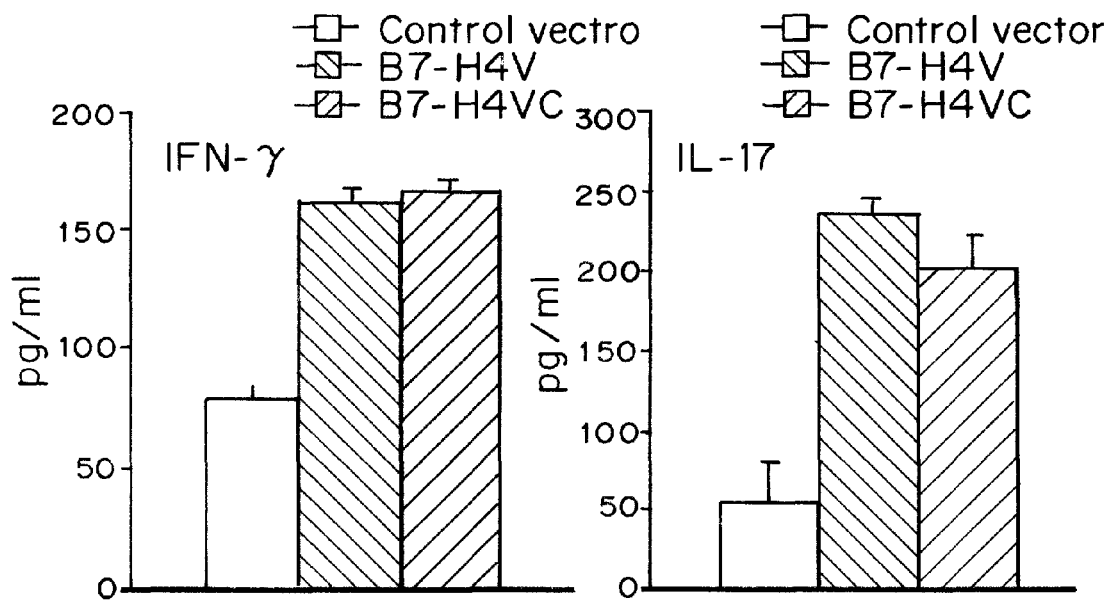
FIG. 8f shows bar graphs of supernatants of whole splenocytes after a 72 hr culture assessed for IFN-γ and IL-17 production by ELISA; means±s.d.
Figure 12:
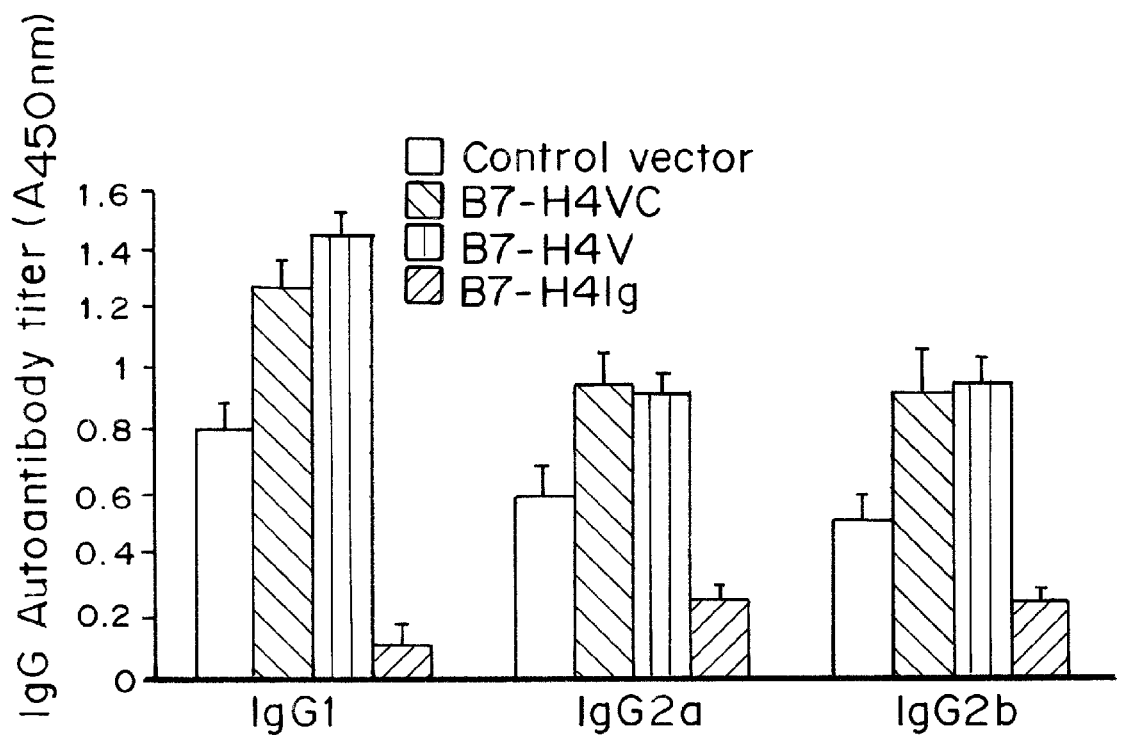
FIG. 12 shows bar graphs of serum levels of anti-CII IgG1, IgG2a and IgG2b in CIA mice treated with control vector, B7-H4V, B7-H4VC or B7-H4Ig were measured by ELISAs in day 30; means±s.d.
Figure 13:
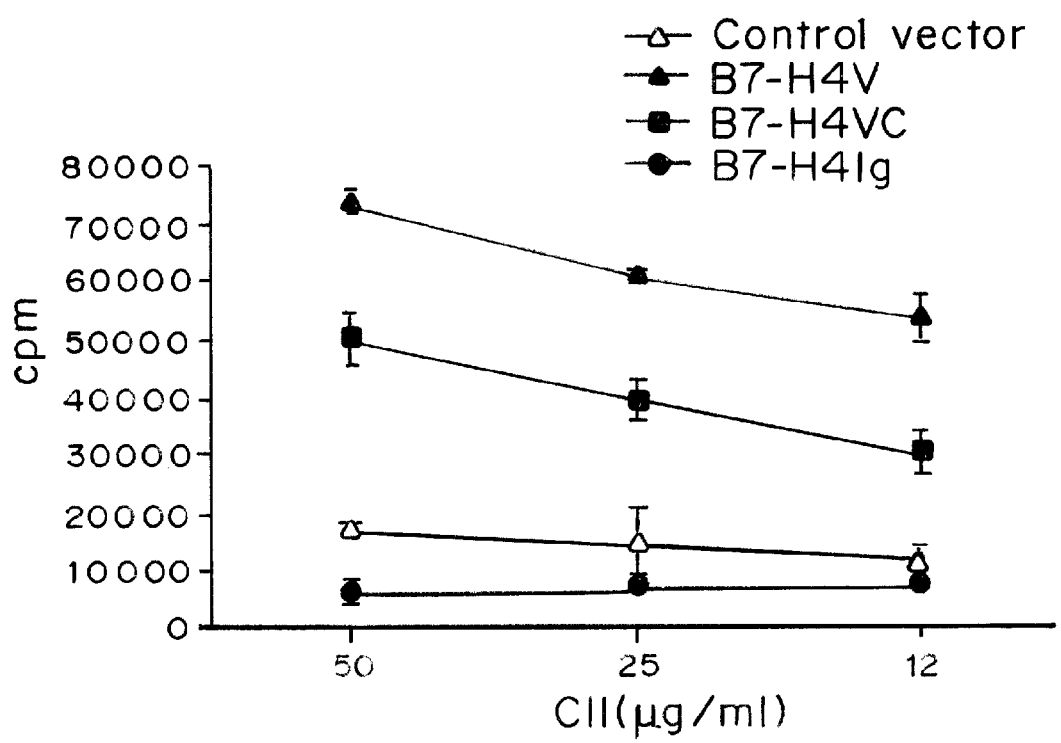
FIG. 13 shows line graphs of counts per minute verses CII µg/ml indicating proliferation of splenic CD4 T cells in CIA mice injected with control vector (□), B7-H4V (▲), B7-H4VC (■) or B7-H4Ig (●) on day 30 in the presence of the indicated amounts of CII for 72 hr; means±s.d.

Assessment of cellular and humoral immune responses revealed that increased incidence and severity of arthritis was accompanied with elevated total IgG autoantibodies (FIG. 8d) as well as other subtypes including IgG$_1$, IgG$_{2a}$ and IgG$_{2b}$ to collagen CII at day 30 after immunization and B7-H4VC or B7-H4V treatment (FIG. 12). Stimulation of total spleen cells or purified CD4+ T cells from mice, which were treated with B7-H4VC or B7-H4V, by CII also induced much higher level of proliferation in comparison with mice treated with control vector (FIG. 8e and FIG. 13). Importantly, IFN-γ and IL-17, two major cytokines responsible for CIA progression, also increase significantly in the cultures (FIG. 8f). Taken together, the data demonstrate that sH4 enhance autoimmune responses against CII and exacerbate autoimmune CIA.

Figure 8G:
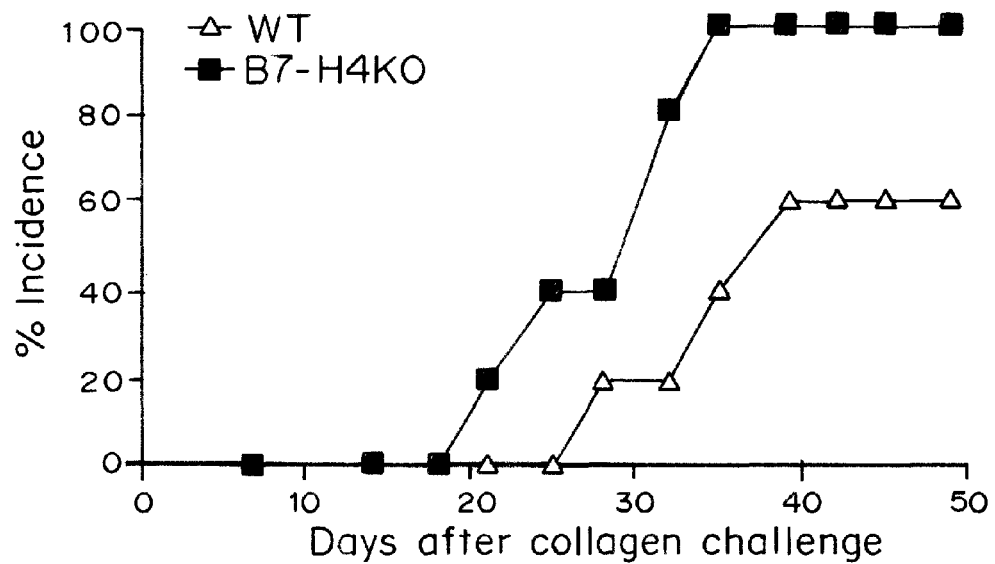
FIG. 8g shows a line graph of incidence versus days after collagen injection of mice immunized with chicken type II collagen in CFA on day 0 and day 21. WT mice (□), B7-H4KO mice (■); means±s.e.m. (n=5).
Figure 8H:
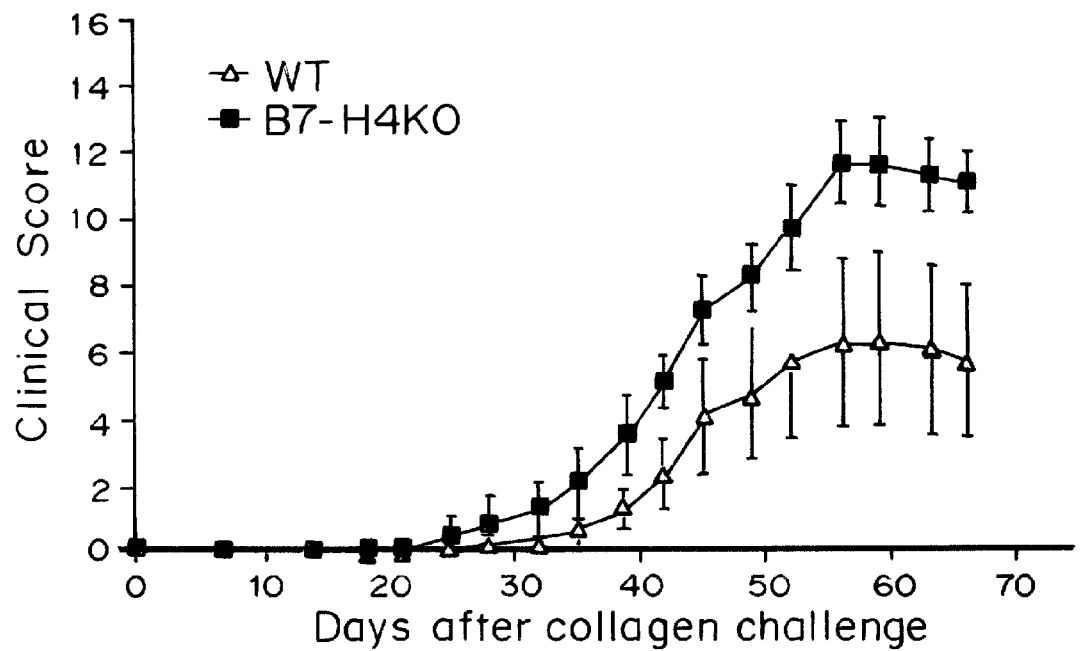
FIG. 8h shows a line graph of clinical score of mice immunized with chicken type II collagen in CFA on day 0 and day 21. WT mice (□), B7-H4KO mice (■); means±s.e.m. (n=5).

If B7-H4VC and B7-H4V act as a decoy to block the effect of endogenous B7-H4 on the cell surface, a similar exacerbation effect that should also be observed in B7-H4 deficient mice (B7-H4KO). To test this, B7-H4KO phenotype mice were backcrossed to DBA/1j background for 5 generations. B7-H4KO-DBA/1j mice develop normally and do not have obvious abnormality in gross appearance and development of immune system. These mice, however, developed much more severe CIA, showing higher accidence (FIG. 8g) and clinical score (FIG. 8h) than B7-H4+/+ control mice, results similar to those from B7-H4VC or B7-H4V-treated mice. Therefore, the data support that sH4 functions as a decoy molecule to increase autoimmune responses and exacerbate CIA.

Example 7

Increased Neutrophils are Responsible for Exacerbation of CIA by sH4

Air Pouch Assay for Neutrophils

The air pouch assay was performed as described by Edwards, J. C. et al., *J Pathol*, 134:147-56 (1981). Briefly, mice were anesthetized with 2, 2, 2-Tribromoethanol (Sigma-Aldrich, St. Louis, Mo.) and subcutaneous dorsal pouches were created by injection of 5 ml of sterile air. After 3 day, pouches were re-injected with 3 ml air. On day 6 after the first injection, 50 μg LPS in 1 ml PBS was injected into the pouches. Five hours later, mice were anesthetized and pouches were lavaged with 3 ml PBS to collect infiltrating cells.

Results

Figure 9A:
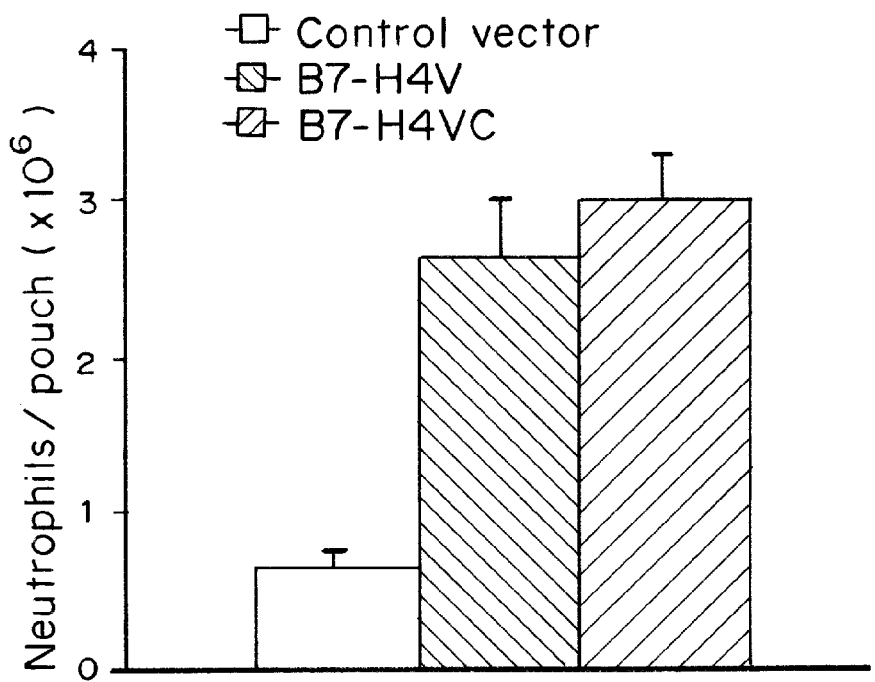
FIG. 9a shows a bar graph of an air pouch assay showing sH4 activates neutrophils by its dominant-negative activity. Subcutaneous air pouches were injected with LPS (50 µg). After 5 h, Gr-1+ neutrophils were quantified by flow cytometry of cells rinsed from the pouch with sterile saline. Each bar represents the average of six to eight mice in each group; means±s.d.

B7-H4KO mice are resistant to *Listeria* infection due to rapid increase of neutrophils. Further experiments demonstrated that B7-H4 could directly inhibit growth of neutrophil progenitors. Therefore, sH4 may block endogenous B7-H4 and thereby exacerbate CIA via neutrophil-mediated inflammation, a hypothesis which may provide an interpretation for progressive inflammation of RA. Whether or not expression of sH4 increases neutrophils in murine peripheral tissues was explored. Due to difficulty to directly access neutrophil number in RA lesions in mouse, an air pouch assay in which neutrophils could be collected from subcutaneous air pouches upon induction of inflammation were used. As shown in FIG. 9a, mice injected with B7-H4V or B7-H4VC had significantly more neutrophils in each air pouch than that of control vector. Together with previous studies in B7-H4KO mice, the results indicate that sH4 induce a rapid increase of neutrophils in peripheral tissues in vivo.

Figure 9B:
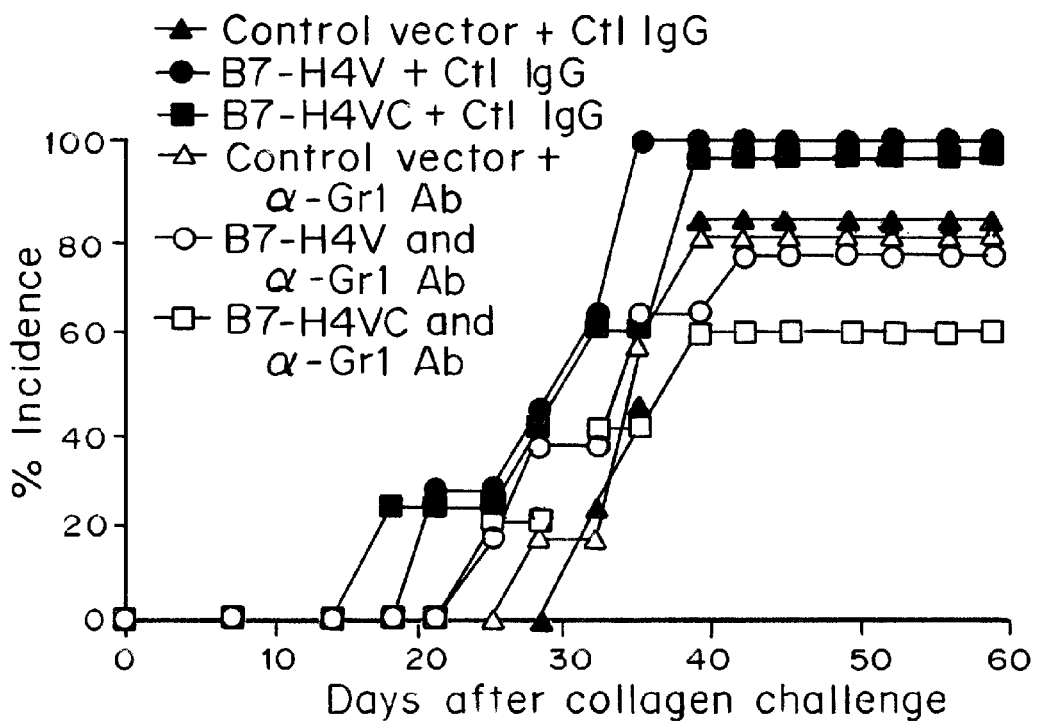
FIG. 9b shows a line graph of incidence versus days after collagen challenge. Six groups of mice were treated with control vector and control rat IgG (▲), control vector and anti-Gr-1 Ab (□), B7-H4V and control rat IgG (●) and B7-H4V and anti-Gr-1 Ab (○), B7-H4VC and control rat IgG (■) and B7-H4VC and anti-Gr-1 Ab (■); means±s.e.m. (n=5)
Figure 9C:
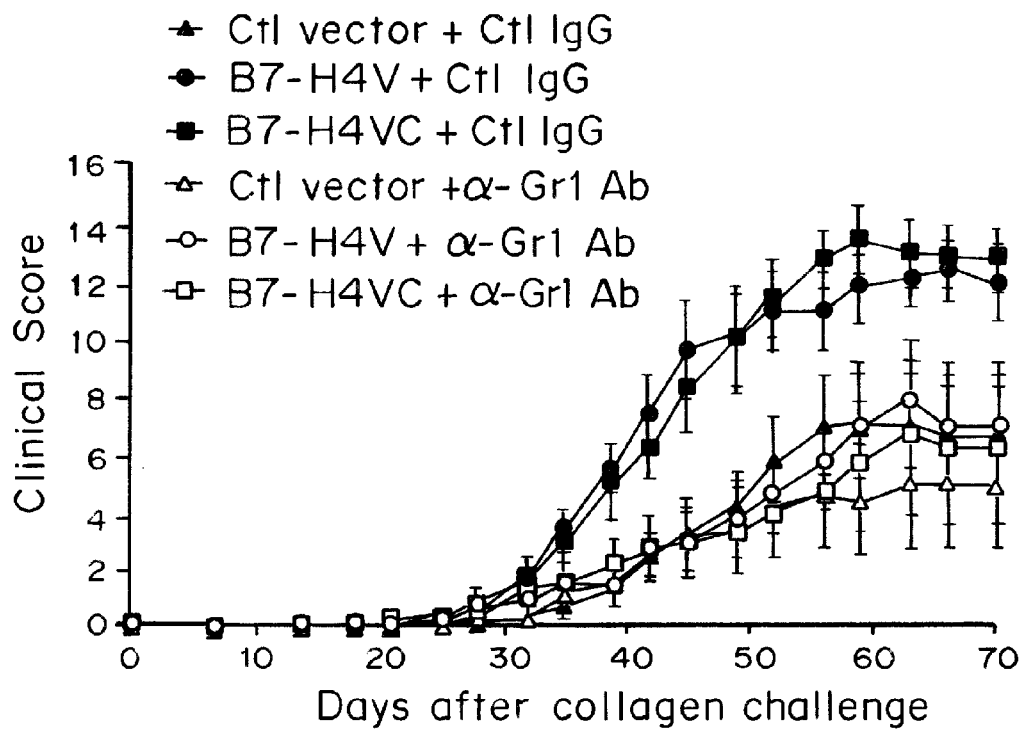
FIG. 9c shows a line graph of clinical score of CIA mice versus days after collagen challenge. Six groups of mice were treated with control vector and control rat IgG (▲), control vector and anti-Gr-1 Ab (□), B7-H4V and control rat IgG (●) and B7-H4V and anti-Gr-1 Ab (○), B7-H4VC and control rat IgG (■) and B7-H4VC and anti-Gr-1 Ab (■); means±s.e.m. (n=5).

Neutrophils were depleted to investigate whether the effect of sH4 in CIA exacerbation could be eliminated. CIA-mice were treated with B7-H4VC or B7-H4V and subsequently treated with anti-Gr-1 antibody every other day to deplete neutrophils. Enhanced effect of B7-H4V or B7-H4VC in both CIA incidence (FIG. 9b) and clinical score (FIG. 9c) was completely eliminated by anti-Gr-1 antibody treatment. The results thus support that neutrophils are responsible for the effect of sH4 in the progression of CIA.

Example 8

Soluble B7-H4 Exacerbates SLE-Like Diseases in lpr Mice and Enhances Autoimmune Responses Urine Protein Excretion Urinary protein excretion was determined by dipstick analysis (GERMAINE, San Antonio, Tex.). The proteinuria grade was scored from 0 to 4 as follows: grade 0, normal; grade 1, 30 mg/dl; grade 2, 100 mg/dl; grade 3, 300 mg/dl; grade 4, 2000 mg/dl.

Histological Assessments of Arthritis and Nephritis

CIA mice were sacrificed at day 35. The hind paws were removed, fixed in Formalin, decalcified in 10% EDTA, embedded in paraffin, sectioned, and stained with H&E. For histological evaluation of renal disease, mice were sacrificed at 6 months of age. Kidneys were either fixed in formalin or snap-frozen in Tissue Tek (Sakura Finetek, Torrance, Calif.) for cryostat sectioning. Formalin-fixed tissue was embedded in paraffin, sectioned, and stained by the periodic acid-Schiff (PAS) method. Frozen sections were fixed in acetone and 1% paraformaldehyde, and stained with FITC-conjugated anti-mouse IgG Ab or C3 Ab (ICN/Cappel, Aurora, Ohio).

Figure 7A:
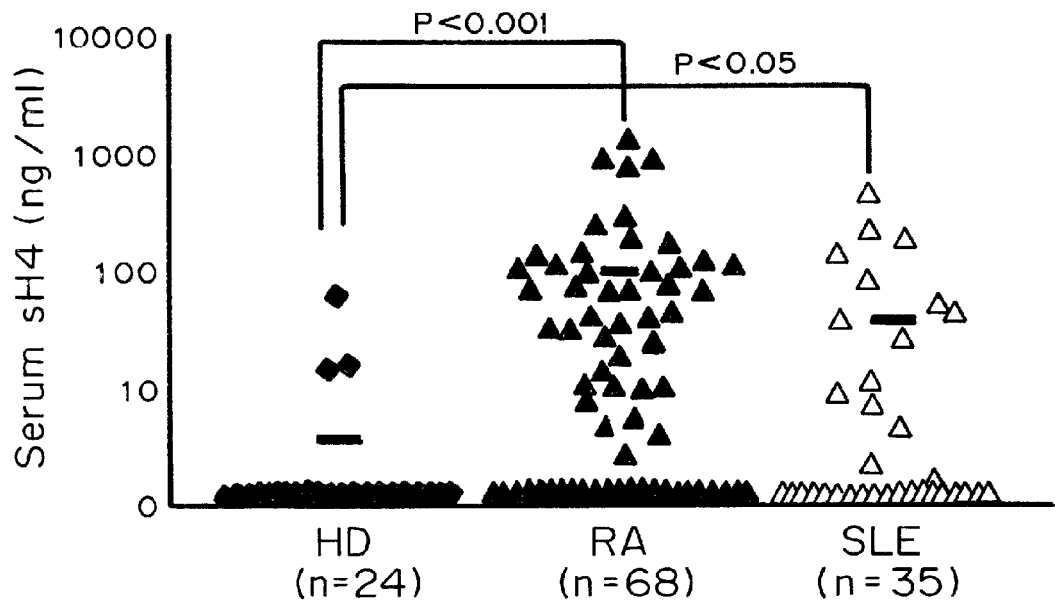
FIG. 7a is a graph showing sH4 in sera of healthy donors (HA) (♦), RA (▲), and SLE (□) patients.
Figure 7B:
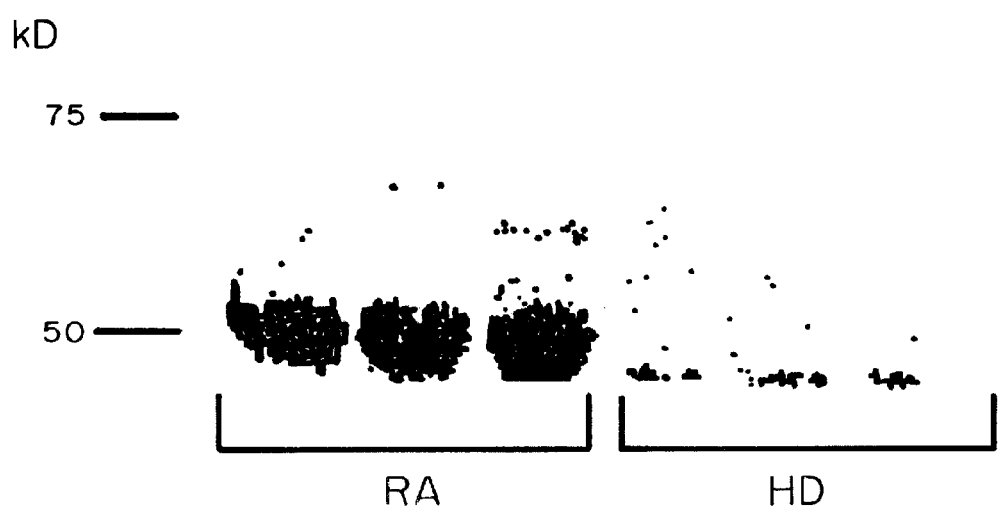
FIG. 7b is a western blot showing that sH4 is present in RA patients and not in healthy donors.
Figure 7C:
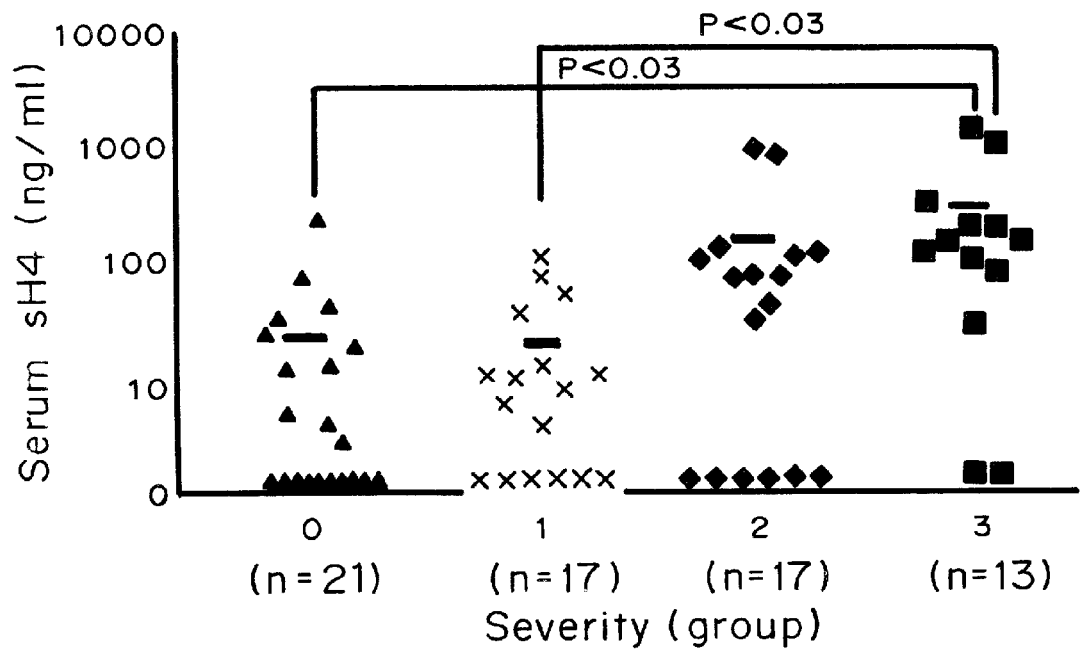
FIG. 7c is a graph showing the correlation between concentration of the sH4 and the severity groups 0 (▲), 1 (X), 2 (♦), and 3 (■) of RA.
Figure 10A:
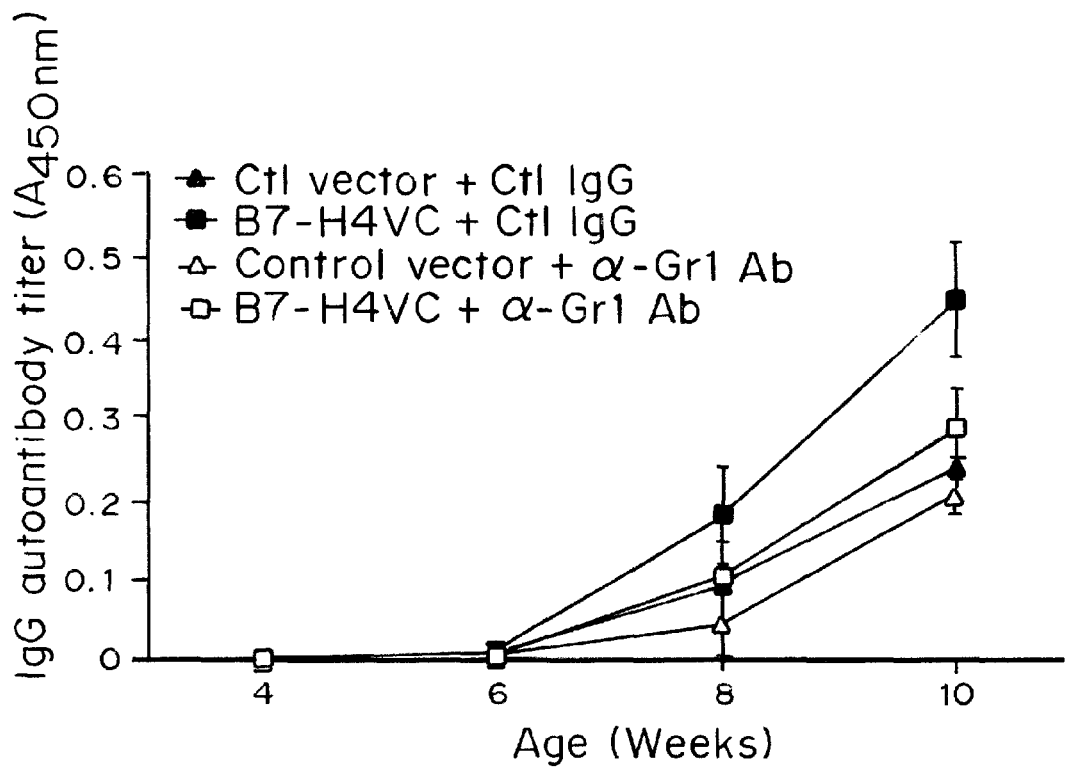
FIG. 10a shows a line graph of the serum levels of anti-double strand DNA autoantibody in MRL-lpr/lpr mice. Four groups of mice were treated with control vector and control rat IgG (♦), control vector and anti-Gr-1 Ab (□), B7-H4VC and control rat IgG (■) and B7-H4VC and anti-Gr-1 Ab (□); means±s.e.m. (n=5).

A significant fraction of SLE patients also have detectable sH4 in sera (FIG. 7a). It is possible that sH4 may also play a role in the progression of SLE. To test this, sH4 was investigated to determine whether it could promote autoimmunity in MRL-lpr/lpr mice, in which the mice spontaneously develop progressive StE-like symptoms largely due to the effects of autoantibodies and lymphoproliferation. MRL-lpr/lpr mice were treated with the B7-H4VC plasmid and anti-dsDNA autoantibodies in sera were evaluated. As shown in FIG. 10a, upon treatment by the B7-H4VC, concentration of anti-dsDNA autoantibodies in sera elevated significantly higher than the mice treated with control plasmid at 10 weeks. Depletion of neutrophils by injection of anti-Gr-1 antibody completely eliminated this effect, a result similar to the observation in the CIA model. This initial study suggests that sH4 also plays a role in promoting autoimmune responses in this SLE model.

Figure 10B:
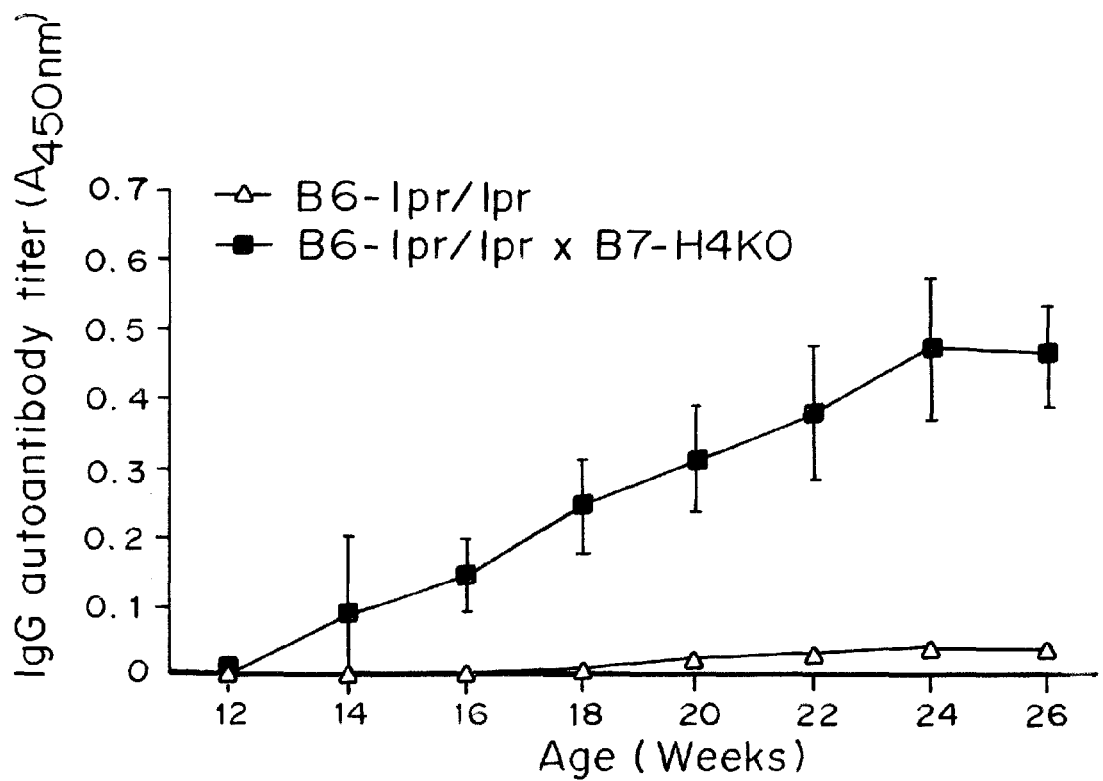
FIG. 10b shows a line graph of the serum levels of anti-double strand DNA autoantibody in B6-lpr/lpr mice (□) or B6-lpr/lpr×B7-H4KO mice (■); means±s.e.m.
Figure 10C:
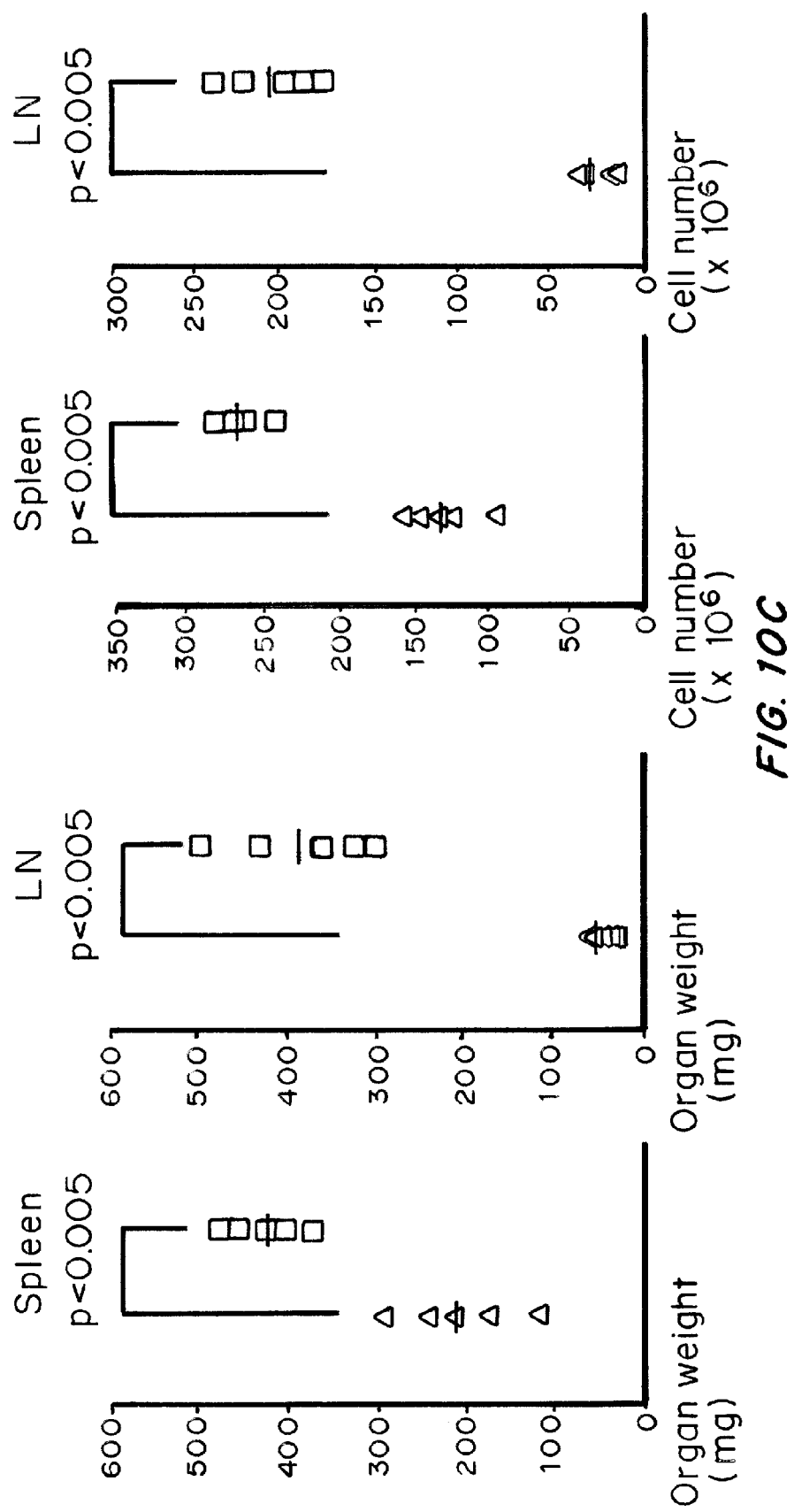
FIG. 10c shows a panel of graphs showing weight and total cell number in the spleens and peripheral lymph nodes of 24 weeks old B6-lpr/lpr mice (□) or B6-lpr/lpr×B7-H4KO mice (□). (n=5)
Figure 10D:
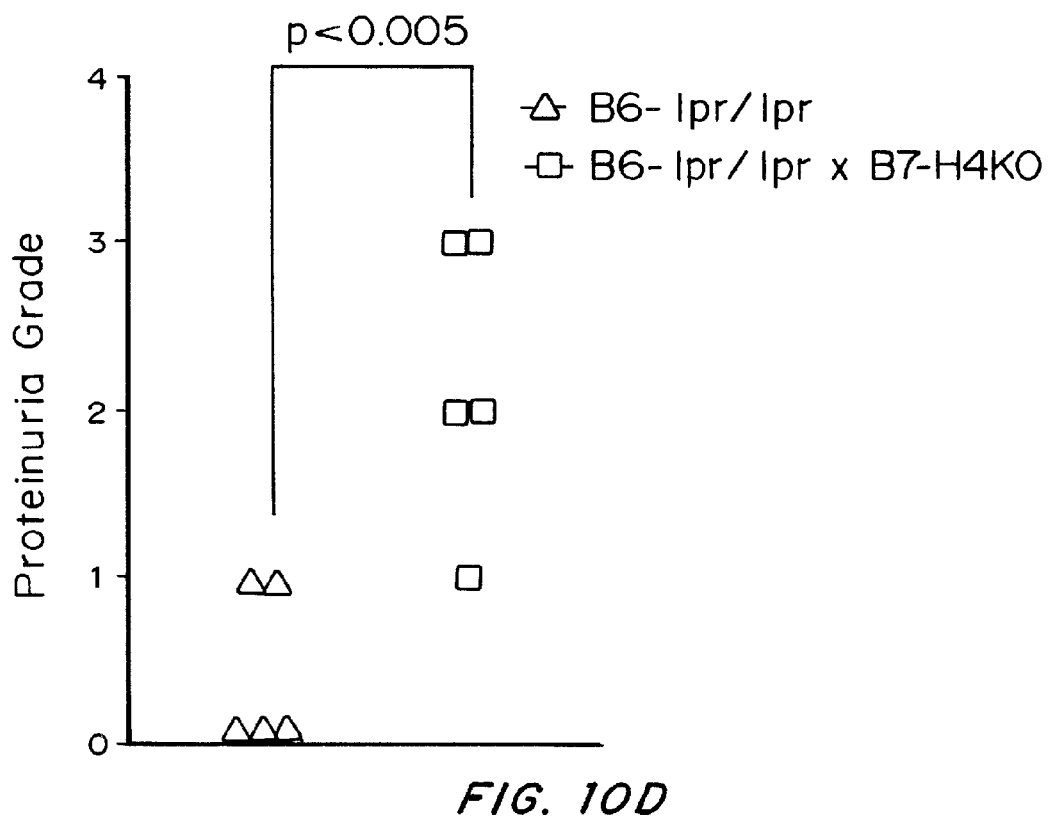
FIG. 10d shows a graph indicating proteinuria grade of 24 weeks old B6-lpr/lpr mice (□) or B6-lpr/lpr×B7-H4KO mice (□). (n=5).

To facilitate analysis of the immune responses and the role of sH4 in the pathogenesis of SLE, B7-H4−/− phenotype mice were backcrossed to B6-lpr/lpr mice, a strain with similar but less aggressive SLE-like symptoms as the MRL-lpr strain. As expected, anti-dsDNA IgG autoantibodies were developed much earlier and in much higher titers in B6-lpr/lpr×B7-H4KO mice than the control B6-lpr/lpr mice (FIG. 10b). Importantly, B6-lpr/lpr×B7-H4KO mice rapidly developed severe splenomegaly and lymphoadenopathy with significantly increased weight (FIG. 10c) compared with control B6-lpr/lpr mice. The spleen and lymph nodes were much larger and cellularity of these organs increased significantly in B6-lpr/lpr×B7-H4KO mice than the controls (FIG. 10c). The major cell components, which are increased significantly upon sH4 treatment in these organs, are neutrophils (Gr-1+ CD11b+) and T cells (CD3+CD8+, CD3+CD4+ and CD3+ CD4−CD8−B220+). B6-lpr/lpr×B7-H4KO mice developed severe glomerulonephritis with interstitial inflammatory cells infiltrates, hypercellular glomerulus and increased mesangial cells. In addition, the mice also developed vasculitis with perivascular cell infiltration, the glomerular deposition of total IgG) and C3 as well as increased proteinuria (FIG. 10d) within 30 weeks. In contrast, control B6-lpr/lpr mice have normal kidneys without any visible pathology up to 24 months. Taken together, the results demonstrate that sH4 exacerbates SLE-like diseases in lpr mice by enhancing antibody and cell-mediated autoimmune responses and pathology.

Example 9

Inhibition of CIA Progression by B7-H4Ig

Figure 11A:
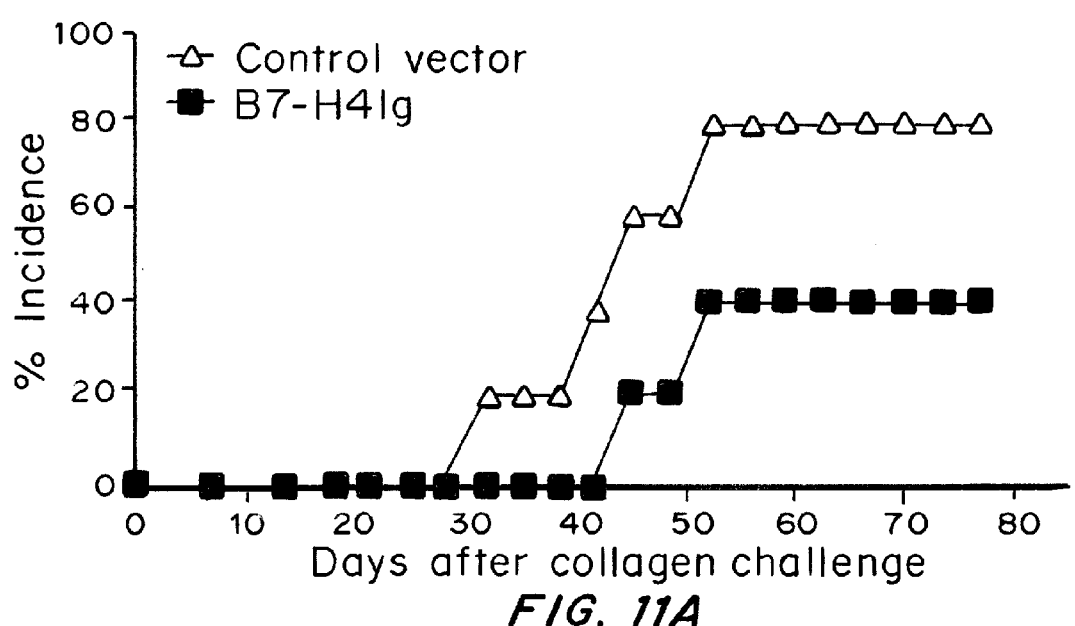
FIG. 11a shows a line graph of incidence of mice immunized with chicken type II collagen in CFA on day 0 and day 21. Three groups of mice were hydrodynamic injection with control vector (□) or B7-H4Ig (■) on day −1 and day 20; means±s.e.m. (n=5)
Figure 11B:
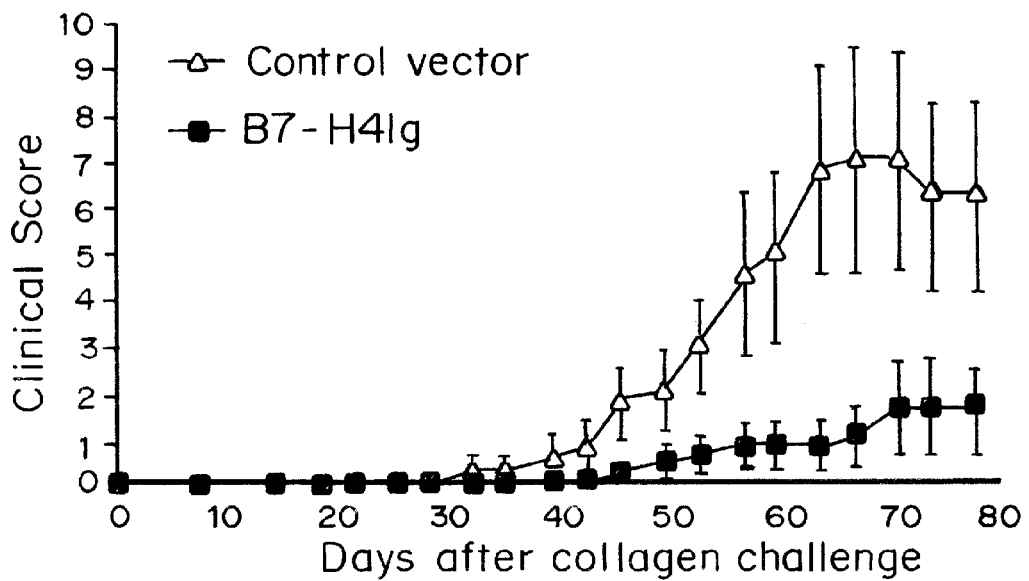
FIG. 11b shows a line graph of clinical score of mice immunized with chicken type II collagen in CFA on day 0 and day 21. Three groups of mice were hydrodynamic injection with control vector (□) or B7-H4Ig (■) on day −1 and day 20; means±s.e.m. (n=5)
Figure 11C:
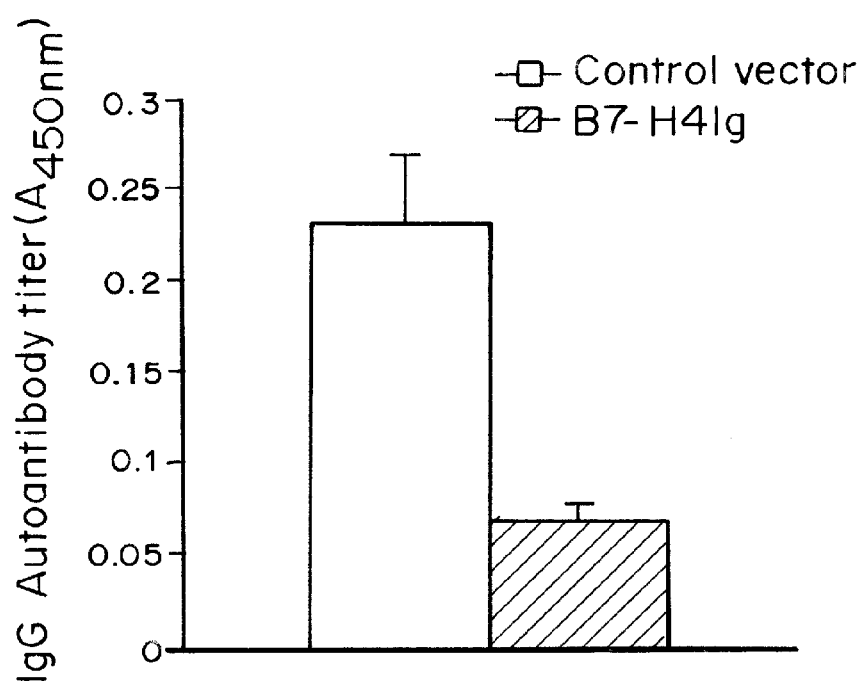
FIG. 11c shows a bar graph of serum levels of anti-CII total IgG. white; control vector, black; B7-H4Ig; means±s.d.
Figure 11D:
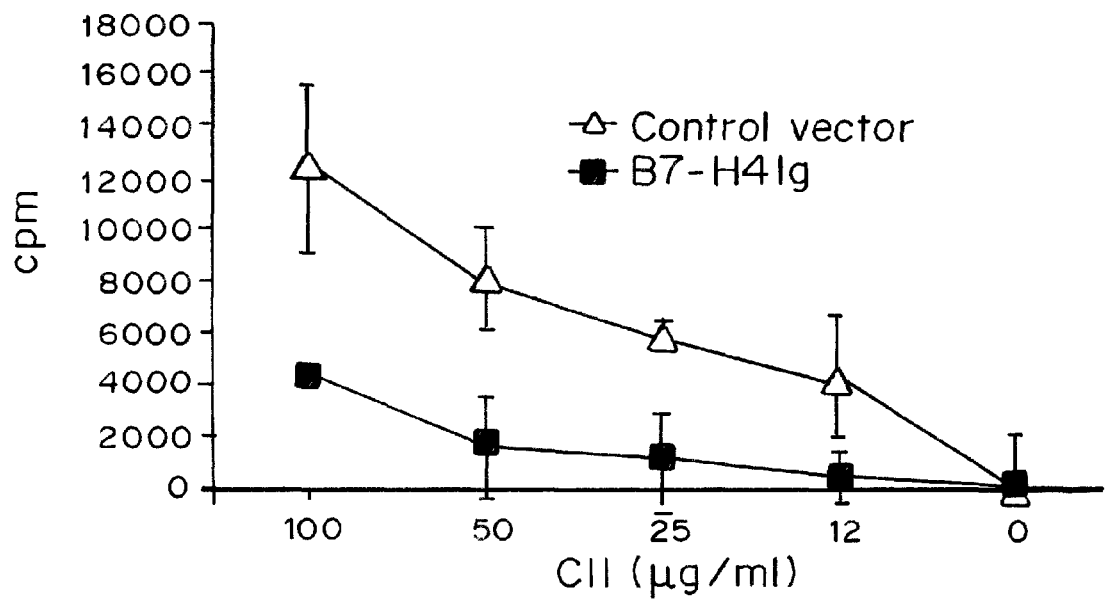
FIG. 11d shows a line graph of counts per minute versus CII µg/ml of whole splenocytes from CIA mice injected with control vector (□) or B7-H4Ig (■) on day 30 were cultured in the presence or absence of the indicated amounts of CII for 72 hr; means±s.d.
Figure 11E:
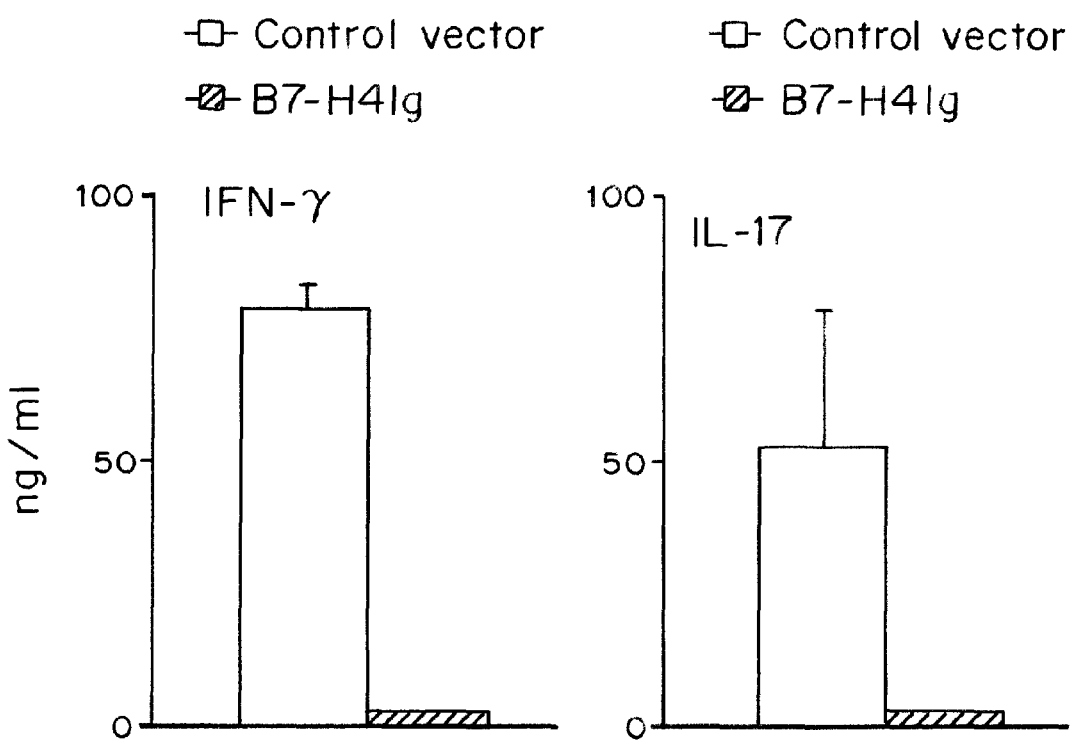
FIG. 11e shows bar graphs showing supernatants of whole splenocytes after a 72 hr culture assessed for IFN-γ and IL-17 production by ELISA; means±s.d.

While the data show that sH4 in RA and SLE murine models promotes progression of diseases, these data also support that endogenous B7-H4 is a checkpoint molecule in suppressing autoimmune responses. Therefore, a potential approach to suppress these autoimmune diseases is to increase the expression of B7-H4 in agonist form in order to engage its putative receptor. The effect of B7-H4Ig fusion protein in which B7-H4 extracellular domain was fused to murine IgG2a Fc portion was described by Sica, G. L. et al. B7-H4, a molecule of the B7 family, negatively regulates T cell immunity. Immunity 18, 849-61 (2003); Chapoval, A. I., Zhu, G. & Chen, L. Immunoglobulin fusion proteins as a tool for evaluation of T-cell costimulatory molecules. Mol Biotechnol 21, 259-64 (2002). The Fc portion of B7-H4Ig could bind Fc receptor to facilitate agonist effect in vivo. The effect of B7-H4Ig in the progression of CIA was then tested. In comparison with control plasmid, B7-H4Ig plasmid treatment one day before CII challenge significantly decreased arthritis incidence and clinical score, as well as delayed the onset of CIA (FIGS. 11a & b). Furthermore, B7-H4Ig plasmid treatment suppressed the production of total IgG (FIG. 11c) and $IgG_1$, $IgG_{2a}$ and $IgG_{2b}$ autoantibodies to CII (FIG. 12). Proliferation of splenocytes and CD4+ T cells (FIG. 11d and FIG. 13) as well as IFN-γ and IL-17 production in response to CII were also significantly suppressed upon B7-H4Ig treatment (FIG. 11e). Collectively, the results demonstrate that B7-H4Ig could work as an agonist to suppress both humoral and cellular autoimmunity. In addition, this method should also be effective in suppressing pathogenesis of CIA.

Example 10

Expression of B7-H4Ig in MRL-lpr/lpr Mice Increases Survival

Figure 14:
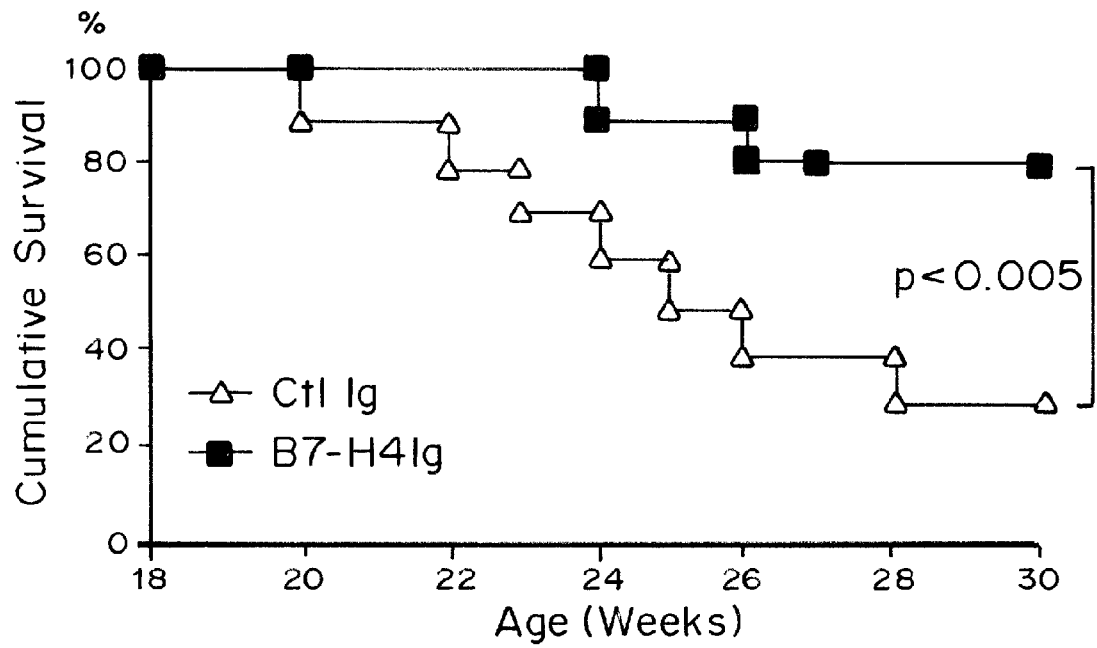
FIG. 14 is a line graph of percent cumulative survival versus age (weeks) in MRL-lpr/lpr mice injected with control mIgG plasmid (□) or B7-H4Ig plasmid (■) at 6, 8, 10 and 12 weeks of age. All phenotypes were analyzed at 19 weeks of age.

MRL-lpr/lpr mice were injected with control mIgG plasmid or B7-H4Ig plasmid at 6, 8, 10 and 12 weeks of age. All phenotypes were analyzed at 19 weeks of age. Each group contained 5-10 mice and each set of experiments were repeated at least twice. FIG. 14 is a line graph of percent cumulative survival versus age (weeks) in MRL-lpr/lpr mice injected with control mIgG plasmid (□) or B7-H4Ig plasmid (■) at 6, 8, 10 and 12 weeks of age. FIG. 14 shows that treatment by B7-H4Ig (murine) vector increases survival of MRL-lpr/lpr mice. All phenotypes were analyzed at 19 weeks of age.

Figure 15:
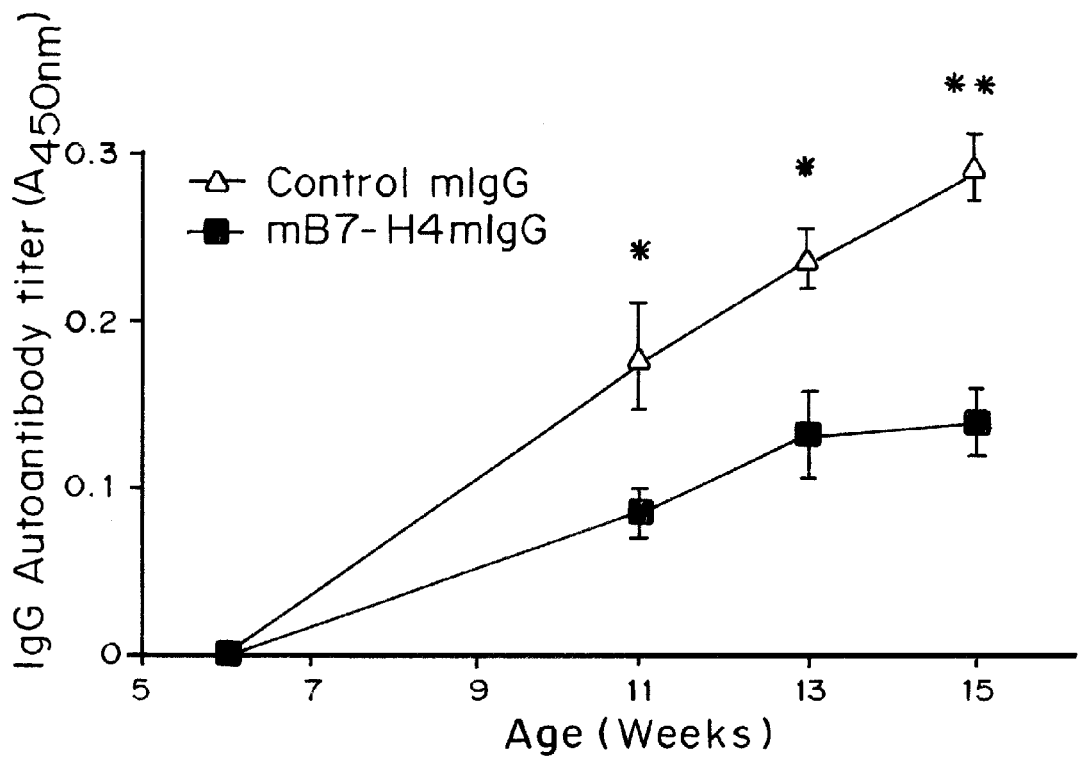
FIG. 15 is a line graph of IgG autoantibody titer ($A_{450nm}$) versus age (weeks) in MRL-lpr/lpr mice injected with control mIgG plasmid (□) or B7-H4Ig plasmid (■).
Figure 16:
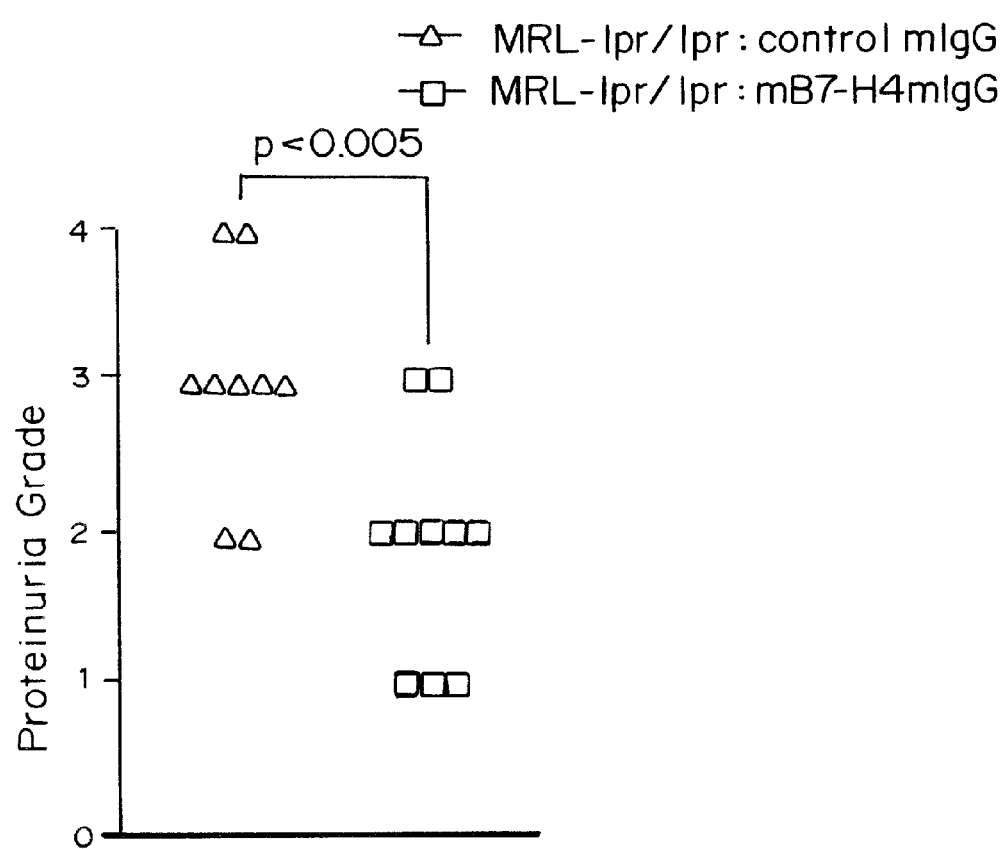
FIG. 16 is a graph of proteinuria grade in MRL-lpr/lpr mice injected with control mIgG plasmid (□) or B7-H4Ig plasmid (□).

FIG. 15 is a line graph of IgG autoantibody titer ($A_{450nm}$) versus age (weeks) in MRL-lpr/lpr mice injected with control mIgG plasmid (□) or B7-H4Ig plasmid (■). FIG. 15 shows that treatment by B7-H4Ig (murine) vector inhibits autoantibodies (anti-DNA) in MRL-lpr/lpr mice. FIG. 16 is a graph of proteinuria grade in MRL-lpr/lpr mice injected with control mIgG plasmid (□) or B7-H4Ig plasmid (□). FIG. 16 shows that treatment by B7-H4Ig (murine) vector inhibits kidney damage in MRL-lpr/lpr mice (1).

Statistical analysis. Statistical analysis was performed with the Mann-Whitney U test for single comparison and ANOVA followed by the Scheffe test for multiple comparisons. In all statistical analyses, significance was accepted at P<0.05.

Those skilled in the art will recognize, or be able to ascertain using no more than routine experimentation, many equivalents to the specific embodiments described herein. Such equivalents are intended to be encompassed by the following claims.

I claim:

1. A pharmaceutical composition dosage unit comprising an antibody or antibody fragment that selectively binds an epitope on soluble B7-H4 masked or absent on membrane bound B7-H4;
   wherein the antibody or antibody fragment is present in the dosage unit in an amount effective to reduce or inhibit one or more symptoms of an inflammatory response in an individual in need thereof,
   and a pharmaceutically acceptable carrier for administration by injection of the dosage unit.

2. The pharmaceutical composition of claim 1 in a kit comprising the antibody or antibody fragment in a first unit and the pharmaceutically acceptable carrier in a second unit, wherein the units are combined for administration.

3. The pharmaceutical composition of claim 1 wherein the inflammatory response is associated with an autoimmune disease or disorder.

4. The pharmaceutical composition of claim 1 wherein the inflammatory response is neutrophil-mediated.

5. The pharmaceutical composition of claim 3 wherein the autoimmune disease or disorder is selected from the group consisting of rheumatoid arthritis, systemic lupus erythematosus, alopecia greata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis-juvenile, discoid lupus, essential mixed cryoglobulinemia, fibromyalgia-fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

6. A method for treating or inhibiting one or more symptoms of an inflammatory response in an individual in need thereof comprising
administering to the individual the pharmaceutical composition of claim 1.

7. The method of claim 6 wherein the inflammatory response is associated with an autoimmune disease or disorder.

8. The method of claim 7 wherein the individual has an autoimmune disease selected from the group consisting of rheumatoid arthritis, systemic lupus erythematosus, alopecia greata, anklosing spondylitis, antiphospholipid syndrome, autoimmune addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis-juvenile, discoid lupus, essential mixed cryoglobulinemia, fibromyalgia-fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

9. The pharmaceutical composition of claim 1 wherein the antibody or antibody fragment that binds to soluble B7-H4 is a xenogeneic, allogeneic, syngeneic, or modified forms thereof, such as humanized, single chain or chimeric.

10. The pharmaceutical composition of claim 1 wherein the antibody fragment is a Fab, F(ab')$_2$, or Fv fragment.

11. The method of claim 6 wherein the inflammatory response is neutrophil-mediated.

12. The method of claim 6 wherein the antibody or antibody fragment that binds to soluble B7-H4 is a xenogeneic, allogeneic, syngeneic, or modified forms thereof, such as humanized, single chain or chimeric.

13. The method of claim 6 wherein the antibody fragment is a Fab, F(ab')$_2$, or Fv fragment.

14. The pharmaceutical composition of claim 1 wherein a biological sample from the individual is characterized by elevated levels of soluble B7-H4 compared to a biological sample from a normal individual.

15. The pharmaceutical composition of claim 14 wherein the biological sample is selected from the group consisting of blood, plasma, saliva, lymph, cerebrospinal fluid, and sputum.

16. The method of claim 6 wherein the individual is characterized by elevated serum levels of soluble B7-H4 compared to a normal individual.

* * * * *

UNITED STATES PATENT AND TRADEMARK OFFICE
CERTIFICATE OF CORRECTION

| | | |
|---|---|---|
| PATENT NO. | : 7,931,896 B2 | |
| APPLICATION NO. | : 11/965425 | |
| DATED | : April 26, 2011 | |
| INVENTOR(S) | : Lieping Chen | |

It is certified that error appears in the above-identified patent and that said Letters Patent is hereby corrected as shown below:

Claim 5, column 38, line 55, replace "greata" with --areata--.
Claim 5, column 38, line 62, replace "deficiency, syndrome" with --deficiency syndrome--.
Claim 8, column 39, line 25, replace "greata" with --areata--.
Claim 8, column 39, line 31, replace "deficiency, syndrome" with --deficiency syndrome--.

Signed and Sealed this
Eighteenth Day of October, 2011

David J. Kappos
*Director of the United States Patent and Trademark Office*

SEQUENCE LISTING

```
<160> NUMBER OF SEQ ID NOS: 8

<210> SEQ ID NO 1
<211> LENGTH: 256
<212> TYPE: PRT
<213> ORGANISM: Artificial Sequence
<220> FEATURE:
<223> OTHER INFORMATION: Synthetic fusion protein

<400> SEQUENCE: 1

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125
```

```
Thr Cys Tyr Ile Arg Thr Ser Lys Gly Lys Gly Asn Ala Asn Leu Glu
        130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
                195                 200                 205

Lys Val Val Ser Val Leu Tyr Asn Val Thr Ile Asn Asn Thr Tyr Ser
        210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

<210> SEQ ID NO 2
<211> LENGTH: 156
<212> TYPE: PRT
<213> ORGANISM: Artificial Sequence
<220> FEATURE:
<223> OTHER INFORMATION: Synthetic fusion protein

<400> SEQUENCE: 2

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
                20                  25                  30

Gly Lys His Phe Ile Thr Val Thr Thr Phe Thr Ser Ala Gly Asn Ile
            35                  40                  45

Gly Glu Asp Gly Thr Leu Ser Cys Thr Phe Glu Pro Asp Ile Lys Leu
        50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
                100                 105                 110

Ala Ser Leu Arg Leu Lys Asn Val Gln Leu Thr Asp Ala Gly Thr Tyr
            115                 120                 125

Thr Cys Tyr Ile Arg Thr Ser Lys Gly Lys Gly Asn Ala Asn Leu Glu
        130                 135                 140

Tyr Lys Thr Gly Ala Phe Ser Met Pro Glu Ile Asn
145                 150                 155

<210> SEQ ID NO 3
<211> LENGTH: 25
<212> TYPE: DNA
<213> ORGANISM: Artificial Sequence
<220> FEATURE:
<223> OTHER INFORMATION: Synthetic primer

<400> SEQUENCE: 3
gttagatagg gtctcactgg gtagc                                        25

<210> SEQ ID NO 4
<211> LENGTH: 25
```

```
<212> TYPE: DNA
<213> ORGANISM: Artificial Sequence
<220> FEATURE:
<223> OTHER INFORMATION: Synthetic primer

<400> SEQUENCE: 4
cctacagcct tcagtatgcc agaga                                              25

<210> SEQ ID NO 5
<211> LENGTH: 25
<212> TYPE: DNA
<213> ORGANISM: Artificial Sequence
<220> FEATURE:
<223> OTHER INFORMATION: Synthetic primer

<400> SEQUENCE: 5
agactagtga gacgtgctac ttcca                                              25

<210> SEQ ID NO 6
<211> LENGTH: 32
<212> TYPE: DNA
<213> ORGANISM: Artificial Sequecne
<220> FEATURE:
<223> OTHER INFORMATION: Synthetic 5' primer for B7H4

<400> SEQUENCE: 6
ccgctcgagc caccatggct tccttggggc ag                                      32

<210> SEQ ID NO 7
<211> LENGTH: 31
<212> TYPE: DNA
<213> ORGANISM: Artificial Sequence
<220> FEATURE:
<223> OTHER INFORMATION: Synthetic B7-H4V 3' primer

<400> SEQUENCE: 7
cggaattccg ctaatttatc tctggcatac t                                       31

<210> SEQ ID NO 8
<211> LENGTH: 31
<212> TYPE: DNA
<213> ORGANISM: Artificial Sequence
<220> FEATURE:
<223> OTHER INFORMATION: Synthetic B7-H4VC 3' primer

<400> SEQUENCE: 8
cggaattccg ctaagagttc agcaactgca g                                       31
```